(12) United States Patent
Dobak, III et al.

(10) Patent No.: US 11,976,332 B2
(45) Date of Patent: May 7, 2024

(54) GENE CLASSIFIERS AND USES THEREOF IN NON-MELANOMA SKIN CANCERS

(71) Applicant: DermTech, Inc., La Jolla, CA (US)

(72) Inventors: John Daniel Dobak, III, La Jolla, CA (US); Burkhard Jansen, La Jolla, CA (US); Zuxu Yao, San Diego, CA (US)

(73) Assignee: DERMTECH, INC., San Diego, CA (US)

( * ) Notice: Subject to any disclaimer, the term of this patent is extended or adjusted under 35 U.S.C. 154(b) by 911 days.

(21) Appl. No.: 16/969,526

(22) PCT Filed: Feb. 14, 2019

(86) PCT No.: PCT/US2019/018102
§ 371 (c)(1),
(2) Date: Aug. 12, 2020

(87) PCT Pub. No.: WO2019/161126
PCT Pub. Date: Aug. 22, 2019

(65) Prior Publication Data
US 2020/0407800 A1    Dec. 31, 2020

Related U.S. Application Data

(60) Provisional application No. 62/630,627, filed on Feb. 14, 2018.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/156* (2013.01); *C12Q 2600/158* (2013.01)

(58) Field of Classification Search
CPC .................................................. C12Q 1/6886
See application file for complete search history.

(56) References Cited

U.S. PATENT DOCUMENTS

| | | |
|---|---|---|
| 3,441,430 A | 4/1969 | Peterson et al. |
| 4,122,947 A | 10/1978 | Falla |
| 4,365,409 A | 12/1982 | Riley et al. |
| 4,388,432 A | 6/1983 | Eskay |
| 4,458,066 A | 7/1984 | Caruthers et al. |
| 4,537,776 A | 8/1985 | Cooper |
| 4,683,195 A | 7/1987 | Mullis et al. |
| 4,683,202 A | 7/1987 | Mullis |
| 4,836,217 A | 6/1989 | Fischer |
| 4,851,510 A | 7/1989 | Khan |
| 4,971,800 A | 11/1990 | Chess et al. |
| 5,190,049 A | 3/1993 | Briggs et al. |
| 5,460,939 A | 10/1995 | Hansbrough et al. |
| 5,493,009 A | 2/1996 | Ferrone |
| 5,583,032 A | 12/1996 | Torrence et al. |
| 5,625,005 A | 4/1997 | Mallya et al. |
| 5,654,286 A | 8/1997 | Hostetler |
| 5,753,612 A | 5/1998 | Mitrani |
| 5,786,146 A | 7/1998 | Herman et al. |
| 5,807,522 A | 9/1998 | Brown et al. |
| 5,811,239 A | 9/1998 | Frayne |
| 5,858,683 A | 1/1999 | Keesee et al. |
| 5,921,396 A | 7/1999 | Brown, Jr. |
| 5,962,477 A | 10/1999 | Mak |
| 5,972,602 A | 10/1999 | Hyland et al. |
| 5,989,815 A | 11/1999 | Skolnick et al. |
| 6,017,704 A | 1/2000 | Herman et al. |
| 6,033,854 A | 3/2000 | Kurnit et al. |
| 6,054,277 A | 4/2000 | Furcht et al. |
| 6,056,859 A | 5/2000 | Ramsey et al. |
| 6,106,732 A | 8/2000 | Johnston et al. |
| 6,129,983 A | 10/2000 | Schuemann et al. |
| 6,176,836 B1 | 1/2001 | Trudil et al. |
| 6,180,349 B1 | 1/2001 | Ginzinger et al. |
| 6,200,756 B1 | 3/2001 | Herman et al. |
| 6,203,987 B1 | 3/2001 | Friend et al. |
| 6,265,171 B1 | 7/2001 | Herman et al. |
| 6,306,597 B1 | 10/2001 | Macevicz |
| 6,312,909 B1 | 11/2001 | Shyjan |
| 6,331,393 B1 | 12/2001 | Laird et al. |
| 6,337,182 B1 | 1/2002 | Cerutti et al. |
| 6,355,439 B1 | 3/2002 | Chung et al. |

(Continued)

FOREIGN PATENT DOCUMENTS

| | | |
|---|---|---|
| CN | 1612936 A | 5/2005 |
| CN | 104105798 A | 10/2014 |

(Continued)

OTHER PUBLICATIONS

Berg et al. Early p53 alterations in mouse skin carcinogenesis by UVB radiation: immunohistochemical detection of mutant p53 protein in clusters of preneoplastic epidermal cells. PNAS USA 93(1):274-8 (1996).
Capone et al. Systems analysis of human T helper17 cell differentiation uncovers distinct time-regulated transcriptional modules. iScience. 24:102492 (2021).
Cerda et al. Geometry and Physics of Wrinkling. Phys Rev Lett 90(7):074302 (2003).
Chang et al. Osteopontin Expression in Normal Skin and Non-melanoma Skin Tumors. J Histochem Cytochem 56(1):57-66 (2007).
Co-pending U.S. Appl. No. 17/534,177, inventors Dobak; John Daniel et al., filed Nov. 23, 2021.
Co-pending U.S. Appl. No. 29/770,783, inventors Dobak; John et al., filed Feb. 16, 2021.

(Continued)

*Primary Examiner* — Kenneth R Horlick
(74) *Attorney, Agent, or Firm* — WILSON SONSINI GOODRICH & ROSATI

(57) ABSTRACT

Described herein are methods, systems, and compositions for non-invasively diagnosing or detecting a skin disease or disorder. Diagnosing or detecting a non-melanoma skin cancer as provided herein comprises detecting gene expression levels of a set of identified genes and in some instances further detecting mutations in a gene of interest.

19 Claims, 19 Drawing Sheets

(56) References Cited

U.S. PATENT DOCUMENTS

| | | |
|---|---|---|
| 6,410,019 B1 | 6/2002 | De et al. |
| 6,410,240 B1 | 6/2002 | Hodge et al. |
| 6,447,463 B1 | 9/2002 | Borkowski |
| 6,551,799 B2 | 4/2003 | Gurney et al. |
| 6,642,298 B2 | 11/2003 | Foreman et al. |
| 6,720,145 B2 | 4/2004 | Rheins et al. |
| 6,726,971 B1 | 4/2004 | Wong |
| 6,797,470 B2 | 9/2004 | Barany et al. |
| 6,891,022 B1 | 5/2005 | Stewart et al. |
| 6,949,338 B2 | 9/2005 | Rheins et al. |
| 7,037,687 B2 | 5/2006 | Williams et al. |
| 7,083,917 B2 | 8/2006 | Barany et al. |
| 7,166,434 B2 | 1/2007 | Barany et al. |
| 7,169,560 B2 | 1/2007 | Lapidus et al. |
| 7,183,057 B2 | 2/2007 | Benson |
| 7,186,512 B2 | 3/2007 | Martienssen et al. |
| 7,232,656 B2 | 6/2007 | Balasubramanian et al. |
| 7,247,426 B2 | 7/2007 | Yakhini et al. |
| 7,267,951 B2 | 9/2007 | Alani et al. |
| 7,297,480 B2 | 11/2007 | Vogt |
| 7,320,865 B2 | 1/2008 | Barany et al. |
| 7,332,285 B2 | 2/2008 | Barany et al. |
| 7,364,858 B2 | 4/2008 | Barany et al. |
| 7,396,871 B2 | 7/2008 | Shoaf et al. |
| 7,429,453 B2 | 9/2008 | Barany et al. |
| 7,459,274 B2 | 12/2008 | Lakey et al. |
| 7,553,627 B2 | 6/2009 | Laird et al. |
| 7,598,035 B2 | 10/2009 | Macevicz |
| 7,611,869 B2 | 11/2009 | Fan |
| 7,615,349 B2 | 11/2009 | Riker et al. |
| 7,645,596 B2 | 1/2010 | Williams et al. |
| 7,662,558 B2 | 2/2010 | Liew |
| 7,700,324 B1 | 4/2010 | Issa et al. |
| 7,769,400 B2 | 8/2010 | Backholm et al. |
| 7,771,950 B2 | 8/2010 | Wohlgemuth et al. |
| 7,901,880 B2 | 3/2011 | Jeddeloh et al. |
| 7,910,296 B2 | 3/2011 | Jeddeloh et al. |
| 7,919,246 B2 | 4/2011 | Lai et al. |
| 7,921,999 B1 | 4/2011 | Kimball |
| 7,972,788 B2 | 7/2011 | Miyata et al. |
| 7,989,165 B2 | 8/2011 | Benson |
| 8,067,173 B2 | 11/2011 | Liew |
| 8,389,215 B2 | 3/2013 | Krueger et al. |
| 8,492,102 B2 | 7/2013 | Kashani-Sabet et al. |
| 8,541,170 B2 | 9/2013 | Kennedy et al. |
| D692,149 S | 10/2013 | Uematsu |
| D692,152 S | 10/2013 | Inoo |
| 8,700,432 B2 | 4/2014 | Letts |
| D704,343 S | 5/2014 | Inoo et al. |
| 8,729,252 B2 | 5/2014 | Himmelreich et al. |
| 8,741,561 B2 | 6/2014 | Terunuma et al. |
| 8,938,684 B2 | 1/2015 | Guertler et al. |
| 9,057,109 B2 | 6/2015 | Chang |
| D738,514 S | 9/2015 | Tagami et al. |
| D747,455 S | 1/2016 | Uematsu |
| D786,282 S | 5/2017 | Donnelly |
| D788,142 S | 5/2017 | Burke |
| D816,697 S | 5/2018 | Ledford et al. |
| D816,699 S | 5/2018 | Ledford et al. |
| D816,700 S | 5/2018 | Bayer et al. |
| D857,212 S | 8/2019 | Sugaya et al. |
| 10,407,729 B2 | 9/2019 | Chang |
| 10,709,428 B2 | 7/2020 | Palmer et al. |
| 10,781,200 B2 | 9/2020 | McDonald et al. |
| D899,606 S | 10/2020 | Kang |
| D899,607 S | 10/2020 | Ryu |
| 10,852,307 B2 | 12/2020 | Leung et al. |
| 10,995,366 B2 | 5/2021 | Mahmood et al. |
| D944,284 S | 2/2022 | Metzger et al. |
| D944,286 S | 2/2022 | Sanchez et al. |
| D946,017 S | 3/2022 | Courtney et al. |
| 11,307,876 B1 | 4/2022 | Leonard, II et al. |
| 2001/0031481 A1 | 10/2001 | Liotta et al. |
| 2001/0044421 A1 | 11/2001 | Von Borstel et al. |
| 2001/0051344 A1 | 12/2001 | Shalon et al. |
| 2002/0037538 A1 | 3/2002 | Trepicchio et al. |
| 2002/0086019 A1 | 7/2002 | Wolf et al. |
| 2002/0110822 A1 | 8/2002 | Rheins et al. |
| 2002/0110824 A1 | 8/2002 | Rheins et al. |
| 2002/0115086 A1 | 8/2002 | Rheins et al. |
| 2002/0119471 A1 | 8/2002 | Rheins et al. |
| 2002/0127573 A1 | 9/2002 | Rheins et al. |
| 2002/0150918 A1 | 10/2002 | Rheins et al. |
| 2002/0165192 A1 | 11/2002 | Kerr et al. |
| 2002/0197604 A1 | 12/2002 | Rheins et al. |
| 2003/0010888 A1 | 1/2003 | Shimada et al. |
| 2003/0032617 A1 | 2/2003 | Harel et al. |
| 2003/0037538 A1 | 2/2003 | Rendahl et al. |
| 2003/0044406 A1 | 3/2003 | Dingivan |
| 2003/0045810 A1 | 3/2003 | Borkowski |
| 2003/0049256 A1 | 3/2003 | Tobinick |
| 2003/0073888 A1 | 4/2003 | Blumenberg |
| 2003/0098580 A1 | 5/2003 | Christy |
| 2003/0108896 A1 | 6/2003 | Vogt |
| 2003/0113906 A1 | 6/2003 | Sangha et al. |
| 2003/0133936 A1 | 7/2003 | Byrne et al. |
| 2003/0152923 A1 | 8/2003 | Yakhini et al. |
| 2003/0167556 A1 | 9/2003 | Kelley |
| 2003/0175736 A1 | 9/2003 | Chinnaiyan et al. |
| 2003/0207315 A1 | 11/2003 | Burmer et al. |
| 2003/0208138 A1 | 11/2003 | Olson |
| 2003/0224422 A1 | 12/2003 | Evans et al. |
| 2003/0224465 A1 | 12/2003 | Nevalainen et al. |
| 2003/0228617 A1 | 12/2003 | Aune et al. |
| 2004/0191782 A1 | 9/2004 | Wang |
| 2005/0069879 A1 | 3/2005 | Berlin |
| 2005/0193434 A1 | 9/2005 | Leonard et al. |
| 2005/0221334 A1 | 10/2005 | Benson |
| 2005/0261210 A1 | 11/2005 | Bhatnagar et al. |
| 2005/0287593 A1 | 12/2005 | Kastelein et al. |
| 2006/0019256 A1 | 1/2006 | Clarke et al. |
| 2006/0019286 A1 | 1/2006 | Horvitz et al. |
| 2006/0040335 A1 | 2/2006 | Butt et al. |
| 2006/0182755 A1 | 8/2006 | Bodary-Winter et al. |
| 2006/0242554 A1 | 10/2006 | Gerace et al. |
| 2006/0271309 A1 | 11/2006 | Showe et al. |
| 2006/0294615 A1 | 12/2006 | Lin |
| 2007/0051376 A1 | 3/2007 | Kulichikhin et al. |
| 2007/0059717 A1 | 3/2007 | Pascual et al. |
| 2007/0066967 A1 | 3/2007 | Sieckmann et al. |
| 2007/0077553 A1 | 4/2007 | Bentwich |
| 2007/0082347 A1 | 4/2007 | Lanchbury et al. |
| 2007/0087323 A1 | 4/2007 | Armitage et al. |
| 2007/0099209 A1 | 5/2007 | Clarke et al. |
| 2007/0179198 A1 | 8/2007 | Iwai et al. |
| 2007/0202540 A1 | 8/2007 | Benson |
| 2007/0243537 A1 | 10/2007 | Tuck et al. |
| 2007/0281314 A1 | 12/2007 | Benson |
| 2008/0032293 A1 | 2/2008 | Szabo et al. |
| 2008/0070883 A1 | 3/2008 | Nagpal |
| 2008/0113360 A1 | 5/2008 | Riker et al. |
| 2008/0131902 A1 | 6/2008 | Maor et al. |
| 2008/0138819 A1 | 6/2008 | Vogt |
| 2008/0200870 A1 | 8/2008 | Palmroos et al. |
| 2008/0251201 A1 | 10/2008 | Sikkel et al. |
| 2008/0254464 A1 | 10/2008 | Weindruch et al. |
| 2008/0260744 A1 | 10/2008 | Gaitanaris et al. |
| 2008/0274908 A1 | 11/2008 | Chang |
| 2009/0042204 A1 | 2/2009 | Thiboutot |
| 2009/0048510 A1 | 2/2009 | Miller et al. |
| 2009/0082265 A1 | 3/2009 | Bartel et al. |
| 2009/0111095 A1 | 4/2009 | Nishimura et al. |
| 2009/0155791 A1 | 6/2009 | Wojdacz et al. |
| 2009/0203639 A1 | 8/2009 | Van Criekinge et al. |
| 2009/0233319 A1 | 9/2009 | Katagiri et al. |
| 2009/0246768 A1 | 10/2009 | Sawalha et al. |
| 2009/0263792 A1 | 10/2009 | Miyata et al. |
| 2009/0280479 A1 | 11/2009 | Hoon et al. |
| 2009/0298060 A1 | 12/2009 | Lal et al. |
| 2009/0299640 A1 | 12/2009 | Ellis et al. |
| 2009/0305242 A1 | 12/2009 | Miyata et al. |
| 2009/0318534 A1 | 12/2009 | Gallo et al. |
| 2010/0009375 A1 | 1/2010 | Sherman et al. |
| 2010/0086501 A1 | 4/2010 | Chang et al. |

(56) References Cited

U.S. PATENT DOCUMENTS

| | | |
|---|---|---|
| 2010/0105102 A1 | 4/2010 | Hanes et al. |
| 2010/0144836 A1 | 6/2010 | Van Engeland et al. |
| 2010/0233718 A1 | 9/2010 | Aubert et al. |
| 2010/0267033 A1 | 10/2010 | Abbas et al. |
| 2010/0279877 A1 | 11/2010 | Vogt |
| 2011/0023142 A1 | 1/2011 | Ostertag et al. |
| 2011/0033842 A1 | 2/2011 | Moon et al. |
| 2011/0040571 A1 | 2/2011 | Warren |
| 2011/0059113 A1 | 3/2011 | Celebi |
| 2011/0091384 A1 | 4/2011 | Alani et al. |
| 2011/0158953 A1 | 6/2011 | Scott |
| 2011/0159496 A1 | 6/2011 | Kashani-Sabet et al. |
| 2011/0160080 A1 | 6/2011 | Chang |
| 2011/0212099 A1 | 9/2011 | Liang et al. |
| 2011/0236902 A1 | 9/2011 | Soito et al. |
| 2011/0250251 A1 | 10/2011 | Maes et al. |
| 2011/0262464 A1 | 10/2011 | Chin et al. |
| 2011/0287034 A1 | 11/2011 | Frank et al. |
| 2012/0065086 A1 | 3/2012 | Benson |
| 2012/0071343 A1 | 3/2012 | Ma et al. |
| 2012/0094853 A1 | 4/2012 | Clark et al. |
| 2012/0171193 A1 | 7/2012 | Blaser et al. |
| 2012/0201750 A1 | 8/2012 | Ryu |
| 2013/0079423 A1 | 3/2013 | Abkevich et al. |
| 2013/0143747 A1 | 6/2013 | Gutin et al. |
| 2013/0244256 A1 | 9/2013 | Clarke et al. |
| 2013/0296185 A1 | 11/2013 | Benson |
| 2013/0302242 A1 | 11/2013 | Stone et al. |
| 2013/0344481 A1 | 12/2013 | Kashani et al. |
| 2014/0037645 A1 | 2/2014 | Rubtsov et al. |
| 2014/0045915 A1 | 2/2014 | Skog et al. |
| 2014/0065147 A1 | 3/2014 | Kastelein et al. |
| 2014/0105796 A1 | 4/2014 | Nagy |
| 2014/0154684 A1 | 6/2014 | Chang |
| 2014/0206574 A1 | 7/2014 | Chapman et al. |
| 2014/0206957 A1 | 7/2014 | Tseng et al. |
| 2014/0272998 A1 | 9/2014 | Ralfkiaer et al. |
| 2014/0323331 A1 | 10/2014 | Chang et al. |
| 2015/0005184 A1 | 1/2015 | Alsobrook et al. |
| 2015/0133328 A1 | 5/2015 | Ikuta et al. |
| 2015/0148239 A1* | 5/2015 | Peter .................. C12Q 1/6841 506/3 |
| 2015/0259739 A1 | 9/2015 | Chang et al. |
| 2015/0361500 A1 | 12/2015 | Ang et al. |
| 2015/0361509 A1 | 12/2015 | Chang |
| 2015/0376717 A1 | 12/2015 | Thomas et al. |
| 2015/0377751 A1 | 12/2015 | Wehmeyer et al. |
| 2016/0000936 A1 | 1/2016 | Cuff et al. |
| 2016/0024595 A1 | 1/2016 | Alsobrook, II |
| 2016/0040216 A1 | 2/2016 | Akins et al. |
| 2016/0051493 A1 | 2/2016 | Lumpkin et al. |
| 2016/0116467 A1 | 4/2016 | Neuman |
| 2016/0215326 A1 | 7/2016 | Martin et al. |
| 2017/0002432 A1 | 1/2017 | Apte et al. |
| 2017/0044232 A1* | 2/2017 | de Sauvage ....... A61K 31/5513 |
| 2017/0115291 A1 | 4/2017 | Wong et al. |
| 2017/0138962 A1 | 5/2017 | Southern |
| 2017/0176455 A1 | 6/2017 | Leung et al. |
| 2017/0329929 A1 | 11/2017 | Fishman |
| 2018/0035073 A1 | 2/2018 | Ma et al. |
| 2018/0057852 A1 | 3/2018 | Takats et al. |
| 2018/0110500 A1 | 4/2018 | Palmer et al. |
| 2018/0128714 A1 | 5/2018 | Adey et al. |
| 2018/0296591 A1 | 10/2018 | Yu et al. |
| 2018/0363066 A1 | 12/2018 | Chalmers et al. |
| 2019/0214116 A1 | 7/2019 | Eberting |
| 2019/0367994 A1 | 12/2019 | Chang |
| 2019/0369119 A1 | 12/2019 | Zhuang et al. |
| 2020/0066414 A1 | 2/2020 | Neff et al. |
| 2020/0149115 A1 | 5/2020 | Dobak et al. |
| 2020/0289099 A1 | 9/2020 | Palmer et al. |
| 2020/0308649 A1 | 10/2020 | Dobak et al. |
| 2020/0308657 A1 | 10/2020 | Dobak et al. |
| 2020/0319205 A1 | 10/2020 | Dobak et al. |
| 2020/0383665 A1 | 12/2020 | Palmer et al. |
| 2021/0104043 A1 | 4/2021 | Crawford et al. |
| 2021/0196247 A1 | 7/2021 | Palmer et al. |
| 2021/0198749 A1 | 7/2021 | Chang |
| 2021/0222246 A1 | 7/2021 | Dobak et al. |
| 2021/0222247 A1 | 7/2021 | Dobak et al. |
| 2021/0222258 A1 | 7/2021 | Chang |
| 2021/0246514 A1 | 8/2021 | Chang |
| 2021/0324480 A1 | 10/2021 | Dobak et al. |
| 2021/0330245 A1 | 10/2021 | Dobak, III et al. |
| 2021/0332442 A1 | 10/2021 | Dobak, III et al. |
| 2021/0345995 A1 | 11/2021 | Dobak, III et al. |
| 2022/0387005 A1 | 12/2022 | Dobak, III et al. |

FOREIGN PATENT DOCUMENTS

| | | |
|---|---|---|
| CN | 104651521 A | 5/2015 |
| CN | 105662482 A | 6/2016 |
| CN | 106119242 A | 11/2016 |
| CN | 109785903 A | 5/2019 |
| DE | 102022106693 B3 | 3/2023 |
| DE | 102022111890 B3 | 3/2023 |
| EP | 2151505 A1 | 2/2010 |
| JP | S567007 A | 1/1981 |
| JP | S57156456 A | 9/1982 |
| JP | H0852142 A | 2/1996 |
| JP | 2006000385 A | 1/2006 |
| JP | 2007050126 A | 3/2007 |
| JP | 2007259851 A | 10/2007 |
| JP | 2007531529 A | 11/2007 |
| JP | 2010014689 A | 1/2010 |
| KR | 20140069917 A | 6/2014 |
| WO | WO-0010579 A1 | 3/2000 |
| WO | WO-02053773 A2 | 7/2002 |
| WO | WO-03001985 A2 | 1/2003 |
| WO | WO-03064701 A2 | 8/2003 |
| WO | WO-2004047728 A2 | 6/2004 |
| WO | WO-2005012578 A1 | 2/2005 |
| WO | WO-2005091777 A2 | 10/2005 |
| WO | WO-2005100603 A2 | 10/2005 |
| WO | WO-2005108616 A1 | 11/2005 |
| WO | WO-2006002433 A2 | 1/2006 |
| WO | WO-2006039399 A2 | 4/2006 |
| WO | WO-2006056480 A2 | 6/2006 |
| WO | WO-2007023808 A1 | 3/2007 |
| WO | WO-2007124072 A2 | 11/2007 |
| WO | WO-2008137772 A1 | 11/2008 |
| WO | WO-2009021141 A1 | 2/2009 |
| WO | WO-2009048282 A2 | 4/2009 |
| WO | WO-2009049916 A2 | 4/2009 |
| WO | WO-2009140550 A2 | 11/2009 |
| WO | WO-2010025341 A2 | 3/2010 |
| WO | WO-2010097773 A1 | 9/2010 |
| WO | WO-2011039734 A2 | 4/2011 |
| WO | WO-2011067549 A1 | 6/2011 |
| WO | WO-2011109224 A1 | 9/2011 |
| WO | WO-2012013931 A1 | 2/2012 |
| WO | WO-2012115885 A1 | 8/2012 |
| WO | WO-2012125411 A1 | 9/2012 |
| WO | WO-2012174282 A2 | 12/2012 |
| WO | WO-2013022995 A2 | 2/2013 |
| WO | WO-2013033609 A2 | 3/2013 |
| WO | WO-2013041724 A1 | 3/2013 |
| WO | WO-2013056042 A1 | 4/2013 |
| WO | WO-2013057241 A1 | 4/2013 |
| WO | WO-2013098797 A2 | 7/2013 |
| WO | WO-2013184905 A1 | 12/2013 |
| WO | WO-2014028461 A2 | 2/2014 |
| WO | WO-2014028884 A2 | 2/2014 |
| WO | WO-2014127359 A1 | 8/2014 |
| WO | WO-2014130507 A1 | 8/2014 |
| WO | WO-2014176446 A1 | 10/2014 |
| WO | WO-2014208645 A1 | 12/2014 |
| WO | WO-2014210467 A1 | 12/2014 |
| WO | WO-2015093998 A1 | 6/2015 |
| WO | WO-2015158765 A1 | 10/2015 |
| WO | WO-2016014705 A1 | 1/2016 |
| WO | WO-2016030287 A1 | 3/2016 |
| WO | WO-2016179043 A1 | 11/2016 |
| WO | WO-2017083576 A1 | 5/2017 |

(56) References Cited

FOREIGN PATENT DOCUMENTS

| WO | WO-2017165199 A1 | 9/2017 |
|---|---|---|
| WO | WO-2018065384 A1 | 4/2018 |
| WO | WO-2018093724 A1 | 5/2018 |
| WO | WO-2018109078 A1 | 6/2018 |
| WO | WO-2018191268 A1 | 10/2018 |
| WO | WO-2018161062 A9 | 11/2018 |
| WO | WO-2019005764 A1 | 1/2019 |
| WO | WO-2019161126 A1 | 8/2019 |
| WO | WO-2019183620 A1 | 9/2019 |
| WO | WO-2019217478 A1 | 11/2019 |
| WO | WO-2020008192 A2 | 1/2020 |
| WO | WO-2020035707 A1 | 2/2020 |
| WO | WO-2020198229 A1 | 10/2020 |
| WO | WO-2020206085 A1 | 10/2020 |
| WO | WO-2021216721 A1 | 10/2021 |
| WO | WO-2021226482 A1 | 11/2021 |
| WO | WO-2022115487 A1 | 6/2022 |
| WO | WO-2022187196 A1 | 9/2022 |
| WO | WO-2022221326 A1 | 10/2022 |
| WO | WO-2022256674 A1 | 12/2022 |

OTHER PUBLICATIONS

Co-pending U.S. Appl. No. 29/770,784, inventors Dobak; John et al., filed Feb. 16, 2021.
Co-pending U.S. Appl. No. 29/770,785, inventors Dobak; John et al., filed Feb. 16, 2021.
Co-pending U.S. Appl. No. 29/770,786, inventors Dobak; John et al., filed Feb. 16, 2021.
Co-pending U.S. Appl. No. 29/796,477, inventor Dobak; John, filed Jun. 24, 2021.
Dalbe et al. Multiscale Stick-Slip Dynamics of Adhesive Tape Peeling. Phys Rev Lett 115(12):128301 (2015).
De Zotti et al. Bending to Kinetic Energy Transfer in Adhesive Peel Front Microinstability. Phys Rev Lett 122(6):068005 (2019).
Del Sordo et al. Basal cell carcinoma with matrical differentiation: expression of beta-catenin [corrected] and osteopontin. Am J Dermatopathol 29(5):470-747 (2007).
Dobbeling et al. Method for simultaneous RNA and DNA isolation from biopsy material, culture cells, plants and bacteria. Biotechniques 22:88-90 (1997).
Dyjack et al. Minimally invasive skin tape strip RNA sequencing identifies novel characteristics of the type 2-high atopic dermatitis disease endotype. J Allergy Clin Immunol. 141(4):1298-1309 (2018).
Emtage et al. IGFL: A secreted family with conserved cysteine residues and similarities to the IGF superfamily. Genomics 88(4):513-520 (2006).
Enderle et al. Monitoring therapy response and resistance mutations in circulating RNA and DNA of plasma from melanoma patients. Obtained from http://cpnr-cw7w.accessdomain.com/sites/default/files/2014_11_14_longitudinal_poster_final3_website.pdf on Aug. 23, 2021 (2014).
Hayre. Oxytocin Levels Inversely Correlate With Skin Age Score and Solar Damage. J Drugs Dermatol 19(12):1146-1148 (2020).
Hennig et al. Automated extraction of DNA and RNA from a single formalin-fixed paraffin-embedded tissue section for analysis of both single-nucleotide polymorphisms and mRNA expression. Clinical Chemistry 56:1845-1853 (2010).
Homey et al. Cutting edge: the orphan chemokine receptor G protein-coupled receptor-2 (GPR-2, CCR10) binds the skin-associated chemokine CCL27 (CTACK/ALP/ILC). J. Immunol. 164:3465-3470 (2000).
Jolivet et al. Solutions for purifying nucleic acids by solid phase reversible immobilization (SPRI). Philippe Jolivet and Joseph W. Foley Ludmer Centre for Neuroinformatics and Mental Health Oct. 21, 2015 pp. 1-6.
Juppner. Functional properties of the PTH/PTHrP receptor. Bone. Aug. 1995; 17(2):Supplement 39S-42S.
Kim et al. Evaluation of Gene Expression Using a Skin Tape Tripping Method. J Allergy Clin Immunol. 135(2):Supplement AB261 (2015).
Krueger et al. Non-invasive gene expression analysis for psoriasis. Available via URL: dermtech.com/wp-content/uploads/2017/03/Psoriasis.pdf (2017).
Lattimore et al. Investigation of Experimental Factors that Underlie BRCA 1/2 mRNA Isoform Expression Variation: Recommendations for Utilizing Targeted RNA Sequencing to Evaluate Potential Spliceogenic Variants. Front. Onc. 8:140 (2018).
Lund et al. Genome-wide identification of novel genes involved in early Th1 and Th2 cell differentiation. J Immunology 178:3648-3660 (2007).
Luo et al. Osteopontin Stimulates Preneoplastic Cellular Proliferation Through Activation of the MAPK Pathway. Mol Cancer Res. 9(8):1018-1029 (2011).
Masuzawa et al. Association of D2-40 and MMP-1 expression with cyst formation in lung metastatic lesions of cutaneous angiosarcoma on the scalp: immunohistochemical analysis of 23 autopsy cases. Hum Patho. 44(12):2751-2759 (2013).
Naito et al. Overexpression Of Ets-1 Transcription Factor In Angiosarcoma Of The Skin. Pathol Res Pract 196(2):103-9 (2000).
Neagu et al. miRNAs in the Diagnosis and Prognosis of Skin Cancer. Front Cell Dev Biol 8:71 (2020).
Nindl et al. Identification of differentially expressed genes in cutaneous squamous cell carcinoma by microarray expression profiling. Mol Cancer 5(1):30 (2006).
Pacifico et al. Loss of CDKN2A and pl4ARF expression occurs frequently in human nonmelanoma skin cancers: Inactivation of CDKN2A in human NMSC. Br J Dermatol 158(2):291-297 (2007).
Pan et al. Expression profiles of Th17 pathway related genes in human systemic lupus erythematosus. Mol Biol Rep. 40:391-399 (2013).
PCT/US2021/028415 International Search Report and Written Opinion dated Aug. 6, 2021.
PCT/US2021/031330 International Search Report and Written Opinion dated Aug. 31, 2021.
PCT/US2021/060641 International Search Report and Written Opinion dated Apr. 6, 2022.
PCT/US2021/060641 Invitation to Pay Additional Fees dated Jan. 26, 2022.
Pedicini et al. Combining network modeling and gene expression microarray analysis to explore the dynamics of Th1 and Th2 cell regulation. PLoS Comput Biol. 6(12):e1001032 (2010).
Rivlin et al. Mutations in the p53 Tumor Suppressor Gene: Important Milestones at the Various Steps of Tumorigenesis. Genes Cancer 2(4):466-474 (2011).
Ruzicka et al. Anti-Interleukin-31 Receptor A Antibody for Atopic Dermatitis. N Engl J Med 376(9):826-835 (2017).
Seibold et al. J Allergy Clin Immunol. vol. 139. Issue 2, Supplement, Abstract 856, p. AB273 (2017).
Sonokoly et al. IL-31: A new link between T cells and pruritus in atopic skin inflammation. J Allergy Clin Immunol. 117:411-417 (2006).
Sugaya et al. Serum Interleukin-15 Levels are not Elevated in Patients with Stage I and II Mycosis Fungoides. Acta Derm Venereol 80:455 (2000).
TechNote 302. Bangs Laboratories, p. 1-5, Jun. 2016.
Thijs et al. Moving toward endotypes in atopic dermatitis: Identification of patient clusters based on serum biomarker analysis. J Allergy Clin Immunol. 140:730-737 (2017).
Thoroddsen et al. Stick-slip substructure in rapid tape peeling. Phys Rev Lett 82(4 Pt 2):046107 (2010).
Torres et al. MicroRNA Ratios Distinguish Melanomas from Nevi. J Invest Dermatol . 140(1):164-173.e7 (2020).
UniProtKB—Q9UJU2 (LEF1_HUMAN) (2000).
U.S. Appl. No. 14/199,900 Notice of Allowance dated Mar. 30, 2015.
U.S. Appl. No. 16/522,291 Office Action dated Apr. 28, 2021.
U.S. Appl. No. 16/522,291 Office Action dated Dec. 7, 2021.
U.S. Appl. No. 16/522,291 Office Action dated Jan. 7, 2021.
U.S. Appl. No. 16/522,291 Office Action dated Sep. 16, 2021.
U.S. Appl. No. 16/603,435 Office Action dated Mar. 10, 2022.
U.S. Appl. No. 16/603,435 Office Action dated Sep. 10, 2021.
U.S. Appl. No. 16/828,289 Office Action dated Dec. 21, 2021.
U.S. Appl. No. 16/874,473 Office Action dated Aug. 6, 2021.

(56) References Cited

OTHER PUBLICATIONS

U.S. Appl. No. 16/874,473 Office Action dated Feb. 5, 2021.
U.S. Appl. No. 16/874,473 Office Action dated Jan. 24, 2022.
U.S. Appl. No. 17/214,675 Office Action dated Jul. 27, 2021.
U.S. Appl. No. 17/214,675 Office Action dated Mar. 29, 2022.
U.S. Appl. No. 17/214,675 Office Action dated Nov. 29, 2021.
U.S. Appl. No. 17/214,695 Office Action dated Apr. 5, 2022.
U.S. Appl. No. 17/214,695 Office Action dated Jul. 27, 2021.
U.S. Appl. No. 17/214,695 Office Action dated Nov. 29, 2021.
Wang et al. Frequency and features of TP53 mutation in 30 Chinese patients with sporadic basal cell carcinoma. Clin Exp Dermatol 39(7):829-834 (2014).
Wang et al. Simultaneous Extraction of DNA and RNA from Hepatocellular Carcinoma (Hep G2) Based on Silica-Coated Magnetic Nanoparticles. J. Nanosci. Nanotechnol. 17:802-806 (2017).
Weber et al. Categorical meta-analysis of Osteopontin as a clinical cancer marker. Oncol rep 25(2):433-441 (2011).
Zhou et al. Age-specific changes in the molecular phenotype of patients with moderate-to-severe atopic dermatitis. J Allergy Clin Immunol. 144(1):144-156 (2019) (With Supplementary Material).
Acevedo et al. Analysis of the mechanisms mediating tumor-specific changes in gene expression in human liver tumors. Cancer Res. 68:2641-2651 (2008).
Ackerman et al. Charcot-Leyden crystal protein (galectin-10) is not a dual function galectin with lysophospholipase activity but binds a lysophospholipase inhibitor in a novel structural fashion. J Biol Chem 277(17): 14859-148-68 (2002).
Affymetrix GeneChip Human Genome U133 Array Set HG-U133A, Geo Expression, Mar. 11, 2002 (XP002361324).
Affymetrix HG U133 Gene Chip (www.affymetrix.com U133 gene chip) accessed Oct. 13, 2015.
Affymetrix NetAffxTM Analysis Center (available via URL: https://www.affynnetrix.conn/analysis/netaffx/showresults.affx. printed on Oct. 21, 2020 (2020).
Aitman. DNA microarrays in medical practice. BMJ. 323(7313):611-615 (2001).
Albert et al. Years of potential life lost: another indicator of the impact of cutaneous malignant melanoma on society. J Am Acad Dermato 23(2 Pt 1):308-310 (1990).
Alberts et al. The immune system. Molecular Biology of The Cell. New York, NY, Garland Publishing, Inc. pp 1229-1235 (1994).
Allison et al. A mixture model approach for the analysis of microarray gene expression data. Computational Statistics and Data Analysis 39:1-20 (2002).
Al-Shobaili et al. Biochemical markers of oxidative and nitrosative stress in acne vulgaris: correlation with disease activity. J Clin Lab Anal. 2013. 27(1):45-52.
Applied Biosystems, User Bulletin #2: Relative quantitation of gene expression. http://docs.appliedbiosystems.com/pebiodocs/04303859.pdf (2001).
Armstrong et al., The epidemiology of UV induced skin cancer. Journal of Photochemistry and Photobiology B: Biology 63(1-3):8-18 (2001).
Asada et al. Cytokine Gene Expression during the Elicitation Phase of Contact Sensitivity: Regulation by Endogenous IL-4. Journal of Investigative Dermatology 108(4):406-411 (1997).
Asadullah et al. Cytokines: interleukin and interferon therapy in dermatology. Clinical & Experimental Dermatology 27:578-584 (2002).
Baehrecke. miRNAs: micro managers of programmed cell death. Curr Biol 13(12):R473-R475 (2003).
Baggerly et al. Deriving Chemosensitivity From Cell Lines: Forensic Bioinformatics And Reproducible Research In High-Throughput Biology. The Annals of Applied Sciences 3:1309-1334 (2009).
Baker et al. Normal keratinocytes express Toll-like receptors (TLRs) 1, 2 and 5: modulation of TLR expression in chronic plaque psoriasis. Br J Dermatol 148(4):670-679 (2003).
Baldi et al. A Bayesian framework for the analysis of microarray expression data: regularized t-test and statistical inferences of gene changes. Bioinformatics 17(6):509-519 (2001).

Baldi et al. cDNA array technology in melanoma: an overview. J. Cell. Physiol. 196(2):219-223 (2003).
Balic et al. High quality assessment of DNA methylation in archival tissues from colorectal cancer patients using quantitative high-resolution melting analysis. J. Mol. Diagn. 11:102-108 (2009).
Ball et al. Targeted and genome-scale methylomics reveals gene body signatures in human cell lines. Nat. Biotechnol 27:361-368 (2009).
Bartel. MicroRNAs: genomics, biogenesis, mechanism, and function. Cell 116(2): 281-297 (2004).
Bashir et al. Physical and physiological effects of stratum corneum tape stripping. Skin Res Technol 7(1):40-48 (2001).
Bataille. Genetics of familial and sporadic melanoma. Clin. Exp. Dermatol. 25(6):464-467 (2000).
Bayon et al. Mechanisms of cell signaling in immune-mediated inflammation. Cytokines Cell Mol Ther 4(4):275-286 (1998).
Becker et al. Detection of differentially regulated genes in keratinocytes by cDNA array hybridization: Hsp27 and other novel players in response to artificial ultraviolet radiation.J. Invest. Dermatol. 116:983-988 (2001).
Becker et al. Mouse models for melanoma: a personal perspective. Experimental Dermatology 19:157-164 (2010).
Benavides et al. Impaired hair follicle morphogenesis and cycling with abnormal epidermal differentiation in nackt mice, a cathepsin L-deficient mutation. Am J Pathol 161(2):693-703 (2002).
Benner, et al. Evolution, language and analogy in functional genomics. Trends in Genetics, 17:414-418 (2001).
Benson et al. A comparison of keratin gene expression between inflamed and control skin obtained by tape harvest. Journal of Investigative Dermatology 122(3):A48 (2004).
Benson et al. An analysis of select pathogenic messages in lesional and non-lesional psoriatic skin using non-invasive tape harvesting. Journal of Investigative Dermatology 126:2234-2241 (2006).
Benson et al. GenBank. Nucleic Acids. Res. 30(1):17-20 (2002).
Berardesca et al., Reduced ultraviolet-induced DNA damage and apoptosis in human skin with topical application of a photolyase-containing DNA repair enzyme cream: clues to skin cancer prevention. Molecular Medicine Reports 5(2):570-574 (2012).
Berger et al. A reappraisal of the 21-day cumulative irritancy test in man. J. Toxicol-Cut and Ocular Toxicol 1(2):101-107 (1982).
Bernerd et al. Galectin-7 overexpression is associated with the apoptotic process in UVB- induced sunburn keratinocytes. PNAS USA 96(20):11329-11334 (1999).
Bertucci et al. Gene expression profiling of cancer by use of DNA arrays: how far from the clinic. Lancet Oncol 2(11):674-682 (2001).
Bibkova et al. High-throughput DNA methylation profiling using universal bead arrays. Genome Res. 16:383-393 (2006).
Bittner et al. Molecular classification of cutaneous malignant melanoma by gene expression profiling. Nature 406:536-540 (2000).
Boelsma et al. Expression of skin-derived antileukoproteinase (SKALP) in reconstructed human epidermis and its value as a marker for skin irritation. Acta Derm Venereol 78(2):107-113 (1998).
Booken et al. Sezary syndrome is a unique cutaneous T-cell lymphoma as identified by an expanded gene signature including diagnostic marker molecules CDO1 and DNM3. Leukemia 22(2):393-9 (2008).
Borevitz et al. Large-scale identification of single-feature polymorphisms in complex genomes. Genome Res 13(3):513-523 (2003).
Boxman et al. Proteomic analysis of skin irritation reveals the induction of HSP27 by sodium lauryl sulphate in human skin. Br J Dermatol 146(5):777-785 (2002).
Brand et al. IL-1B Protein in Human Skin Lymph Does Not Discriminate Allergic from Irritant Contact Dermatitis. Contact Dermatitis,35:152-156 Munksgaard, Denmark (1996).
Brand et al. Untersuchung menschlicher Hautlymphe: Unterscheiden sich irritative and allergische Kontaktdermatitiden benglich ihres Zytokinmusters? Zeitschrift for Hautkrankheiten, 72:435-440 (1997). (English Abstract).
Brehmer-Andersson et al. Tape-Stripping Method for Cytological Diagnosis of Mycosis Fungoides. Acta Derm-Venereol 47:177-180 (1967).

(56) References Cited

OTHER PUBLICATIONS

Brennecke et al. Bantam encodes a developmentally regulate microRNA that control cell proliferation and regulates the proapoptotic gene hid in *Drosophila*. Cell 113(1):25-36 (2003).
Breslow. Thickness, cross-sectional areas and depth of invasion in the prognosis of cutaneous melanoma. Ann. Surg. 172:902-908 (1970).
Bunge et al. Improvement of Methodology for Assessing Bioequivalence of Topical Products http://www.fda.gov/ohrms/dockets/ac/03/slides3996s2 07 bunge.pdf Oct. 22, 2003.
Bustin. Quantification of mRNA using real-time reverse transcription PCR (RT-PCR): trends and problems. J Mol Endocrinol 29(1):23-39 (2002).
Cachia et al. CDKN2A mutation and deletion status in thin and thick primary melanoma. Clin. Cancer Res. 6(9):3511-3515 (2000).
Cai et al. Kaposi's sarcoma-associated herpesvirus expresses an array of viral microRNAs in latently infected cells. PNAS USA 102(15):5570-5575 (2005).
Calin et al. A MicroRNA signature associated with prognosis and progression in chronic lymphocytic leukemia. N Engl J Med. 353(17):1793-1801 (2005).
Callen et al. AAD Consensus statement on psoriasis therapies. J Amer Acad Dermatol 49:897-899 (2003).
Candiloro et al. Assessing combined methylation-sensitive high resolution melting and pyrosequencing for the analysis of heterogeneous DNA methylation. Epigenetics 6(4):500-507 (2011).
Carr et al. Gene-expression profiling in human cutaneous melanoma. Oncogene 22(20):3076-3080 (2003).
Chakraboty et al. Differential gene expression in genetically matched mouse melanoma cells with different metastatic potential. Gene 315L165 (2003).
Chang et al. A non-invasive genomic assay for the detection of melanoma in suspicious pigmented nevi. Cancer Research Abstract LB-221 (4 pgs.) (2008).
Chang et al. Liver X Receptor Is a Therapeutic Target for Photoaging and Chronological Skin Aging. Mol Endocrinolgy 22:2407-2419 (2008).
Chen et al. MicroRNAs modulate hematopoietic lineage differentiation. Science 303(5654):83-86 (2004).
Chen et al. Type I interferon suppresses memory Th2 cell cytokine secretion from allergic subjects. Allergy 75(3):695-698 (2020).
Cheung et al. Natural variation in human gene expression assessed in lymphoblastoid cells. Nat Genet 33:422-425 (2003).
Childs. Noninvasive gene expression testing in amelanotic melanoma. JAMA Dermatol 154(2):223-224 (2018).
Choi et al. Genomic landscape of cutaneous T cell lymphoma. Nat Genet. 47(9):1011-9 (2015).
Chuaqui et al. Post-analysis follow-up and validation of microarray experiments. Nature Genetics 32(Supp):509-514 (2002).
Chung et al. Factors that control extravascular fibrinolysis. Semin Thromb Hemost 22(6):479-488 (1996).
Chung et al. Sodium dodecyl sulfate induces plasminogen activator inhibitor type 2 expression in epidermal keratinocytes in vivo and in vitro. J Invest Dermatol 117(3):647-653 (2001).
Ciafre et al. Extensive modulation of a set of MicroRNAs in primary glioblastoma. Biochem Biophys Res Commun. 334(4):1351-1358 (2005).
Clauser et al. Rapid mass spectrometromic peptide sequencing and mass matching for characterization of human melanoma proteins isolated by two-dimensional page. PNAS 92:5072-5076(1995).
Colonna. TREMs in the immune system and beyond. Nat Rev Immunol 3(6):445-553 (2003).
Conner et al. Detection of sickle cell Beta S-golbin allele by hybridization with synthetic oligonucleotides. PNAS USA 80:278-282 (1983).
Coquette et al. Analysis of interleukin-lalpha (IL-lalpha) and interleukin-8 (IL-8) expression and release in in vitro reconstructed human epidermis for the prediction of in vivo skin irritation and/or sensitization. Toxicol In Vitro 17(3):311-321 (2003).

Cosini et al. Cytokines and Irritant Contact Dermatitis. Toxicology Letters 102:103:277-282 (1998).
Costello et al. Restriction landmark genome scanning. Meth. Mol Biol 200:53-70 (2002).
Cottrell et al. A real-time PCR assay for DNA-methylation using methylation-specific blockers. Nucleic Acids Res. 32:e10 (2004).
Cottrell et al. Discovery and validation of 3 novel DNA methylation markers of prostate cancer prognosis. J. Urology 177:1753-1758 (2007).
Couzin-Frankel. As Questions Grow, Duke Halts Trials, Launches Investigation. Science Magazine pp. 614-615 (Aug. 2010).
Crow. Type I interferon in the pathogenesis of lupus. Immunol 192:5459-5468 (2014).
Cullander et al. A quantitative minimally invasive assay for the detection of metals in the stratum corneum, J Pharm Biomed Anal. 22(2):265-279 (2000).
Cumberbatch et al. Differential regulation of epidermal langerhans cell migration by interleukins (IL)-Ialpha and IL-Ibeta during irritant- and allergen-induced cutaneous immune responses. Toxicol Appl Pharmacol 182(2):126-135 (2002).
Cummins et al. The colorectal microRNAome. PNAS USA 103(10):3687-3692 (2006).
Curtin et al. Distinct sets of genetic alterations in melanoma. The New England Journal of Medicine 353(20):2135-2147 (2005).
Davies et al. Mutations of the BRAF Gene in Human Cancer. Nature 417:949-954 (2002).
Davy et al. Ephrin-A5 modulates cell adhesion and morphology in an integrin-dependent manner. EMBOJ 19(20):5396-5403 (2000).
Deboyes et al., Reduced number of actinic keratoses with topical application of DNA repair enzyme creams. Journal of drugs in dermatology: JDD 9(12):1519-1521 (2010).
Deeds et al. Patterns of melastatin mRNA expression in melanocytic tumors. Human Pathology 31(11):1346-1356 (2000).
Degraves et al. High-Sensitivity Quantitative PCR Platform. Biotechniques 34(1):106-115 (2003).
Deiman et al. Characteristics and applications of nucleic acid sequence-based amplification (NASBA). Mol. Biotechnol. 20(2):163-179 (2002).
Dekker et al. Characterization of interleukin-1 alpha-induced melanoma cell motility: inhibition by type I and type II receptor-blocking monoclonal antibodies. Melanoma Res. 7(3):223-230 (1997).
Dembinska-Kiec et al. Proangiogenic activity of beta-carotene is coupled with the activation of endothelial cell chemotaxis. Biochimica et Biophysica Acta1740:222-239 (2005).
Deng et al. Targeted bisulfite sequencing reveals changes in DNA methylation associated with nuclear reprogramming. Nat. Biotechnol 27:353-360 (2009).
Dong et al. Chemokines and diseases. European Journal of Dermatology 13:224-230 (2003).
Draft Guidance for Industry on Topical Dermatological Drug Product NDA's and ANDA's-In Vivo Bioavailability, Bioequivalence, in Vitro Release and Associated Studies: Dermatopharmacokinetics (DPK) Method Issues, http://srpub.pharma.org/letters/08.17.98.topical.derm.html. PRMA 1998.
Dreher et al. Colorimetric Method For Quantifying Human Stratum Corneum Removed by Adhesive Tape Stripping. Acta Derma Venereol (Stockholm) 78:186-189 (1998).
D-SQUAME from Cu-DEM (2003).
Dulmage et al. Lessons learned from gene expression profiling of cutaneous T-cell lymphoma. Br J Dermatol 169(6):1188-97 (2013).
Duncan et al. Melastatin expression and prognosis in cutaneous malignant melanoma. Journal of Clinical Oncology 19(2):568-576 (2001).
Eads et al. MethyLight: a high-throughput assay to measure DNA methylation. Nucleic Acid Res. 28:e32 (2000).
Easty et al. Up-regulation of ephrin-A1 during melanoma progression. Int. J. Cancer 84:494-501 (1999).
Edelman et al. Analysis of sample set enrichment scores: assaying the enrichment of sets of genes for individual samples in genome-wide expression profiles. Bioinformatics 22(14):e108-116 (2006).
Efron et al. Empirical hayes methods and false discovery rates for microarrays. Genet Epidemiol 23(1):70-86 (2002).

(56) References Cited

OTHER PUBLICATIONS

Elder. Precursors to melanoma and their mimics: nevi of special sites. Modern Pathology 19:s4-s20 (2006).
Elwood et al., Melanoma and sun exposure: an overview of published studies. International Journal of Cancer 73(2):198-203 (1997).
Emanuele et al. Anti-inflammatory effects of a topical preparation containing nicotinamide, retinol, and 7-dehydrocholesterol in patients with acne: a gene expression study. Clin Cosmet Investig Dermatol. 2012. 5:33-37.
Enard et al. Intra- and Interspecific Variation in Primate Gene Expression Patterns. Science 296:340-343 (2002).
Esquela-Kerscher et al., Oncomirs-microRNAs with a role in cancer. Nat Rev Cancer 6(4):259-69 (2006).
Fackler et al. Quantitative multiplex methylation-specific PCR analysis doubles detection of tumor cells in breast ductal fluid. Clin. Cancer Res. 12(11 Pt 1):3306-3310 (2006).
Fackler et al. Quantitative multiplex methylation-specific PCR assay for the detection of promoter hypermethylation in multiple genes in breast cancer. Cancer Res. 64(13):4442-4452 (2004).
Farage et al. Further Development of Noninvasive Method for Assessing Human Skin Irritation, Abstract # 1909, The Proctor & Gamble Company, (1998).
Feghali et al. Cytokines in acute and chronic inflammation. Front Biosci 2:d12-26 (1997).
Ferris et al. Impact on clinical practice of a non-invasive gene expression melanoma rule-out test: 12-month follow-up of negative test results and utility data from a large US registry study. Dermatology Online J 25(5):pii (May 2019).
Ferris et al. Noninvasive analysis of high-risk driver mutations and gene expression profiles in primary cutaneous melanoma. J Invest Dermatol 139:1127-1134 (2019).
Ferris et al. Real-world performance and utility of a noninvasive gene expression assay to evaluate melanoma risk in pigmented lesions. Melanoma Res 28(5):478-482 (2018).
Ferris et al. Utility of a noninvasive 2-gene molecular assay for cutaneous melanoma and effect on the decision to biopsy. JAMA Dermatol 153(7):675-680 (2017).
Flier et al. The CXCR3 activating chemokines IP-10, Mig, and IP-9 are expressed in allergic but not in irritant patch test reactions. J Invest Dermatol 113(4):5740-5748 (1999).
Fray et al. A potent, selective inhibitor of matrix metalloproteinase-3 for the topical treatment of chronic dermal ulcers. J Med Chem 46(16):3514-3525 (2003).
Freedberg et al. Keratins and the Keratinocyte Activation Cycle. The Journal of Investigative Dermatology 116(5):633-640 (2001).
Frommer et al. A genomic sequencing protocol that yields a positive display of 5- methylcytosine residues in individual DNA strands. PNAS USA 89:1827-1831 (1992).
Galiegue et al. Exploitation of expression profiles: examples in oncology. J Soc Biol 196(4):313-315 (2002).
Garcia-Sancha et al. MicroRNA Dysregulation in Cutaneous Squamous Cell Carcinoma (Review). Int. J. Mol. Sci. 20:2181 (2019).
Garofano et al. Comparison of Powerplex® 16 System and Other Multiplex STR Typing Kits on Casework, (Reporto Carabinieri Investigazioni Scientifiche, Parma, Italia.), 2000. Reference available at: http://www. promeea.com/eeneticidproc/ussvmp11proc/default.htm.
Garofano et al. PCR based analysis of epidermal cells found on adhesive tape, Advances in Forensic Haemogenetic, 6:281-283. (Istituto di Anatomia e Fisiologia Umana, Universita degli Studi ti Torino, Italy) (1996).
Garrett et al Tired of the same old grind in the new genomics and proteomics era? Targets Innovations in Genomics & Proteomics 1(5):156-162 (2002).
Gebhard et al. Genome-wide profiling of CpG methylation identifies novel targets of aberrant hypermethylation in myeloid leukemia. Cancer Res. 66:6118-6128 (2006).
Gebhard et al. Rapid and sensitive detection of CpG-methylation using methyl-binding (MB)-PCR. Nucleic Acids Res. 34:e82 (2006).
Genecard (www.genecards.org)—Accessed Nov. 11, 2009.
Gerami et al. Development and validation of a noninvasive 2-gene molecular assay for cutaneous melanoma. J Am Acad Dermatol 76(1):114-120.e2 (2017).
Gerami et al. Development of a novel noninvasive adhesive patch test for the evaluation of pigmented lesions of the skin. J Am Acad Dermatol 71(2):237-244 (2014).
Germai et al. Development and Validation of a Noninvasive 2-gene Molecular Assay for 'Cutaneous Melanoma. J Am Acad Dermatol 76(1):114-120 (2016).
Gerritsen et al. Repeated tape stripping of normal skin: a histological assessment and comparison with events seen in psoriasis. Arch Dermatol Res., 286(8):455-461 (1994).
Gershenwald et al. Gene expression profiling of human cutaneous melanoma: are we there yet? Cancer Biol Ther 3(1):121-123 (2004).
Ghali et al. Epidermal and Hair Follicle Progenitor Cells express Melanoma-Associated Chondroitin Sulfate Proteoglycan Core Protein. Journal of Investigative Dermatology 122:433-442 (2004).
Gibson et al. A Novel Method for Real Time Quantitative RT-PCR. Genome Research 6:995-1001 (1996).
Gloster et al. The epidemiology of skin cancer. Dermatol Surg. 22(3):217-226 (1996).
Goldschmidt et al. Desquamation of the Human Horny Layer. Archives of Dermatology 95:583-586 (1967).
Gong et al. MiRNA-221 promotes cutaneous squamous cell carcinoma progression by targeting PTEN. Cell Mol Biol Lett. 24:9 (2019).
Gonzalgo et al. Rapid quantitation of methylation differences at specific sites using methylation-sensitive single nucleotide primer extension (Ms-SNuPE). Nucleic Acids Res. 25:2529-2531 (1997).
Graengsjoe et al. Different Pathways in Irritant Contact Eczema? Early Differences in the Epidermal Elemental Content and Expression of Cytokines After Application of 2 Different Irritants. Contact Dermatitis 35(6):355-360 (1996).
Graham. Basic Pathologic Changes in Skin, in Dermal Pathology, Wd. J H Graham, W C Johnson, and E B Helwig, Harper-Row, Hagerstown, MD, pp. 119-135 (1972).
Grammatico et al. Involvement of the 4q21 region in human malignant melanomas: cytogenic and immunocytochemical characterization of three primary cell cultures. World. J. of Surgery 19:350-351 (1995).
Grangsjo et al. Different Pathways in Irritant Contact Eczema? Early Differences in the Epidermal Elemental Content and Expression of Cytokines after Application of 2 Different Irritants. Contact Dermatitis 35:355-360 Munksgaard, Denmark (1996).
Granstein. New Treatments for Psoriasis. The New England Journal of Medicine 345(4):284-287 (2001).
GRO1. Cancer Genetics Web. (www.cancer-genetics.org) 2 pages (2003).
Gyorffy et al. A web-based data warehouse on gene expression in human malignant melanoma. Journal of Investigative Dermatology 127:394-399 (2007).
Hamid et al. In Vivo Expression of IL-12 and IL-13 in Atopic Dermatitis. Journal of Allergy and Clinical Immunology 98(l):1-8 (1996).
Hammond MicroRNAs as oncogenes. Curr Opin Genet Dev 16(1):4-9 (2006).
Haqq et al. The gene expression signatures of melanoma progression. PNAS USA 102(17):6092-6097 (2005).
Harris et al. Single-molecule DNA sequencing of a viral genome. Science 320:106-109 (2008).
Haskill et al. Identification of three related human GRO genes encoding cytokine functions. PNAS 87:7732-7736 (1990).
Hatfield et al. Differential analysis of DNA microarray gene expression data. Mol. Microbiol. 47(4):871-877 (2003).
Heaton et al. Surgical margins and prognostic factors in patients with thick (>4mm) primary melanoma. Ann Surg Oncol 5:322-328 (1998).
Heid et al. Real Time Quantitative PCR. Genome Research 6:986-994 (1996).
Herman et al. Gene silencing in cancer in association with promoter hypermethylation. N Engl J Med 349(21):2042-2054 (2003).

(56) References Cited

OTHER PUBLICATIONS

Herman et al. Methylation-specific PCR: a novel PCR assay for methylation status of CpG islands. PNAS USA 93:9821-9826 (1996).
Herouy. Matrix metalloproteinases in skin pathology (Review). Int J Mol Med 7(1):3-12 (2001).
Hirao et al. Elevation of Interleukin 1 Receptor Antagonist in the Stratum Corneum of Sun-Exposed and Ultraviolet B-Irradiated Human Skin. The Journal of Investigative Dermatology 106(5):1102-1107 (1996).
Hodson et al. In situ PCR for visualization of microscale distribution of specific genes and gene products in prokaryotic communities. Applied and environmental microbiology 61(11):4074-4082 (1995).
Hoefakker et al. In vivo Cytokine Profiles in Allergic and Irritant Contact Dermatitis. Contact Dermatitis 33:258-266 Munksgaard, Denmark (1995).
Hoffrage et al. Communicating Statistical Information. Science 290(5500):2261-2262 (2000).
Hojyo-Tomoka et al. Does Cellophane Tape Stripping Remove the Horny Layer? Archives of Dermatology 106(5):767-768 (1972).
Holland et al. Detection of specific polymerase chain reaction product by utilizing the 5'----3' exonuclease activity of Thermus aquaticus DNA polymerase. PNAS USA 88(16):7276-7280 (1991).
Holleran et al. Regulation of epidermal sphingolipid synthesis by permeability barrier function. J. Lipid Research 32:1151-1158 (1991).
Horak et al. ChIP-chip: a genomic approach for identifying transcription factor binding sites. Methods Enzymol 350:469-483 (2002).
Hornberger et al. Clinical and economic implications of a noninvasive molecular pathology assay for early detection of melanoma. JAMA Dermatol 154(9):1-8 (2018).
Howie et al. Epidermal keratinocyte production of interferon-gamma immunoreactive protein and mRNA is an early event in allergic contact dermatitis. Journal of Investigative Dermatology 106(6):1218-1223 (1996).
Hu et al. MicroRNA-186 promotes cell proliferation and inhibits cell apoptosis in cutaneous squamous cell carcinoma by targeting RETREG1. Expt. Therapeutical Medicine 17:1930-1938 (2019).
Huang et al. Highly Recurrent TERT Promoter Mutations in Human Melanoma. Science 339:957-959 (2013).
Hung et al. Global gene expression profiling in Escherichia coli K12: The effects of leucine-responsive regulatory protein. J. Biol. Chem. 277(43):40309-40323 (2002).
Ichinose. Physiopathology and regulation of factor XIII. Thromb Haemost 86(1):57-65 (2001).
Instructions for use DermTech adhesive skin biopsy kit. DermTech. Available at http://dermtech.com/wp-content/uploads/2015/10/dermtech-ifu-skin-collection-v7.pdf (Revised data Oct. 2015) (1 pg.).
Iorio et al. MicroRNA gene expression deregulation in human breast cancer. Cancer Res 65(16):7065-7070 (2005).
Itoh et al. Generation of 3D skin equivalents fully reconstituted from human induced pluripotent stem cells (iPSCs). PLoS One 8(10):e77673 (2013).
Itzkowitz et al. Improved fecal DNA test for colorectal cancer screening. Clin Gastroenterol. Hepatol. 5(1):111-117 (2007).
Jansen et al. Gene expression analysis differentiates melanomas from Spitz nevi. J Drugs Dermatol 17(5):574-576 (2018).
Jemal et al. Cancer statistics. CA Cancer J Clin 2003. 53(1):5-26 (2003).
Jovanovic. Molecular studies of melanoma. Archive of Oncology 13:75-77 (2005).
Junghans et al. Epidermal Cytokines IL-IB, TNF-a, and IL-12 in Patients with Atopic Dermatitis: Response to Application of House Dust Mite Antigens. The Journal of Investigative Dermatology 111(6):1184-1188 (1998).
Kahari et al. Matrix metalloproteinases in skin. Exp Dermatol 6(5):199-213 (1997).
Kalia et al. Homogeneous transport in a heterogeneous membrane: water diffusion across human stratum corneum in vivo. Biophys J 71(5):2692-2700 (1996).
Kallioniemi. Biochip technologies in cancer research. Ann Med. Mar. 33(2):142-147 (2001).
Katerinaki et al. TNF-alpha increases human melanoma cell invasion and migration in vitro: the role of proteolytic enzymes. British Journ of Cancer 89:1123-1129 (2003).
Katz et al. Skin surface touch print for diagnosing fungal infections. American Family Physician 31(4):189-194 (1985).
Kawada et al. Processing of cathepsins L, B and D in psoriatic epidermis. Arch Dermatol Res 289(2):87-93 (1997).
Keppler, D. Towards novel anti-cancer strategies based on cystatin function. Cancer Letters 235(2):159-176 (2006).
Kerkhoff et al. The regulatory role of MRP8 (S100A8) and MRP14 (S100A9) in the transendothelial migration of human leukocytes. Pathobiology 67(5-6):230-232 (1999).
Kilpatrick. Animal lectins: a historical introduction and overview. Biochim Biophys Acta 1572(2-3):187-197 (2002).
Kim et al. Epigenomic Profiling Reveals Novel and Frequent Targets of Aberrant DNA Methylation-Mediated Silencing in Malignant Glioma. Cancer Research 66(15):7490-7501 (2006).
Kim et al. The promise of microarray technology in melanoma care. Cancer Contro. 9(1):49-53 (2002).
Klaschka et al. Individual Transparency Patterns of Adhesive-tape Strip Series of the Stratum Corneum. International Journal of Dermatology 16(10):836-841 (1977).
Klaschka et al. New Measuring Device of Horny Layer Transparency. Archives of Dermatology 254:313-325 (1975).
Koga et al. Genome-wide screen of promoter methylation identifies novel markers in melanoma. Genome Res. 19:1462-1470 (2009).
Kohnken et al. MicroRNAs in Cutaneous T-Cell Lymphoma: The Future of Therapy. J Invest Dermatol. 139(3):528-534 (2019).
Komine et al. Interleukin-1 induces transcription of keratin K6 in human epidermal keratinocytes. J Invest Dermatol 116(2):330-338 (2001).
Komine et al. Regulation of epidermal expression of keratin K17 in inflammatory skin diseases. J Invest Dermatol 107(4):569-575 (1996).
Kondo et al. Characterization of Epidermal Cytokine Profiles in Sensitization and elicitation Phases of Allergic Contact dermatitis as well as Irritant Contact dermatitis in Mouse skin. Lymphokine and Cytokine Res. 13(6):367-375 (1994).
Kong et al. A multivariate approach for integrating genome-wide expression data and biological knowledge. Bioinformatics 22(19):2373-2380 (2006).
Koning et al.T Cell Subsets and Cytokines in Allergic and Non-allergic Children. I. Analysis of IL-4 IFN-gamma and IL-13 mRNA Expression and Protein Production. Cytokine 9(6):416-426 (1997).
Krasteva. Contact dermatitis. Int. Dermatol. 32:547-560 (1993).
Kricker et al., Sun exposure and non-melanocytic skin cancer. Cancer Causes & Control 5(4):367-392 (1994).
Kroese et al. Genetic tests and their evaluation: Can we answer the key questions? Genetics in Medicine 6:475-480 (2004).
Kupper. Production of Cytokines by Epithelial Tissues.Am. J Dermatopathol. 11:69-73 (1993).
Lacroix et al. A low-density DNA microarray for analysis of markers in breast cancer. Int J Biol Markers 17(1):5-23 (2002).
Landegren et al. A ligase-mediated gene detection technique. Science 241:1077-1080 (1988).
Landegren et al. DNA Diagnostics—Molecular Techniques and automation. Science, 242:229-237 (1988).
Lee et al. The C. elegans heterochronic gene lin-4 encodes small RNAs with antisense complementarity to lin-14. Cell 75:843-854 (1993).
Lendeckel et al. Synergistic action of DPIV and APN in the regulation of T cell function. Adv Exp Med Biol 524:123-131 (2003).
Lener et al. Expression profiling of aging in the human skin, Experimental Gerontology, 41:387-397 (2006).
Li et al. Model-based analysis of oligonucleotide arrays: expression index computation and outlier detection. PNAS USA 98(1): 31-36 (2001).

(56) References Cited

OTHER PUBLICATIONS

Lieb. Genome-wide mapping of protein-DNA interactions by chromatin immunoprecipitation and DNA microarray hybridization. Methods Mol Biol 224:99-109 (2003).

Lindahl et al., Quality control by DNA repair. Science 286(5446):1897-1905 (1999).

Liotta et al. Molecular profiling of Human Cancer, Nature Reviews/ Genetics 1:48-56 (2000).

Litvinov et al. Gene expression analysis in Cutaneous T-Cell Lymphomas (CTCL) highlights disease heterogeneity and potential diagnostic and prognostic indicators. Oncoimmunology 6(5):e1306618 (2017).

Litvinov et al., The Use Of Transcriptional Profiling To Improve Personalized Diagnosis And Management Of Cutaneous T-Cell Lymphoma (CTCL). Clin Cancer Res. 21(12):2820-2829 (2015).

Liu et al. Epidermal Genetic Information Retrieval is a non-invasive method of evaluating message (mRNA) profiles of lesional versus non-lesional skin of psoriatic subjects before and after initiations of therapy. J Investigative Dermatology. 122:A54 Abstract 323 (2004).

Liu et al. Inhibition of p38 MAPK signaling augments skin tumorigenesis via NOX2 driven ROS generation. PLoS One 9(5):e97245 (2014).

Livak et al. Analysis of Relative Gene Expression Data Using RealTime Quantitative PCR and the 2-delta delta Ct Method. Methods 25:402-408 (2001).

Ljland et al. Expression of Angiogenic and Immunosuppressive Factors by Uveal Melanoma Cell Lines, Melanoma Research, 9:445-450 (1999).

Lobmann et al. Expression of matrix-metalloproteinases and their inhibitors in the wounds of diabetic and non-diabetic patients. Diabetologia 45(7): 1011-1016 (2002).

Long et al. Improved statistical inference from DNA microarray data using analysis of variance and a Bayesian statistical framework. Analysis of global gene expression in *Escherichia coli* K12. J. Biol. Chem. 276(23): 19937-19944 (2001).

Lu et al. MicroRNA expression profiles classify human cancers. Nature, 435(7043):834-838 (2005).

Lucas et al. Massive inflammatory syndrome and lymphocytic immunodeficiency in KARAP/DAP12-transgenic mice. Eur J Immunol 32(9):2653-2663 (2002).

Lucentini, J. Gene Association Studies Typically Wrong. The Scientist, 18(24):20 (2004).

Maddox et al. Elevated serum levels in human pregnancy of a molecule immunochemically similar to eosinophil granule major basic protein.J. Exp. Med. 158:1211-1226 (1983).

Mardis. Next-generation DNA sequencing methods. Annu. Rev. Genomics Hum. Genet. USA 9:387-402 (2008).

Margulies et al. Genome sequencing in microfabricated high-density picolitre reactors. Nature 437:376-380 (2005).

Marin et al., Molluscan shell proteins: primary structure, origin, and evolution. Current Topics in Developmental Biology 80:209-276 (2007).

Marionnet et al. Modulation of gene expression induced in human epidermis by environmental stress in vivo. J Invest Dermatol 121(6):1447-1458 (2003).

Marttin et al. A Critical Comparison of Methods to Quantify Stratum corneum removed by Tape Stripping. Skin Pharmacology 9:69-77 (1996).

Maxam et al. A new method for sequencing DNA. PNAS USA 74(2):560-564 (1977).

May et al. How Many Species are there on Earth? Science 241:1441-1449 (1988).

McCarty et al. Epidermal hyperplasia overlying human melanoma correlates with tumour depth and angiogenesis. Melanoma Res 13(4):379-387 (2003).

McKenzie et al. Interleukin-1 receptor antagonist inhibits subcutaneous B16 melanoma growth in vivo. Anticancer Research 16(1):437-441(1996).

McLean et al. Pharmacogenomic Analysis of Cytogenetic Response in Chronic Myeloid Leukemia Patients Treated with Imatinib. Clinical Cancer Research 10(1):155-165 (2004).

Melen et al. Human MxB protein, an interferon-alpha-inducible GTPase, contains a nuclear targeting signal and is localized in the heterochromatin region beneath the nuclear envelope. J Biol Chem 271(38):23478-23486 (1996).

Melt. Total Nucleic Acid Isolation System. Thermo Fisher Scientific, Part No. AM1983, P/N 1983M Revision D, 27. Retrieved from the Internet:< https://assets.thermofisher.com/TFS-Assets/LSG/manuals/cms_058167.pdf> on Jun. 2, 2018 (Oct. 2008) (pp. 1-31).

Merola et al. Non-invasive tape sampling reveals a type I interferon RNA signature in cutaneous lupus erythematosus that distinguishes affected from unaffected and healthy volunteer skin. J Investigative Dermatology 138(5): Abstract 1096 (2018).

Mehul et al. Proteomic analysis of stratum corneum in Cutaneous T-Cell Lymphomas and psoriasis. Exp Dermatol 28(3):317-321 (2019).

Michael et al. Reduced accumulation of specific microRNAs in colorectal neoplasia. Mol Cancer Res. 1(12):882-891 (2003).

Mitchell et al. Global analysis of cellular transcription following infection with an HIV-based vector. Mol Ther 8(4):674-687 (2003).

Miyashiro et al. Molecular strategy for detecting metastatic cancers with use of multiple tumor-specific MAGE-A genes. Clinical Chemistry 47(3):505-512 (2001).

Mok. The Jakinibs in systemic lupus erythematosus: progress and prospects. Expert Opin Investig Drugs. 28(1):85-92 (2019).

Molhuizen et al. Structural, biochemical, and cell biological aspects of the serine proteinase inhibitor SKALP/elafin/ESI. Biol Chem Hoppe Seyler 376(1):1-7 (1995).

Morhenn et al. A noninvasive method for quantifying and distinguishing inflammatory skin reactions. Journal of the American Academy of Dermatology 41(5 Pt 1):687-692(1999).

Muller-Decker et al. Arachidonic acid metabolism in primary irritant dermatitis produced by patch testing of human skin with surfactants. Toxicol Appl Pharmacol 153(1):59-67 (1998).

Muller-Decker et al. Keratinocyte-derived proinflammatory key mediators and cell viability as in vitro parameters of irritancy: a possible alternative to the Draize skin irritation test. Toxicol Appl Pharmacol 127(1):99--108 (1994).

Muthusamy et al. Epigenetic Silencing of Novel Tumor Suppressors in Malignant Melanoma. Cancer Research 66(23):11187-11193 (2006).

Nair et al. Virus-encoded microRNAs: novel regulators of gene expression. Trends Microbiol. 14(4):169-175 (2006).

NCBI Geo Profiles Database, DataSet Record GDS1989, excerpts (2 pages), Apr. 2006.

Nickoloff et al. Keratinocyte Interleukin-10 Expression is Upregulated in Tape-Stripped Skin, Poison Ivy Dermatitis, and Sezary Syndrome, but Not in Psoriatic Plaques. Clinical Immunology and Immunopathology 73(I):63-68 (1994).

Nickoloff et al. Perturbation of epidermal barrier function correlates with initiation of cytokine cascade in human skin. Journal of the American Academy of Dermatology 30(4):535-546 (1994).

Nikkola et al. High Expression Levels of Collagenase-1 and Stromelysin-1 Correlate with Shorter Disease-Free Survival in Human Metastatic Melanoma. Int. J. Cancer 97:432-438 (2002).

Nurmi et al. High-performance real-time quantitative RT-PCR using lanthanide probes and a dual-temperature hybridization assay. Analytical Chemistry 74(14) 3525-3532 (2002).

O'Geen et al. Comparison of sample preparation methods for ChIP-chip assays. BioTechniques 41(5):577-580 (2006).

Ohmen et al. Overexpression of IL-10 in Atopic Dermatitis. The Journal of Immunology 154:1956-1963 (1995).

Olek et al. The pre-implantation ontogeny of the H19 methylation imprint Nat. Genet. 17(3):275-276 (1997).

Onodera et al. Macrophage migration inhibition factor up-regulates expression of matrix metalloproteinases in synovial fibroblasts of rheumatoid arthritis. J. Biol. Chem 275:444--450 (2000).

Orro et al., Development of TAP, a non-invasive test for qualitative and quantitative measurements of biomarkers from the skin surface. Biomarker Research 2: 20 doi: 10.1186/2050-7771-2-20 [1-12] (2014).

(56) References Cited

OTHER PUBLICATIONS

Page et al. The Power Atlas: a power and sample size atlas for microarray experimental design and research. BMC Bioinformatics 7:84 (2006).
Paik et al. A multigene assay to predict recurrence of tamoxifen-treated, node-negative breast cancer. N Eng J Med 351(27):2817-2826 (2004).
Paludan et al. Use of the Polymerase Chain Reaction in Quantification of Interleukin 8 mRNA in Minute Epidermal Samples. Journal of Investigative Dermatology 99:830--835 (1992).
Pang et al. Pathway analysis using random forests classification and regression. Bioinformatic 22(16):2028-2036 (2006).
Pavey et al. Microarray expression profiling in melanoma reveals a BRAF mutation signature. Oncogene 23(23):4060-4067 (2004).
PCT/US1999/19012 International Preliminary Examination Report dated May 26, 2000.
PCT/US1999/19012 International Search Report dated Jan. 31, 2000.
PCT/US2002/20728 International Preliminary Examination Report dated Feb. 2, 2005.
PCT/US2002/20728 International Search Report dated Oct. 27, 2003.
PCT/US2005/10911 International Preliminary Report on Patentability dated Oct. 4, 2006.
PCT/US2005/10911 International Search Report dated Nov. 18, 2005.
PCT/US2005/10911 Written Opinion dated Nov. 18, 2005.
PCT/US2007/009686 International Preliminary Report on Patentability dated Oct. 22, 2008.
PCT/US2007/009686 International Search Report and Written Opinion dated Dec. 18, 2007.
PCT/US2008/062545 International Preliminary Report on Patentability dated Nov. 10, 2009.
PCT/US2008/062545 International Search Report dated Sep. 18, 2008.
PCT/US2008/062545 Written Opinion dated Sep. 18, 2008.
PCT/US2009/055327 International Preliminary Report on Patentability dated Mar. 10, 2011.
PCT/US2009/055327 International Search Report dated Jan. 7, 2010.
PCT/US2009/44035 International Search Report and Written Opinion dated Sep. 3, 2009.
PCT/US2014/035336 International Search Report and Written Opinion dated Sep. 2, 2014.
PCT/US2014/044588 International Search Report and Written Opinion dated Oct. 20, 2014.
PCT/US2015/41599 International Search Report and Written Opinion dated Oct. 28, 2015.
PCT/US2016/30287 International Search Report and Written Opinion dated Aug. 16, 2016.
PCT/US2018/026902 International Search Report and Written Opinion dated Jul. 19, 2018.
PCT/US2019/018102 International Search Report and Written Opinion dated Jul. 1, 2019.
PCT/US2019/018102 Invitation to Pay Additional Fees dated May 9, 2019.
PCT/US2019/031203 International Invitation to Pay Additional Fees dated Jul. 11, 2019.
PCT/US2019/031203 International Search Report and Written Opinion dated Aug. 29, 2019.
PCT/US2020/026339 International Search Report and Written Opinion dated Jun. 16, 2020.
PCT/US2020/24469 International Search Report and Written Opinion dated Jun. 19, 2020.
Pelizzola et al. MEDME: an experimental and analytical methodology for the estimation of DNA methylation levels based on microarray derived MeDIP-enrichment. Genome Res. 18:1652-1659 (2008).
Perkins et al. A Noninvasive Method to Assess Skin Irritation and Compromised Skin Conditions Using Simple Tape Adsorption of Molecular Markers of Inflammation. Skin Res. Technol. 7(4):227-237 (2001).
Perkins et al. A non-invasive tape absorption method for recovery of inflammatory mediators to differentiate normal from compromised scalp conditions. Skin Res Technol 8(3):187-193 (2002).
Perkins et al. Development of a Noninvasive Method for Assessing Human Skin Irritation. The Toxicologist 36(1):365 (1997).
Petit-Zeman. MicroRNAs hit the big time. Nat Rev Drug Discov. 5(1):5 (2006).
Phan et al. Role of the C-terminal propeptide in the activity and maturation of gamma $\gamma$-interferon-inducible lysosomal thiol reductase (GILT). PNAS USA 99(19):12298-12303 (2002).
Pilcher et al. Role of matrix metalloproteinases and their inhibition in cutaneous wound healing and allergic contact hypersensitivity. Ann N Y Acad Sci 878:12-24 (1999).
Pistoor et al. Novel Predictive Assay for Contact Allergens Using Human Skin Explant Cultures, American Journal of Pathology 149(1):337-343 (1996).
Potts et al. Physical Methods for Studying Stratum Corneum Lipids, Seminars in Dermatology 11(2):129-138 (1992).
Prasad et al. Differential expression of degradome components in cutaneous squamous cell carcinomas. Mod Pathol 27(7):945-957 (2014).
Preston et al., Nonmelanoma cancers of the skin. New England Journal of Medicine 327(23):1649-1662 (1992).
Rauch et al. High-resolution mapping of DNA hypermethylation and hypomethylation in lung cancer. PNAS USA 105:252-257 (2008).
Raval et al. Loss of expression of tropomyosin-1, a novel class II tumor suppressor that induces anoikis, in primary breast tumors. Oncogene 22(40):6194-6203 (2003).
Rein et al. Identifying 5-methylcytosine and related modifications in DNA genomes. Nucleic Acids Res. 26(10):2255-2264 (1998).
Reinhart et al. The 21-nucleotide let-7 RNA regulates developmental timing in Caenorhabditis elegans. Nature 403(6772):901-906 (2000).
Ressler et al. p16INK4A is a robust in vivo biomarker of cellular aging in human skin. Aging Cell 5(5):379-389 (2006).
Rittie et al. UV-light-induced signal cascades and skin aging. Ageing Research Reviews 1:705-720 (2002).
Rivers et al. Non-invasive gene expression testing to rule out melanoma. Skin Therapy Letter 23(5):1-4 (2018).
Rivers et al. Ruling out Melanoma: A practical guide to improving performance through non-invasive gene expression testing. Skin Therapy Letter: Family Practice Edition 14(1):4-6 (2019).
Roberson et al., Psoriasis genetics: breaking the barrier. Trends in Genetics 26(9):415-423 (2010).
Rosenthal et al., Ultraviolet B light induces rapid changes in gene expression as detected by non-invasive, adhesive skin biopsies. [Poster Presentation, Orlando Florida] (Jun. 2019).
Rougier et al. In Vivo Correlation Between Stratum Corneum Reservoir Function and Percutaneous Absorption. J. Investigative Dermatology 81:275-278 (1983).
Rougier et al. In Vivo Percutaneous Penetration of Some organic Compounds Related to Anatomic Site in Humans: Predictive Assessment by the Stripping Method. J. Pharmaceutical Sciences 76:451-454 (1987).
Rougier et al. Regional variation in percutaneous absorption in man: measurement by the stripping method. Arch Dermatol Res. 278(6):465-469 (1986).
Rougier et al. The measurement of the stratum corneum reservoir. A predictive method for in vivo percutaneous absorption studies: influence of application time. J Invest Dermatol. 84(1):66-68 (1985).
Rowe et al. Interleukin-4 and the Interleukin-4 Receptor in Allergic Contact Dermatitis. Contact Dermatitis 38(1):36-39 (1998).
Rudert. Genomics and proteomics tools for the clinic. Curr Opin. Mol. Ther.2(6):633-642 (2000).
Ryan et al. Cytokine mRNA Expression in Human Epidermis After Patch Treatment with Rhus and Sodium Lauryl Sulfate. American Journal of Contact Dermatitis 10(3):127-135 (1999).

(56) References Cited

OTHER PUBLICATIONS

Sadri et al. Rapid analysis of DNA methylation using new restriction enzyme sites created by bisulfite modification. Nucleic Acids Res. 24:5058-5059 (1996).
Saiki et al. A Novel Method For The Detection of Polymorphic Restriction Sites By Cleavage of Oligonucleotide Probes: Application To Sickle-Cell AnemiaBioTechnology 3:1008-1012 (1985).
Saito-Hisaminato et al. Genome-wide profiling of gene expression in 29 normal human tissues with a cDNA microarray. DNA Res 9:35-45 (2002).
Samal et al. Cloning and characterization of the cDNA encoding a novel human pre-B-cell colony-enhancing factor. Mol Cell Biol 14(2):1431--1437 (1994).
Sander et al. Expression of extracellular matrix protein 1 (ECM1) in human skin is decreased by age and increased upon ultraviolet exposure. Br J Dermatol 154(2):218-224 (2006).
Sanger et al. DNA sequencing with chain-terminating inhibitors. PNAS USA 74(12):5463-5467 (1977).
Satagopan et al. A statistical perspective on gene expression data analysis. Stat Med 22(3):481-499 (2003).
Schauberger et al. Development of a non-invasive method of RNA collection in children with atopic dermatitis. J Allergy Clin Immunol. 139(2):AB239, No. 751 (2017).
Seftor et al. Cooperative interactions of laminin 5 gamma2 chain, matrix metalloproteinase-2, and membrane type-1-matrix/metalloproteinase are required for mimicry of embryonic vasculogenesis by aggressive melanoma. Cancer Res 61(17):6322-6327 (2001).
Shattuck et al. MGSA/GRO transcription is differentially regulated in normal retinal pigment epithelial and melanoma cells. Molecular and Cellular Biology 14(1):791-802 (1994).
Shen et al., Epigenetic and genetic dissections of UV-induced global gene dysregulation in skin cells through multi-omics analyses. Scientific Reports 7:42646 (2017).
Shen et al., Transcriptome analysis identifies the dysregulation of ultraviolet target genes in human skin cancers. PLoS One 11(9):e0163054 [1-14] (2016).
Shin et al. Lesional gene expression profiling in cutaneous T-cell lymphoma reveals natural clusters associated with disease outcome. Blood 110(8):3015-3027 (2007).
Shintani et al. Growth-Regulated Oncogene-1 Expression is Associated with Angiogenesis and Lymph Node Metastasis in Human Oral Cancer. Oncology 66:316-322 (2004).
Shiraishi et al. Isolation of DNA fragments associated with methylated CpG islands in human adenocarcinomas of the lung using a methylated DNA binding col. and denaturing gradient gel electrophoresis. PNAS USA 96(6):2913-2918 (1999).
Si et al. Expression of the Neuroglandular Antigen and Analogues in Melanoma. CD9 Expression Appears Inversely Related to Metastatic Potential of Melanoma. Int. J. Cancer 54:37-43 (1993).
Siegel et al. Further consideration of the pigmented lesion assay-reply. JAMA Dermatol 155(3):393-394 (2019).
Slack et al. MicroRNAs as a potential magic bullet in cancer. Future Oncol. 2(1):73-82 (2006).
Slas. From Laboratory to Clinic: Novel Skin Sampling Technique Simplifies Disease Detection. Available at https://www.slas.org/eln/from-laboratory-to-clinic-novel-skin-sampling-technique-simplifies-disease-detection/ (2012).
Smyth et al. Statistical issues in eDNA microarray data analysis. Methods Mol Biol 224:111-136 (2003).
Soni et al. Progress toward ultrafast DNA sequencing using solid-state nanopores. Clin. Chem. 53:1996-2001 (2007).
Soufir et al. Association Between Endothelin Receptor B Nonsynonymous Variants and Melanoma Risk. Journ. Nat'l. Cancer Inst. 97(17):1297-1301 (2005).
Stege et al., Enzyme plus light therapy to repair DNA damage in ultraviolet-B-irradiated human skin. Proceedings of the National Academy of Sciences 97(4):1790-1795 (2000).
Steinert et al., Small proline-rich proteins are cross-bridging proteins in the cornified cell envelopes of stratified squamous epithelia. Journal of Structural Biology 122(1-2):76-85 (1998).
Stevens et al. Disease-associated KIF3A variants alter gene methylation and expression impacting skin barrier and atopic dermatitis risk. Nature Communications 11:4092 (2020).
Stoddard et al., Improvement of actinic keratoses using topical DNA repair enzymes: a randomized placebo-controlled trial. Journal of Drugs in Dermatology: JDD 16(10):1030-1034 (2017).
Stolz et al. Semiquantitative analysis of histologic criteria in thin malignant melanomas. J Am Acad Dermato. 20(6):1115-1120 (1989).
Stuart et al. In silico dissection of cell-type-associated patterns of gene expression in prostate cancer. PNAS USA 101(2):615-620 (2004).
Su et al. Identification of tumor-suppressor genes using human melanoma cell lines UACC903, UACC903(+6), and SRS3 by comparison of expression profiles. Mol Carcinog 28(2):119-127 (2000).
Suzuki et al. Control selection for RNA quantitation. Biotechniques 29(2):332-337 (2000).
Syrokou et al. Synthesis and expression of mRNA encoding for different versican splice variants is related to the aggregation of human epithelial mesothelioma cells. Anticancer Res 22(6C):4157-4162 (2002).
Tagawa. A microRNA cluster as a target of genomi amplification in malignant lymphoma. Leukemia. 19(11):2013-2016 (2005).
Takashi et al. Novel melanoma antigen, FCRL/FREB, identified by cDNA profile comparison using DNA chip Are immunogenic in multiple melanoma patients. International Journal of Cancer 114(2):283-290 (2005).
Thatcher et al. miRNA Expression Analysis During Normal Zebrafish Development and Following Inhibition of the Hedgehog and Notch Signaling Pathways. Developmental Dynamics 236:2172-2180 (2007).
Thiele et al. Macromolecular carbonyls in human stratum corneum: a biomarker for environmental oxidant exposure? FEBS letters 422:403-406 (1998).
Thiele et al. Protein Oxidation in Human Stratum Corneum: Susceptibility of Keratins to Oxidation In Vitro and Presence of a Keratin Oxidation Gradient In Vivo. Journal of Investigative Dermatology 113:335-339 (1999).
Thoma F. Light and dark in chromatin repair: repair of UV-induced DNA lesions by photolyase and nucleotide excision repair. The EMBO Journal 18(23):6585-6598 (1999).
Thorey et al. The Ca2+-binding proteins S100A8 and S100A9 are encoded by novel injury-regulated genes. J Biol Chem 276(38):35818-35825 (2001).
Tibshirani et al. Diagnosis of multiple cancer types by shrunken centroids of gene expression. PNAS USA 99(10):6567-6572 (2002).
Tomic-Canic et al. Epidermal signal transduction and transcription factor activation in activated keratinocytes. J Dermatol Sci 17(3):167-181 (1998).
Torabian et al. Biomarkers for melanoma. Current Opinion in Oncology 17:167-171 (2005).
Torre et al. Epidermal Cells on Stubs Used for Detection of GSR with SEM-EDX: Analysis of DNA Polymorphisms. Journal of Forensic Sciences (JFSCA) 41(4):658-659 (1996).
Toyota et al. Identification of differentially methylated sequences in colorectal cancer by methylated CpG island amplification. Cancer Res. 59:2307-2312 (1999).
Tricarico et al. Quantitative real-time reverse transcription polymerase chain reaction: normalization to rRNA or single housekeeping genes is inappropriate for human tissue biopsies. Anal Biochem 309(2):293-300 (2002).
Ulfgren et al. An immunohistochemical analysis of cytokine expression in allergic and irritant contact dermatitis. Acta Derm Venereol 80(3):167-170 (2000).
U.S. Appl. No. 09/375,609 Office Action dated Dec. 18, 2003.
U.S. Appl. No. 09/375,609 Office Action dated Jan. 31, 2001.
U.S. Appl. No. 09/375,609 Office Action dated Jul. 12, 2001.
U.S. Appl. No. 09/967,658 Office Action dated Apr. 22, 2003.
U.S. Appl. No. 09/967,658 Office Action dated Jun. 6, 2003.
U.S. Appl. No. 09/970,617 Office Action dated Jun. 2, 2004.
U.S. Appl. No. 09/972,531 Office Action dated Jun. 14, 2004.
U.S. Appl. No. 09/976,356 Office Action dated Sep. 24, 2003.
U.S. Serial No. 09/976,361 Office Action dated Jun. 28, 2004.
U.S. Appl. No. 09/976,613 Office Action dated Jun. 28, 2004.

(56) References Cited

OTHER PUBLICATIONS

U.S. Appl. No. 10/184,846 Office Action dated May 5, 2005.
U.S. Appl. No. 10/184,846 Office Action dated Sep. 26, 2006.
U.S. Appl. No. 10/816,457 Office Action dated Mar. 13, 2006.
U.S. Appl. No. 10/816,457 Office Action dated Sep. 5, 2005.
U.S. Appl. No. 11/710,661 Office Action dated Jan. 11, 2010.
U.S. Appl. No. 11/710,661 Office Action dated Jul. 14, 2009.
U.S. Appl. No. 11/710,661 Office Action dated Jul. 21, 2010.
U.S. Appl. No. 11/788,644 Office Action dated Jul. 25, 2008.
U.S. Appl. No. 12/114,669 Office Action dated Aug. 5, 2010.
U.S. Appl. No. 12/114,669 Office Action dated Jan. 6, 2011.
U.S. Appl. No. 12/114,669 Office Action dated Jun. 21, 2011.
U.S. Appl. No. 12/114,669 Office Action dated Jun. 30, 2014.
U.S. Appl. No. 12/114,669 Office Action dated Nov. 17, 2009.
U.S. Appl. No. 12/114,669 Office Action dated Oct. 19, 2015.
U.S. Appl. No. 12/114,669 Office Action dated Oct. 27, 2014.
U.S. Appl. No. 12/550,060 Office Action dated Nov. 18, 2014.
U.S. Appl. No. 12/991,685 Office Action dated Mar. 13, 2013.
U.S. Appl. No. 12/991,685 Office Action dated Nov. 4, 2013.
U.S. Appl. No. 13/136,278 Office Action dated Mar. 14, 2012.
U.S. Appl. No. 13/136,278 Office Action dated Sep. 25, 2012.
U.S. Appl. No. 13/847,434 Office Action dated Jul. 29, 2015.
U.S. Appl. No. 13/847,434 Office Action dated Mar. 21, 2014.
U.S. Appl. No. 13/847,434 Office Action dated Nov. 18, 2014.
U.S. Appl. No. 13/847,434 Office Action dated Oct. 10, 2013.
U.S. Appl. No. 14/172,784 Office Action dated Apr. 23, 2015.
U.S. Appl. No. 14/199,900 Office Action dated Dec. 10, 2014.
U.S. Appl. No. 14/208,155 Office Action dated Jul. 8, 2015.
U.S. Appl. No. 14/208,155 Office Action dated Nov. 20, 2014.
U.S. Appl. No. 14/715,424 Office Action dated Oct. 24, 2016.
U.S. Appl. No. 14/806,453 Office Action dated Oct. 25, 2016.
U.S. Appl. No. 14/832,964 Office Action dated Aug. 9, 2017.
U.S. Appl. No. 14/832,964 Office Action dated Dec. 12, 2016.
U.S. Appl. No. 14/832,966 Office Action dated Apr. 12, 2018.
U.S. Appl. No. 14/832,966 Office Action dated Aug. 10, 2017.
U.S. Appl. No. 14/832,966 Office Action dated Nov. 16, 2018.
U.S. Appl. No. 16/874,473 Office Action dated Oct. 26, 2020.
U.S. Appl. No. 12/550,060 Office Action dated Apr. 2, 2014.
Ushijima et al. Methylation-Sensitive Representational Difference Analysis (MS-RDA). Methods Mol Biol 507:117-130 (2009).
Vallejo et al. Central role of thrombospondin-1 in the activation and clonal expansion of inflammatory T cells. J Immunol 164(6):2947-2954 (2000).
Van Der Molen et al. Tape stripping of human stratum corneum yields cell layers that originate from various depths because of furrows in the skin. Archives of Dermatological Research 289:514-518 (1997).
Van Der Valk et al. A functional study of the skin barrier to evaporative water loss by means of repeated cellophane-tape stripping. Clinical and Experimental Dermatology 15(3):180-182 (1990).
Van Hoogdalem. Assay of Erythromycin in Tape Strips of Human Stratum corneum and Some Preliminary results in Man. Skin Pharmacol 5:124-128 (1992).
Van Ruissen et al. Differential effects of detergents on keratinocyte gene expression. J Invest Dermatol 110(4):358-363 (1998).
Vandesompele et al. Accurate normalization of real-time quantitative RT-PCR data by geometric averaging of multiple internal control genes. Genome Biology 3(7):-112 (2002).
Vaqué et al. PLCG1 mutations in cutaneous T-cell lymphomas. Blood 123(13):2034-43 (2014).
Verhoef. The phagocytic process and the role of complement in host defense. J Chemother 3(Suppl 1):93-97 (1991).
Vermeer et al. Segregation of receptor and ligand regulates activation of epithelial growth factor receptor. Nature 422(6929):322-326 (2003).
Volinia et al. A microRNA expression signature of human solid tumors defines cance gene targets. PNAS USA 103(7):2257-2261 (2006).

Wachsman et al. Differentiation of melanoma from dysplastic nevi in suspicious pigmented skin lesions by non-invasive tape stripping. Journal of Dermatology 127(Supp 1s):S145 (2007).
Wachsman et al. Noninvasive genomic detection of melanoma, British Journal of Dermatology 164:797-806 (2011).
Wang et al. Melanoma-restricted Genes, J. of Translational Medicine 2:34 pp. 1-14 (2004).
Wang et al. MGSA/GRO-mediated melanocyte transformation involves induction of Ras expression. Oncogene 19:4647-4659 (2000).
Wang et al. Why minimally invasive skin sampling techniques? A bright scientific future. Cutan Ocul Toxicol 30(1):1-6 (2011).
Washington Report: Skin Tape Stripping Method for Generic Dermatologic Drug Approval Remains in Question, http://www.aadassociation.org/old/washReports/dec99_washrep.html (1999).
Wassem et al. Keratin 15 expression in stratified epithelia: down regulation in activated keratinocytes. Journal of Investigative Dermatology 113:362-269 (1999).
Weber et al. Chromosome-wide and promoter-specific analyses identify sites of differential DNA methylation in normal and transformed human cells. Nat. Genet. 37:853-862 (2005).
Weigand et al. Removal of Stratum Corneum in Vivo: An Improvement of the Cellophane Tape Strapping Technique. The Journal of Investigative Dermatology 60(2):84-87 (1973).
Weinstock. Early detection of melanoma. JAMA 284:886-889 (2000).
Welss et al. Hurpin is a selective inhibitor of lysosomal cathepsin L and protects keratinocytes from ultraviolet-induced apoptosis. Biochemistry 42(24):7381-7389 (2003).
Werfel et al. Cytokines as Mediators of Allergic Tissue Response. Allergologie Dustrie Verlag Muenchen-Deisenhofen, DE 20(11):546-550 (1997).
Werfel et al. High IL-4 Secretion from Skin-Derived Nickel Specific T-lymphocytes is Associated with Atopy and Acute Eczema are associated with in Allergic Contact Dermatitis. Journal of Allergy and Clinical Immunology 101(1, Part 2):S129 (1998).
Whipple et al. DNA microarrays in otolaryngology-head and neck surgery. Otolaryngol Head Neck Surg 127(3):196-204 (2002).
Wojdacz et al. Methylation-sensitive high resolution melting (MS-HRM): a new approach for sensitive and high-throughput assessment of methylation. Nucleic Acids Res. 35(6):e41 (2007).
Wojdacz et al. Methylation-sensitive high-resolution melting. Nature Protocols 3(12):1903-1908 (2008).
Wolf et al., Topical treatment with liposomes containing T4 endonuclease V protects human skin in vivo from ultraviolet-induced upregulation of interleukin-10 and tumor necrosis factor-$\alpha$. Journal of Investigative Dermatology 114.1:149-156 (2000).
Wolyn et al. Light-response quantitative trait loci identified with composite interval and extreme array mapping in *Arabidopsis thaliana*. Genetics 167(2):907-917 (2004).
Wong et al. Analysis of RNA recovery and gene expression in the epidermis using non-invasive tape stripping. J Dermatol Science 44:81-92 (2006).
Wong et al. Use of RT-PCR and DNA Microarrays to Characterize RNA Recovered by Non-Invasive Tape Harvesting of Normal and Inflamed Skin. Journal of Investigative Dermatology 123(1):159-167 (2004).
Wu et al. Preprocessing of oligonucleotide array data. Nat Biotechnol 22(6):656-658; author reply 658 (2004).
Wu et al. Stochastic models inspired by hybridization theory for short oligonucleotide arrays. J Comput Bio. 12(6):882-893 (2005).
Xiong et al COBRA: a sensitive and quantitative DNA methylation assay. Nucleic Acids Res. 25:2532-2534 (1997).
Xu et al. Expression of Cytokine mRNAs in the Draining Lymph Nodes Following Contact Sensitivity in Mice. Toxicology Methods 7:137-148 (1997).
Xu et al. RT-PCR Analysis of In Vivo Cytokine Profiles in Murine Allergic Contact Dermatitis to DNCB. Toxicology Methods. 6:23-31 (1996).
Yaar et al. Fifty years of skin ageing. JID symposium Proceedings 7(1):51-58 (2002).
Yanaihara et al. Unique microRNA molecular profiles in lung cancer diagnosis and prognosis. Cancer Cell. 9(3):189-198 (2006).

(56) References Cited

OTHER PUBLICATIONS

Yao et al. An adhesive patch-based skin biopsy device for molecular diagnostics and skin microbiome studies. J Drugs Dermatol 16:979-986 (2017).
Yao et al. An Adhesive Patch-Based Skin Biopsy Device for Non-Invasive Gene Expression Analysis in Dermatology. DermTech, Mar. 2017, available via URL: dernntech.conn/wp-content/uploads/2017/03/Skin-Biopsy-Device-1.pdf (2017).
Yao et al. Analytical Characteristics of a Noninvasive Gene Expression Assay for Pigmented Skin Lesions. Assay Drug Del Technol 14(6):355-363 (2016).
Yarosh et al., Pyrimidine dimer removal enhanced by DNA repair liposomes reduces the incidence of UV skin cancer in mice. Cancer Research 52(15):4227-4231 (1992).
Yarosh et al., Xeroderma pigmentosum study group. Effect of topically applied T4 endonuclease V in liposomes on skin cancer in xeroderma pigmentosum: a randomised study. The Lancet 357(9260):926-929 (2001).
Yawalkar et al. Pathogenesis of Drug-Induced Exanthema. Int Arch Allergy immunol. 124:336-338 (2001).
Yi et al. Morphogenesis in skin is governed by discrete sets of differentially expressed microRNAs. Nature Genetics 38(3):356-362 (2006).
Zaba et al. Effective treatment of psoriasis with etanercept is linked to suppression of IL-17 signaling, not immediate response TNF genes. J Allergy Clin Immunol 124:1022 (2009).
Zou et al., Strand opening by the UvrA2B complex allows dynamic recognition of DNA damage. The EMBO Journal 18(17):4889-4901 (1999).
Aggarwal et al. United States burden of melanoma and non-melanoma skin cancer from 1990 to 2019. J Am Acad Dermatol. 85(2):388-395 (Aug. 2021).
American Academy of Dermatology. New American Academy of Dermatology survey finds one-third of Americans fail basic quiz on skin cancer and sun exposure. Accessed Jan. 10, 2023. https://www.aad.org/news/aad-survey-finds-americans-fail-skin-cancer-quiz.
American Cancer Society. Cancer Facts & Figures 2022. Atlanta: American Cancer Society (2022).
Armstrong et al. Psoriasis Prevalence in Adults in the United States. JAMA Dermatol. 157(8):940-946 (2021).
Asgari et al. Family history of skin cancer is associated with increased risk of cutaneous squamous cell carcinoma. Dermatol Surg. 41(4):481-6 (Apr. 2015).
Aubrey et al. Tumor-Suppressor Functions of the TP53 Pathway. Cold Spring Harb Perspect Med. 6(5):a026062 (May 2, 2016).
Backes et al. Facial exposure to ultraviolet radiation: Predicted sun protection effectiveness of various hat styles. Photodermatol Photoimmunol Photomed. 34(5):330-337 (Sep. 2018).
Bissonnette et al. Palmoplantar pustular psoriasis (PPPP) is characterized by activation of the IL-17A pathway. J Dermatol Science 85(1):20-26 (2016).
Bogaczewicz et al. Medium-dose ultraviolet AI phototherapy and mRNA expression of TSLP, TARC, IL-5, and IL-13 in acute skin lesions in atopic dermatitis. Int'l J Derm 55(8):856-863 (2015).
Bolshakov et al. p53 mutations in human aggressive and nonaggressive basal and squamous cell carcinomas. Clin Cancer Res. 9(1):228-34 (Jan. 2003).
Bonilla et al. Genomic analysis identifies new drivers and progression pathways in skin basal cell carcinoma. Nat Genet. 48(4):398-406 (Apr. 2016).
Brazel et al., Genomic alterations and tumor mutation burden in merkel cell carcinoma. JAMA Netw Open 6(1):e2249674. (2023).
Brunner et al. The atopic dermatitis blood signature is characterized by increases in inflammatory and cardiovascular risk proteins. Sci Reports 7(1):8707 (2017).
Cammareri et al. Inactivation of TGFbeta receptors in stem cells drives cutaneous squamous cell carcinoma. Nat Commun. 7:12493 (Aug. 25, 2016).
Chang et al. The landscape of driver mutations in cutaneous squamous cell carcinoma. NPJ Genom Med. 6(1):61 (Jul. 16, 2021).
Chng et al. Whole metagenome profiling reveals skin microbiome-dependent susceptibility to atopic dermatitis flare. Nat Microbiol 1(9):16106 (2016).
Christenson et al. Incidence of Basal Cell and Squamous Cell Carcinomas in a Population Younger Than 40 Years. JAMA 294(6):681-690 (2005).
Ciazynska et al. Risk Factors and Clinicopathological Features for Developing a Subsequent Primary Cutaneous Squamous and Basal Cell Carcinomas. Cancers (Basel). 14(13):3069 (Jun. 23, 2022).
Coates et al. Psoriatic arthritis: state of the art review. Clin Med (Lond) 17(1):65-70 (2017).
DermTech. Pigmented Lesion Assay (PLA). Clinical Utility and Technical Assessment. Available via URL: dermtech.com/wp-content/uploads/2018/06/DIGITAL-061318PLAClinicalUtilityTechAssessment.pdf. (2 pgs) (2016).
Enk et al. The UVB-induced gene expression profile of human epidermis in vivo is different from that of cultured keratinocytes. Oncogene 25:2601-2613 (2006).
Fischer et al. Gene Expression-Based Molecular Test as Diagnostic Aid for the Differential Diagnosis of Psoriasis and Eczema in Formalin-Fixed and Paraffin-Embedded Tissue, Microbiopsies, and Tape Strips. J Invest Dermatol S0022-202X(23)00156-2 (2023).
Flament et al. Effect of the sun on visible clinical signs of aging in Caucasian skin. Clin Cosmet Investig Dermatol. 6:221-32 (2013).
Flohil et al. Risk of subsequent cutaneous malignancy in patients with prior keratinocyte carcinoma: a systematic review and meta-analysis. Eur J Cancer. 49(10):2365-75 (Jul. 2013).
Fontanillas et al. Disease risk scores for skin cancers. Nat Commun. 12(1):160 (Jan. 8, 2021).
Garzoz et al. NOS2 and CCL27: clinical implications for psoriasis and eczema diagnosis and management. Expert Rev Clinical Immunol 11(2):167-9 (2015).
Griffiths et al. Rapid method for coextraction of DNA and RNA from natural environments for analysis of ribosomal DNA- and rRNA-based microbial community composition. Appl Environ Microbiol 66(12):5488-5491 (2000).
Guilloteau et al. Skin Inflammation Induced by the Synergistic Action of IL-17A, IL-22, Oncostatin M, IL-1α, and TNF-α Recapitulates Some Features of Psoriasis. J Immunol 184(9):5263-5270 (2010).
Hawerkamp et al. Break on through: The role of innate immunity and barrier defence in atopic dermatitis and psoriasis. Skin Health Dis. 2(2):e99 (2022).
He et al. Integrated DNA and RNA extraction using magnetic beads from viral pathogens causing acute respiratory infections. Sci Rep 7:45199 (2017).
He et al. Tape strips detect distinct immune and barrier profiles in atopic dermatitis and psoriasis. J Allergy Clin Immunol 147(1):199-212 (2021).
Huang et al. Updates on Treatment Approaches for Cutaneous Field Cancerization. Curr Dermatol Rep. 8(3):122-132 (Sep. 2019).
Inman et al. The genomic landscape of cutaneous SCC reveals drivers and a novel azathioprine associated mutational signature. Nat Commun. 9(1):3667 (Sep. 10, 2018).
Jayaraman et al. Mutational landscape of basal cell carcinomas by whole-exome sequencing. J Invest Dermatol. 134(1):213-220 (Jan. 2014).
Jonason et al. Frequent clones of p53-mutated keratinocytes in normal human skin. PNAS USA 93(24):14025-9 (Nov. 26, 1996).
Kim et al. Genomic Progression of Precancerous Actinic Keratosis to Squamous Cell Carcinoma. J Invest Dermatol. 142(3 Pt A):528-538 e8 (Mar. 2022).
Kim et al. Ultraviolet radiation-induced non-melanoma skin cancer: Regulation of DNA damage repair and inflammation. Genes Dis. 1(2):188-198 (Dec. 1, 2014).
Kochmann et al. Telemedicine in the Apple App Store: An Exploratory Study of Teledermatology Apps. 2016 International Conference on Collaboration Technologies and Systems (CTS), Orlando, FL, USA, pp. 534-538 (2016).
Leachman et al.: Identification, Genetic Testing, and Management of Hereditary Melanoma. Cancer Metastasis Reviews 36(1):77-90 (2017).

(56) References Cited

OTHER PUBLICATIONS

Li et al. Genomic analysis of metastatic cutaneous squamous cell carcinoma. Clin Cancer Res 21(6):1447-56 (Mar. 15, 2015).
Lovly et al. Routine multiplex mutational profiling of melanomas enables enrollment in genotype-driven therapeutic trials. PLoS One 7(4):e35309 (2012).
Marcil et al. Risk of developing a subsequent nonmelanoma skin cancer in patients with a history of nonmelanoma skin cancer: a critical review of the literature and meta-analysis. Arch Dermatol. 136(12):1524-30 (Dec. 2000).
Martincorena et al. Tumor evolution. High burden and pervasive positive selection of somatic mutations in normal human skin. Science 348(6237):880-6 (May 22, 2015).
Meng et al. New mechanism underlying IL-31-induced atopic dermatitis. J Allergy Clin Immunol 141(5):1677-1689 (2018).
Mim et al. Feature Based Skin Disease Estimation Using Image Processing for Teledermatology. 2018 International Conference on Computer, Communication, Chemical, Material and Electronic Engineering (IC4ME2) Rajshahi, Bangladesh, pp. 1-5 (2018).
Namkoong et al., Clinical Research: Pathophysiology and Therapeutics—254: Preliminary evaluation of gene expression changes from tape stripping. Journal of Investigative Dermatology 137(5, Supp. 1):S43 [https://www.jidonline.org/article/S0022-202X(17)30452-9/pdf] (2017).
Nobbe et al. IL-31 Expression by Inflammatory Cells is Preferentially Elevated in Atopic Dermatitis. Acta Derm Venereol 92(1):24-8 (2012).
Nowell et al. Cutaneous Notch signaling in health and disease. Cold Spring Harb Perspect Med. 3(12):a017772 (Dec. 1, 2013).
PCT/US2022/018274 International Search Report and Written Opinion dated May 23, 2022.
PCT/US2022/024488 International Invitation to Pay Additional Fees dated Jul. 21, 2022.
PCT/US2022/024488 International Search Report and Written Opinion dated Sep. 16, 2022.
PCT/US2022/032194 International Search Report and Written Opinion dated Sep. 2, 2022.
PCT/US2023/066973 International Invitation to Pay Additional Fees dated Aug. 25, 2023.
Pickering et al. Mutational landscape of aggressive cutaneous squamous cell carcinoma. Clin Cancer Res. 20(24):6582-92 (Dec. 15, 2014).
Props et al. Absolute quantification of microbial taxon abundances. ISME J 11:584-587 (2017).
Qureshi et al. Geographic variation and risk of skin cancer in US women. Differences between melanoma, squamous cell carcinoma, and basal cell carcinoma. Arch Intern Med. 168(5):501-7 (Mar. 10, 2008).
Roffman et al. Predicting non-melanoma skin cancer via a multi-parameterized artificial neural network. Sci Rep. 8(1):1701 (Jan. 26, 2018).
Rogers et al. Incidence Estimate of Nonmelanoma Skin Cancer (Keratinocyte Carcinomas) in the U.S. Population, 2012. JAMA Dermatol. 151(10):1081-6 (Oct. 2015).
Rosenthal et al. Ultraviolet B Light Induces Rapid Changes in Gene Expression As Detected by Non-Invasive, Adhesive Skin Biopsies. Poster University of Miami (2019).
Salz et al. Abstract 101: Scurfy mice show autoimmune skin inflammation with features of atopic dermatitis including systemic upregulation of IL-31 and TSLP. J. Invest Dermatol 132:S19 (2012).
Schreier et al. A Mobile-Phone Based Teledermatology System to Support Self-Management of Patients Suffering from Psoriasis. Annu Int Conf IEEE Eng Med Biol Soc pp. 5338-5341 (2008).
Schweizer et al. Sequential Expression of mRNA-Encoded Keratin Sets in Neonatal Mouse Epidermis: Basal Cells with Properties of Terminally Differentiating Cells. Cell 37(1):159-171 (1984).
SEER Training Modules: Layers of the Skin. National Cancer Institute. Bethesda, MD, https://training.seer.cancer.gov/melanoma/anatomy/layers.html. Accessed Oct. 4, 2021.
Shih et al. Skin cancer has a large impact on our public hospitals but prevention programs continue to demonstrate strong economic credentials. Aust N Z J Public Health. 41(4):371-376 (Aug. 2017).
Silverberg. Public Health Burden and Epidemiology of Atopic Dermatitis. Dermatol Clin. 35(3):283-289 (2017).
Subhadarshani et al. Photocarcinogenesis. Current Dermatology Reports. 9(3):189-199 (2020).
Tate et al., COSMIC: the catalogue of somatic mutations in cancer. Nucleic Acids Res. 47(D1):D941-D947 (2019).
Temperley et al. Human mitochondrial mRNAs-like members of all families, similar but different. Biochimica et Biophysica Acta (BBA)—Bioenergetics 1797(6-7):1081-1085 (2010).
Tett et al. Unexplored diversity and strain-level structure of the skin microbiome associated with psoriasis. NPJ Biofilms Microbiomes 3:14 (2017).
ThermoFischer Scientific. TRIzol Reagent. User guide (6 pgs.) (2016).
Thijs et al. Biomarkers for atopic dermatitis: a systematic review and meta-analysis Curr Opin Allergy Clin Immunol 15(5):453-60 (2015).
Thomson et al. The Genomic Landscape of Actinic Keratosis. J Invest Dermatol. 141(7):1664-1674 e7 (Jul. 2021).
U.S. Appl. No. 16/603,435 Office Action dated Apr. 3, 2023.
U.S. Appl. No. 16/603,435 Office Action dated Nov. 7, 2022.
U.S. Appl. No. 16/603,435 Office Action dated Oct. 12, 2023.
U.S. Appl. No. 16/828,289 Office Action dated May 19, 2022.
U.S. Appl. No. 16/838,653 Office Action dated Aug. 3, 2023.
U.S. Appl. No. 16/838,653 Office Action dated Feb. 6, 2023.
U.S. Appl. No. 16/874,473 Office Action dated Jun. 27, 2023.
U.S. Appl. No. 16/874,473 Office Action dated Jun. 7, 2022.
U.S. Appl. No. 16/874,473 Office Action dated Nov. 14, 2023.
U.S. Appl. No. 17/195,541 Office Action dated Sep. 28, 2022.
U.S. Appl. No. 17/214,675 Office Action dated Aug. 2, 2022.
U.S. Appl. No. 17/214,695 Office Action dated Jul. 24, 2023.
U.S. Appl. No. 17/214,695 Office Action dated Mar. 23, 2023.
U.S. Appl. No. 17/214,695 Office Action dated Sep. 23, 2022.
U.S. Appl. No. 17/217,568 Office Action dated Feb. 14, 2023.
U.S. Appl. No. 17/217,568 Office Action dated Sep. 28, 2023.
U.S. Appl. No. 17/217,573 Office Action dated Feb. 1, 2023.
U.S. Appl. No. 17/217,573 Office Action dated Sep. 6, 2023.
U.S. Appl. No. 17/236,919 Office Action dated Aug. 23, 2023.
U.S. Appl. No. 17/354,894 Office Action dated Dec. 19, 2022.
U.S. Appl. No. 17/354,894 Office Action dated Jun. 22, 2023.
U.S. Appl. No. 17/354,899 Office Action dated Mar. 1, 2023.
U.S. Appl. No. 17/354,899 Office Action dated Nov. 17, 2023.
U.S. Appl. No. 18/056,157 Office Action dated Oct. 19, 2023.
Van Der Leest et al. Risk of subsequent cutaneous malignancy in patients with prior melanoma: a systematic review and meta-analysis. J Eur Acad Dermatol Venereol. 29(6):1053-62 (Jun. 2015).
Wang et al. Risk Assessment of Face Skin Exposure to UV Irradiance from Different Rotation Angle Ranges. Int J Environ Res Public Health. 14(6):606 (Jun. 6, 2017).
Wang et al. Use of RT-PCR and DNA microarrays to characterize RNA recovered by non-invasive tape harvesting of normal and inflamed skin. J Invest Dermatol 123(1):159-167 (2004).
Wei et al. Ultradeep sequencing differentiates patterns of skin clonal mutations associated with sun-exposure status and skin cancer burden. Sci Adv. 7(1):eabd7703 (Jan. 2021).
Yousef et al. Anatomy, Skin (integuments), Epidermis. NCBI Bookshelf. StatPearls Publishing. Nov. 14, 2022. Available via URL: ncbi.nlm.nih.gov/books/NBK470464/ (8 pgs.) (2022).
Zhang et al., The genomic landscape of cutaneous melanoma. Pigment Cell Melanoma Res 29:266-283 (2016).

* cited by examiner

FIG. 1

| HISTOPATHOLOGICAL SUBTYPES | % OF LESIONS | NOTE |
|---|---|---|
| Nodular BCC (pigmented) | 50-80% | |
| Superficial BCC (pigmented) | 10-30% | Sometimes be mistaken for inflammatory lesion, as well as SCC in situ, |
| Infundibulocystic BCC | | Can be mistaken for benign follicular adnexal process |
| Fibroepithelial BCC | Uncommon | Often be mistaken as non-pigmented seborrheic keratosis (SK) |
| Morpheaform BCC | <10% | Often seen in advanced tumor, and resembling a scar or plaque of morphea |
| Infiltrative BCC | <10% | Often seen in advanced tumor |
| Micronodular BCC | ~15% | Often seen in advanced tumor |
| Basosquamous BCC | ~2% | Metatypical BCC, features of both BCC and SCC, develop to SCC, aggressive/ metastasis |
| Perineural Invasion (PNI) | 2-6% | Aggressively invasive |

FIG. 6B

| Rank | rf |
|---|---|
| 1 | IGFL1:COL5A2 |
| 2 | IL24:AADACL2 |
| 3 | PTCH1:CD68 |

FIG. 6C

| Thresholds | Sensitivities | | | Specificities | | |
|---|---|---|---|---|---|---|
| | | 95% CI lower | 95% CI upper | | 95% CI lower | 95% CI upper |
| 0.36 | 0.90 | 0.69 | 1.00 | 0.70 | 0.41 | 0.93 |
| 0.37 | 0.90 | 0.69 | 1.00 | 0.71 | 0.43 | 0.93 |
| 0.38 | 0.90 | 0.67 | 1.00 | 0.73 | 0.44 | 0.94 |
| 0.39 | 0.90 | 0.67 | 1.00 | 0.73 | 0.45 | 1.00 |
| 0.40 | 0.90 | 0.64 | 1.00 | 0.75 | 0.46 | 1.00 |

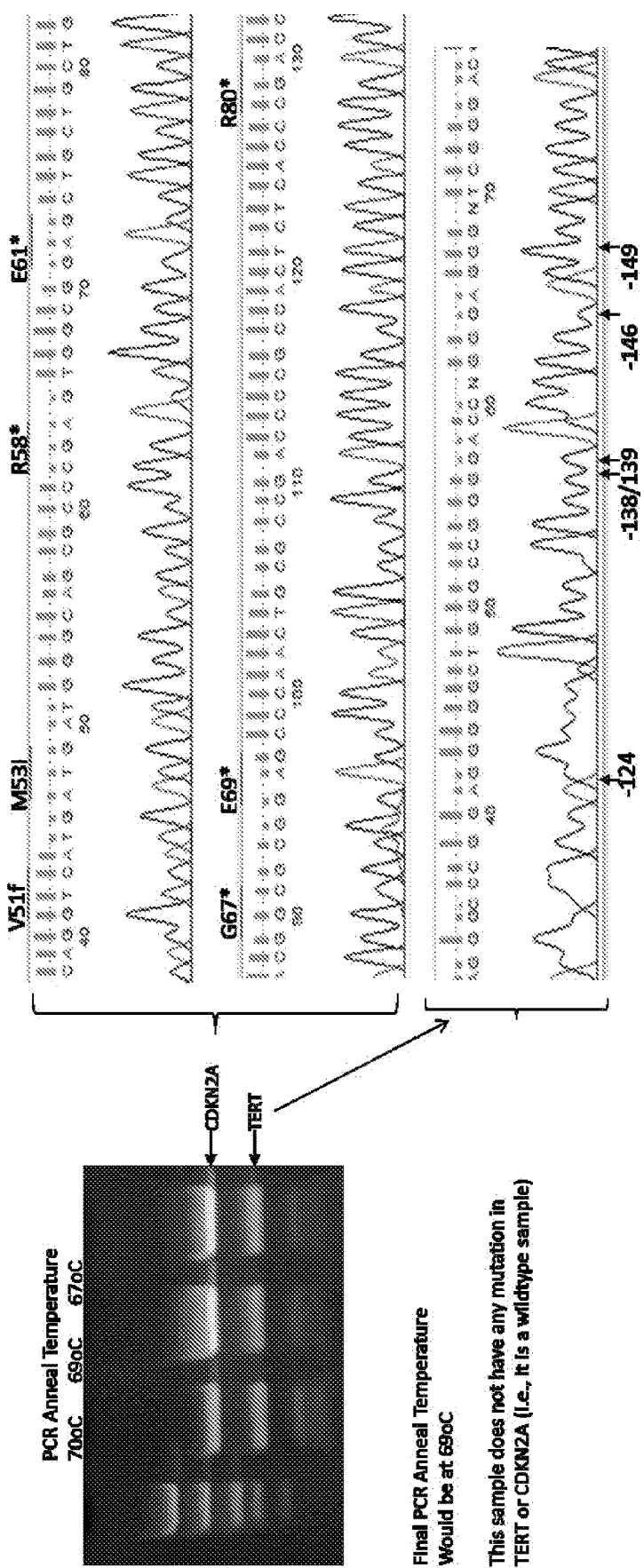

GENE CLASSIFIERS AND USES THEREOF IN NON-MELANOMA SKIN CANCERS

CROSS-REFERENCE

This application is a U.S. National Phase of International Application No. PCT/US2019/018102, filed Feb. 14, 2019, which claims the benefit of U.S. Provisional Application No. 62/630,627 filed Feb. 14, 2018, which is incorporated herein by reference in its entirety.

BACKGROUND

Skin diseases are some of the most common human illnesses and represent an important global burden in healthcare. Three skin diseases are in the top ten most prevalent diseases worldwide, and eight fall into the top 50. When considered collectively, skin conditions range from being the second to the 11th leading causes of years lived with disability.

SUMMARY

An aspect described herein is a method of detecting gene expression levels of at least two of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 in a subject in need thereof, comprising: (a) isolating nucleic acids from a biological sample obtained from the subject; and (b) detecting the expression levels of the at least two of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 by contacting the isolated nucleic acids with a set of probes that recognizes the at least two of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1, and detects binding between the at least two of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 and the set of probes. In one feature, the set of probes recognizes at least three genes selected from the group consisting of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In one feature, the set of probes recognizes at least four genes selected from the group consisting of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In one feature, the set of probes recognizes at least five genes selected from the group consisting of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In one feature, the set of probes recognizes at least six genes selected from the group consisting of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In one feature, the set of probes recognizes at least seven genes selected from the group consisting of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In one feature, the set of probes recognizes: MMP1, S100A7, CMPK2, IRF7, IGFL1, CXCL1, UPP1, DEFB4A, FOS, OAS3, SCD5, RTP4, and VEGFA; MMP1, S100A7, CMPK2, IRF7, IGFL1, CXCL1, and UPP1; or MMP1, S100A7, CMPK2, IRF7, IGFL1, and CXCL1. In one feature, the set of probes recognizes at least two genes selected from the group consisting of MMP1, S100A7, CMPK2, IRF7, IGFL1, CXCL1, and UPP1. In one feature, the set of probes recognizes at least three genes, at least four genes, at least five genes, or at least six genes selected from the group consisting of MMP1, S100A7, CMPK2, IRF7, IGFL1, CXCL1, and UPP1. In one feature, the set of probes recognizes at least two genes selected from the group consisting of MMP1, S100A7, CMPK2, IRF7, IGFL1, and CXCL1. In one feature, the set of probes recognizes at least three genes, at least four genes, or at least five genes selected from the group consisting of MMP1, S100A7, CMPK2, IRF7, IGFL1, and CXCL1. In one feature, the set of probes recognizes at least two genes selected from the group consisting of SCD5, S100A7, CMPK2, and IRF7. In one feature, the set of probes recognizes at least two and no more than thirteen genes selected from: MMP1, S100A7, CMPK2, IRF7, IGFL1, CXCL1, UPP1, DEFB4A, FOS, OAS3, SCD5, RTP4, and VEGFA. In one feature, the method further comprises detecting a mutational change of at least one gene of interest. In one feature, the detecting comprises allele specific polymerase chain reaction (PCR) or a sequencing reaction. In one feature, wherein the at least one gene of interest comprises TERT, CDKN2A, TP53, or PTCH1. In one feature, a mutation in TP53 translates to amino acid positions in TP53 selected from: R175, S240, G245, R248, R249, R273, R282, or T284, wherein the numbering of amino acid residues corresponds to SEQ ID NO: 1. In one feature, a mutation in TP53 is in exon 1, 2, 3, 4, 5, 6, 7, 8, 9, 10, 11, or a combination thereof of TP53. In one feature, a mutation in TP53 is in exon 5, 7, 8, or a combination thereof of TP53. In one feature, a mutation in PTCH1 is in exon 1, 2, 3, 4, 5, 6, 7, 8, 9, 10, 11, 12, 13, 14, 15, 16, 17, 18, 19, 20, 21, 22, 23, 24, or a combination thereof of PTCH1. In one feature, a mutation in PTCH1 is in exon 14, 15, 17, 23, or a combination thereof of PTCH1. In one feature, a mutation in CDKN2A is in exon 1, 2, 3, 4, 5, 6, 7, 8, or a combination thereof of CDKN2A. In one feature, a mutation in TERT is in exon 1, 2, 3, 4, 5, 6, 7, 8, 9, 10, 11, 12, 13, 14, 15, 16, or a combination thereof of TERT. In one feature, a mutation in TERT is in a promoter region of TERT. In one feature, the mutational change comprises at least 1.5×, 2×, 3×, 4×, 5×, 6×, 7×, 8×, 9×, 10×, 11×, or 12× more mutations in TERT, CDKN2A, TP53, PTCH1, or a combination thereof, compared to a normal biological sample. In one feature, the mutational change comprises at least 10%, 15%, 20%, 25%, 30%, 35%, 40%, 45%, 50%, 55%, 60%, 65%, 70%, 75%, or 80% more mutations in TERT, CDKN2A, TP53, PTCH1, or a combination thereof, compared to a normal biological sample. In one feature, the subject is suspected of having a cancer. In one feature, the subject is suspected of having a skin cancer. In one feature, isolating the nucleic acids comprises using a plurality of beads. In one feature, the plurality of beads is a plurality of silica-coated beads. In one feature, the plurality of silica-coated beads is a plurality of silica-coated magnetic beads. In one feature, the biological sample comprises a blood sample, saliva sample, urine sample, serum sample, plasma sample, tear sample, skin sample, tissue sample, hair sample, sample from cellular extracts, or a tissue biopsy sample. In one feature, the biological sample comprises a skin sample. In one feature, the skin sample comprises a lesion, and wherein the lesion is suspected to be melanoma, lupus, rubeola, acne, hemangioma, psoriasis, eczema, candidiasis, impetigo, shingles, leprosy, Crohn's disease, inflammatory dermatoses, bullous diseases, infections, basal cell carcinoma, actinic keratosis, seborrheic keratosis, merkel cell carcinoma, sebaceous carcinoma, squamous cell carcinoma, or dermatofibrosarcoma protuberans. In one feature, the lesion is suspected to be basal cell carcinoma or squamous cell carcinoma. In one feature, the skin sample comprises keratinocytes, melanocytes, basal cells, T-cells, or dendritic cells. In one feature, the skin sample is obtained by applying a plurality of adhesive patches to the skin sample in a manner sufficient to adhere the skin sample to the adhesive patch, and removing the adhesive patch from the skin in a manner sufficient to retain the adhered skin sample to the adhesive patch. In one feature, the plurality of adhesive patches comprises at least 4 adhesive patches. In one feature, the plurality of adhesive patches comprises about 4 adhesive patches. In one feature, the skin sample is obtained by pooling the plurality of adhesive patches. In one feature, each adhesive patch of the plurality of adhesive patches is used separately. In one feature, each adhesive patch of the plurality of adhesive patches is circular. In one feature, the each adhesive patch is at least 19 mm in diameter. In one feature, the each adhesive patch is about 19 mm in diameter. In one feature, an effective amount of the skin sample is removed by the plurality of adhesive patches. In one feature, the effective amount comprises between about 50 microgram to about 500 microgram, between about 100 microgram to about 450 microgram, between about 100 microgram to about 350 microgram, between about 100 microgram to about 300 microgram, between about 120 microgram to about 250 microgram, or between about 150 microgram to about 200 microgram of the nucleic acids. In one feature, the nucleic acids are stable on the plurality of adhesive patches for at least 1 week. In one feature, the nucleic acids are stable on the plurality of adhesive patches at a temperature of up to about 60° C. In one feature, the nucleic acids are stable on the plurality of adhesive patches at room temperature. In one feature, a yield of the nucleic acids is at least about 200 picograms, at least about 500 picograms, at least about 750 picograms, at least about 1000 picograms, at least about 1500 picograms, or at least about 2000 picograms. In one feature, the nucleic acids comprise RNA, DNA, or a combination thereof. In one feature, the RNA is mRNA. In one feature, the RNA is cell-free circulating RNA. In one feature, the DNA is genomic DNA. In one feature, the genomic DNA is cell-free circulating genomic DNA. In one feature, detecting the expression levels comprise quantitative polymerase chain reaction (qPCR), sequencing, or microarray analysis.

An aspect described herein is a method of detecting gene expression levels of at least two of MMP1, S100A7, CMPK2, IRF7, IGFL1, CXCL1, and UPP1 in a subject in need thereof, comprising: (a) isolating nucleic acids from a biological sample obtained from the subject; and (b) detecting the expression levels of the at least two of MMP1, S100A7, CMPK2, IRF7, IGFL1, CXCL1, and UPP1, by contacting the isolated nucleic acids with a set of probes that recognizes the at least two of MMP1, S100A7, CMPK2, IRF7, IGFL1, CXCL1, and UPP1, and detects binding between the at least two of MMP1, S100A7, CMPK2, IRF7, IGFL1, CXCL1, and UPP1 and the set of probes. In one feature, the set of probes recognizes at least three genes, at least four genes, at least five genes, or at least six genes selected from the group consisting of MMP1, S100A7, CMPK2, IRF7, IGFL1, CXCL1, and UPP1. In one feature, the set of probes recognizes at least two genes selected from the group consisting of MMP1, S100A7, CMPK2, IRF7, IGFL1, and CXCL1. In one feature, the set of probes recognizes at least three genes, at least four genes, or at least five genes selected from the group consisting of MMP1, S100A7, CMPK2, IRF7, IGFL1, and CXCL1. In one feature, the set of probes recognizes at least two genes selected from the group consisting of SCD5, S100A7, CMPK2, and IRF7. In one feature, the set of probes recognizes at least two and no more than seven genes selected from: MMP1, S100A7, CMPK2, IRF7, IGFL1, CXCL1, and UPP1. In one feature, the method further comprises detecting a mutational change of at least one gene of interest. In one feature, the detecting comprises allele specific polymerase chain reaction (PCR) or a sequencing reaction. In one feature, the at least one gene of interest comprises TERT, CDKN2A, TP53, or PTCH1. In one feature, a mutation in TP53 translates to amino acid positions in TP53 selected from: R175, S240, G245, R248, R249, R273, R282, or T284, wherein the numbering of amino acid residues corresponds to SEQ ID NO: 1. In one feature, a mutation in TP53 is in exon 1, 2, 3, 4, 5, 6, 7, 8, 9, 10, 11, or a combination thereof of TP53. In one feature, a mutation in TP53 is in exon 5, 7, 8, or a combination thereof of TP53. In one feature, a mutation in PTCH1 is in exon 1, 2, 3, 4, 5, 6, 7, 8, 9, 10, 11, 12, 13, 14, 15, 16, 17, 18, 19, 20, 21, 22, 23, 24, or a combination thereof of PTCH1. In one feature, a mutation in PTCH1 is in exon 14, 15, 17, 23, or a combination thereof of PTCH1. In one feature, a mutation in CDKN2A is in exon 1, 2, 3, 4, 5, 6, 7, 8, or a combination thereof of CDKN2A. In one feature, a mutation in TERT is in exon 1, 2, 3, 4, 5, 6, 7, 8, 9, 10, 11, 12, 13, 14, 15, 16, or a combination thereof of TERT. In one feature, a mutation in TERT is in a promoter region of TERT. In one feature, the mutational change comprises at least 1.5×, 2×, 3×, 4×, 5×, 6×, 7×, 8×, 9×, 10×, 11×, or 12× more mutations in TERT, CDKN2A, TP53, PTCH1, or a combination thereof, compared to a normal biological sample. In one feature, the mutational change comprises at least 10%, 15%, 20%, 25%, 30%, 35%, 40%, 45%, 50%, 55%, 60%, 65%, 70%, 75%, or 80% more mutations in TERT, CDKN2A, TP53, PTCH1, or a combination thereof, compared to a normal biological sample. In one feature, the subject is suspected of having a cancer. In one feature, the subject is suspected of having a skin cancer. In one feature, isolating the nucleic acids comprises using a plurality of beads. In one feature, plurality of beads is a plurality of silica-coated beads. In one feature, the plurality of silica-coated beads is a plurality of silica-coated magnetic beads. In one feature, the biological sample comprises a blood sample, saliva sample, urine sample, serum sample, plasma sample, tear sample, skin sample, tissue sample, hair sample, sample from cellular extracts, or a tissue biopsy sample. In one feature, the biological sample comprises a skin sample. In one feature, the skin sample comprises a lesion, and wherein the lesion is suspected to be melanoma, lupus, rubeola, acne, hemangioma, psoriasis, eczema, candidiasis, impetigo, shingles, leprosy, Crohn's disease, inflammatory dermatoses, bullous diseases, infections, basal cell carcinoma, actinic keratosis, seborrheic keratosis, merkel cell carcinoma, sebaceous carcinoma, squamous cell carcinoma, or dermatofibrosarcoma protuberans. In one feature, the lesion is suspected to be basal cell carcinoma or squamous cell carcinoma. In one feature, the skin sample comprises keratinocytes, melanocytes, basal cells, T-cells, or dendritic cells. In one feature, the skin sample is obtained by applying a plurality of adhesive patches to the skin sample in a manner sufficient to adhere the skin sample to the adhesive patch, and removing the adhesive patch from the skin in a manner sufficient to retain the adhered skin sample to the adhesive patch. In one feature, the plurality of adhesive patches comprises at least 4 adhesive patches. In one feature, the plurality of adhesive patches comprises about 4 adhesive patches. In one feature, the skin sample is obtained by pooling the plurality of adhesive patches. In one feature, each adhesive patch of the plurality of adhesive patches is used separately. In one feature, each adhesive patch of the plurality of adhesive patches is circular. In one feature, the each adhesive patch is at least 19 mm in diameter. In one feature, the each adhesive patch is about 19 mm in diameter. In one feature, an effective amount of the skin sample is removed by the plurality of adhesive patches. In one feature, the effective amount comprises between about 50 microgram to about 500 microgram, between about 100 microgram to about 450 microgram, between about 100 microgram to about 350 microgram, between about 100 microgram to about 300 microgram, between about 120 microgram to about 250 microgram, or between about 150 microgram to about 200 microgram of the nucleic acids. In one feature, the nucleic acids are stable on the plurality of adhesive patches for at least 1 week. In one feature, the nucleic acids are stable on the plurality of adhesive patches at a temperature of up to about 60° C. In one feature, the nucleic acids are stable on the plurality of adhesive patches at room temperature. In one feature, a yield of the nucleic acids is at least about 200 picograms, at least about 500 picograms, at least about 750 picograms, at least about 1000 picograms, at least about 1500 picograms, or at least about 2000 picograms. In one feature, the nucleic acids comprise RNA, DNA, or a combination thereof. In one feature, the RNA is mRNA. In one feature, the RNA is cell-free circulating RNA. In one feature, the DNA is genomic DNA. In one feature, the genomic DNA is cell-free circulating genomic DNA. In one feature, detecting the expression levels comprise quantitative polymerase chain reaction (qPCR), sequencing, or microarray analysis.

An aspect described herein is a method of diagnosing and treating a disease or disorder in a subject, comprising: (a) isolating nucleic acids from a biological sample obtained from the subject; (b) detecting the expression levels of at least two genes selected from the group consisting of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1, and comparing the expression levels of the at least two genes to a control; (c) identifying the subject as having the disease or disorder if there is a change in the expression levels of the at least two genes relative to the control; and (d) administering an effective amount of a therapeutic agent to the diagnosed subject.

An aspect described herein is a method of diagnosing a disease or disorder in a subject, comprising: (a) isolating nucleic acids from a biological sample obtained from the subject; (b) detecting the expression levels of at least two genes selected from the group consisting of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1, and comparing the expression levels of the at least two genes to a control; and (c) identifying the subject as having the disease or disorder if there is a change in the expression levels of the at least two genes relative to the control. In one feature, at least three genes are selected from the group consisting of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In one feature, at least four genes are selected from the group consisting of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In one feature, at least five genes are selected from the group consisting of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In one feature, at least six genes are selected from the group consisting of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In one feature, at least seven genes are selected from the group consisting of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In one feature, the at least two genes are selected from the group consisting of MMP1, S100A7, CMPK2, IRF7, IGFL1, CXCL1, and UPP1. In one feature, at least three genes, at least four genes, at least five genes, or at least six genes are selected from the group consisting of MMP1, S100A7, CMPK2, IRF7, IGFL1, CXCL1, and UPP1. In one feature, the at least two genes is selected from the group consisting of MMP1, S100A7, CMPK2, IRF7, IGFL1, and CXCL1. In one feature, at least three genes, at least four genes, or at least five genes are selected from the group consisting of MMP1, S100A7, CMPK2, IRF7, IGFL1, and CXCL1. In one feature, the at least two genes is selected from the group consisting of SCD5, S100A7, CMPK2, and IRF7. In one feature, the method further comprises detecting a mutational change of a gene of interest. In one feature, the detecting comprises allele specific polymerase chain reaction (PCR) or a sequencing reaction. In one feature, the gene of interest comprises TERT, CDKN2A, TP53, or PTCH1. In one feature, a mutation in TP53 translates to amino acid positions in TP53 selected from: R175, S240, G245, R248, R249, R273, R282, or T284, wherein the numbering of amino acid residues corresponds to SEQ ID NO: 1. In one feature, a mutation in TP53 is in exon 1, 2, 3, 4, 5, 6, 7, 8, 9, 10, 11, or a combination thereof of TP53. In one feature, a mutation in TP53 is in exon 5, 7, 8, or a combination thereof of TP53. In one feature, a mutation in PTCH1 is in exon 1, 2, 3, 4, 5, 6, 7, 8, 9, 10, 11, 12, 13, 14, 15, 16, 17, 18, 19, 20, 21, 22, 23, 24, or a combination thereof of PTCH1. In one feature, a mutation in PTCH1 is in exon 14, 15, 17, 23, or a combination thereof of PTCH1. In one feature, a mutation in CDKN2A is in exon 1, 2, 3, 4, 5, 6, 7, 8, or a combination thereof of CDKN2A. In one feature, a mutation in TERT is in exon 1, 2, 3, 4, 5, 6, 7, 8, 9, 10, 11, 12, 13, 14, 15, 16, or a combination thereof of TERT. In one feature, a mutation in TERT is in a promoter region of TERT. In one feature, the mutational change comprises at least 1.5×, 2×, 3×, 4×, 5×, 6×, 7×, 8×, 9×, 10×, 11×, or 12× more mutations in TERT, CDKN2A, TP53, PTCH1, or a combination thereof, compared to a normal biological sample. In one feature, the mutational change comprises at least 10%, 15%, 20%, 25%, 30%, 35%, 40%, 45%, 50%, 55%, 60%, 65%, 70%, 75%, or 80% more mutations in TERT, CDKN2A, TP53, PTCH1, or a combination thereof, compared to a normal biological sample. In one feature, the subject is suspected of having a cancer. In one feature, the subject is suspected of having a skin cancer. In one feature, the biological sample comprises a blood sample, saliva sample, urine sample, serum sample, plasma sample, tear sample, skin sample, tissue sample, hair sample, sample from cellular extracts, or a tissue biopsy sample. In one feature, the biological sample comprises a skin sample. In one feature, the skin sample comprises a lesion, and wherein the lesion is suspected to be melanoma, lupus, rubeola, acne, hemangioma, psoriasis, eczema, candidiasis, impetigo, shingles, leprosy, Crohn's disease, inflammatory dermatoses, bullous diseases, infections, basal cell carcinoma, actinic keratosis, seborrheic keratosis, merkel cell carcinoma, sebaceous carcinoma, squamous cell carcinoma, or dermatofibrosarcoma protuberans. In one feature, the lesion is suspected to be basal cell carcinoma or squamous cell carcinoma. In one feature, treatment for the basal cell carcinoma or squamous cell carcinoma comprises surgery. In one feature, treatment for actinic keratosis comprises a topical treatment. In one feature, the skin sample comprises keratinocytes, melanocytes, basal cells, T-cells, or dendritic cells. In one feature, the skin sample is obtained by applying a plurality of adhesive patches to the skin sample in a manner sufficient to adhere the skin sample to the adhesive patch, and removing the adhesive patch from the skin in a manner sufficient to retain the adhered skin sample to the adhesive patch. In one feature, the plurality of adhesive patches comprises at least 4 adhesive patches. In one feature, the plurality of adhesive patches comprises about 4 adhesive patches. In one feature, the skin sample is obtained by pooling the plurality of adhesive patches. In one feature, each adhesive patch of the plurality of adhesive patches is used separately. In one feature, each adhesive patch of the plurality of adhesive patches is circular. In one feature, the each adhesive patch is at least 19 mm in diameter. In one feature, the each adhesive patch is about 19 mm in diameter. In one feature, an effective amount of the skin sample is removed by the plurality of adhesive patches. In one feature, the effective amount comprises between about 50 microgram to about 500 microgram, between about 100 microgram to about 450 microgram, between about 100 microgram to about 350 microgram, between about 100 microgram to about 300 microgram, between about 120 microgram to about 250 microgram, or between about 150 microgram to about 200 microgram of the nucleic acids. In one feature, the nucleic acids are stable on the plurality of adhesive patches for at least 1 week. In one feature, the nucleic acids are stable on the plurality of adhesive patches at a temperature of up to about 60° C. In one feature, the nucleic acids are stable on the plurality of adhesive patches at room temperature. In one feature, a yield of the nucleic acids is at least about 200 picograms, at least about 500 picograms, at least about 750 picograms, at least about 1000 picograms, at least about 1500 picograms, or at least about 2000 picograms. In one feature, the nucleic acids comprise RNA, DNA, or a combination thereof. In one feature, the RNA is mRNA. In one feature, the RNA is cell-free circulating RNA. In one feature, the DNA is genomic DNA. In one feature, the genomic DNA is cell-free circulating genomic DNA. In one feature, detecting the expression levels comprises quantitative polymerase chain reaction (qPCR), sequencing, or microarray analysis.

An aspect described herein is a computer-implemented method for differentiating one or more cancer samples from one or more non-cancer samples, comprising: (a) hybridizing a set of probes that recognizes MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 to generate gene expression data; (b) obtaining, by a processor, the gene expression data; and (c) analyzing, by the processor, the gene expression data to differentiate the one or more cancer samples from the one or more non-cancer samples, wherein the analysis comprises: (i) generating a plurality of pair-wise interactions between at least two genes of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 in a set of samples; (ii) analyzing the plurality of pair-wise interactions using a machine learning method to determine an area under a curve (AUC) value for each of the plurality of pair-wise interactions; and (iii) differentiating the one or more cancer samples from the one or more non-cancer samples when an AUC value is greater than above about 0.8.

An aspect described herein are methods, wherein a sensitivity of the methods is at least 80%.

An aspect described herein are methods, wherein a specificity of the method is at least 80%.

An aspect described herein is a computer-implemented system comprising: (a) a first computing device comprising a processor, a memory module, an operating system, and a computer program including instructions executable by the processor to create a data acquisition application for receiving gene expression from a sample, the data acquisition application comprising: a data receiving module for receiving gene expression data of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, SPP1, or a combination thereof, and (b) a second computing device comprising a processor, a memory module, an operating system, and a computer program including instructions executable by the processor to create a data analysis application for differentiating a cancer sample from a non-cancer sample, the data analysis application comprising a data analysis module to: (i) generate a plurality of pair-wise interactions between at least two genes of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 from the gene expression data; and (ii) analyze the plurality of pair-wise interactions with a control using a machine learning method to differentiate a cancer sample from a non-cancer sample, wherein the machine learning method comprises: (1) identifying a plurality of weights associated with the plurality of pair-wise interactions based on a top score; (2) determining an area under a curve (AUC) value for each of the plurality of pair-wise interactions; and (3) classifying the sample as a cancer or non-cancer sample based on the plurality of pair-wise interactions and the plurality of weights when the AUC value is greater than about 0.8.

An aspect described herein is a non-transitory computer-readable medium with instructions stored thereon, that when executed by a processor, perform the steps comprising: (a) generating gene expression data of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 from a set of biological samples by a hybridizing method; (b) obtaining, by a processor, the gene expression data; (c) generating a plurality of pair-wise interactions between at least two genes of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1; (d) analyzing the plurality of pair-wise interactions using a machine learning method to determine an area under a curve (AUC) value for each of the plurality of pair-wise interactions; and (e) differentiating the one or more cancer samples from the one or more non-cancer samples when an AUC value is greater than above about 0.8.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 illustrates a chart showing exemplary subtypes of basal cell carcinoma (BCC).

FIG. 2A shows algorithmic models for a comparison of basal cell carcinoma (BCC) and squamous cell carcinoma (SCC) to actinic keratosis (AK), seborrheic keratosis (SK), and normal samples. FIG. 2B shows algorithmic models for comparison of basal cell carcinoma (BCC) and squamous cell carcinoma (SCC) to actinic keratosis (AK).

FIG. 3A shows rf analysis model for a comparison of basal cell carcinoma (BCC) and squamous cell carcinoma (SCC) to actinic keratosis (AK), seborrheic keratosis (SK), and normal samples. FIG. 3B shows rf analysis model for a comparison of basal cell carcinoma (BCC) and squamous cell carcinoma (SCC) to actinic keratosis (AK).

FIG. 6A-FIG. 6C illustrate the sensitivity and specificity of the tested BCC and SCC samples. FIG. 6B illustrates the set of variables used to generate the AUC in FIG. 6A. FIG. 6C provides the sensitivity and specificity of the set of variables from FIG. 6B based on five different threshold criteria.

FIG. 7A shows an exemplary biplex PCR amplification of CDKN2A and TERT exons.

FIG. 7B shows an exemplary Sanger sequencing of CDKN2A and TERT wild-type sequences.

FIG. 8A shows the number of mutations detected with respect to each exon from BCC, SCC, and AK. FIG. 8B shows the number of exons detected and the number of mutations detected within each exon in the tested BCC samples.

DETAILED DESCRIPTION

Figure 2A:
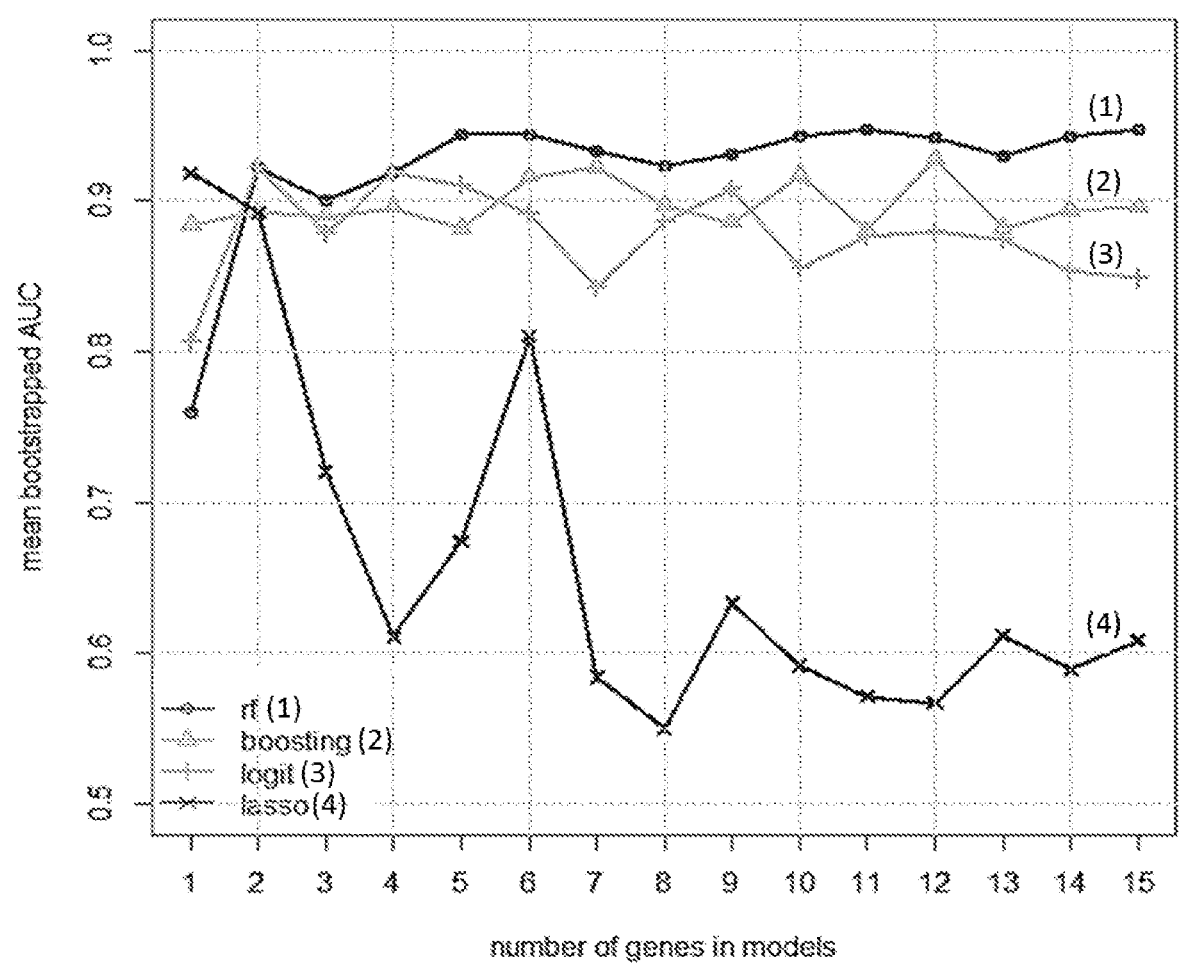
FIG. 2A-FIG. 2B illustrate graphs comparing various algorithmic models.

Non-melanoma skin cancer (NMSC) encompasses a collection of skin cancers that is not melanoma and is the most common type of skin cancer. NMSC includes angiosarcoma, basal cell carcinoma (BCC), cutaneous B-cell lymphoma, cutaneous T-cell lymphoma, dermatofibrosarcoma protuberans, Merkel cell carcinoma, sebaceous carcinoma, and squamous cell carcinoma of the skin (SCC). In some instances, basal cell carcinoma and squamous cell carcinoma are the two most common types of NMSC.

Basal cell carcinoma (BCC) is an uncontrolled growth or lesion from the basal cells (or basal keratinocytes), the deepest layer of the epidermis. In some instances, BCC is developed on sun-exposed areas, e.g., in the head and neck area. BCC is a slow-growing cancer and generally does not spread to other parts of the body. In some instances, BCC is further classified into subtypes and the subtypes comprises nodular BCC (pigmented), superficial BCC (pigmented), infundibulocystic BCC, fibroepithelial BCC, morpheaform BCC, infiltrative BCC, miconodular BCC, basosquamous BCC, and perineural invasion (PNI). Also see FIG. 1. Additional subtypes of BCC include nodulocystic, microcystic, adenoid, follicular, rodent ulcer, neurotropic, solitary basal cell carcinoma in young persons, pleomorphic, clear cell, granular cell, and singlet ring cell BCC.

Squamous cell carcinoma (SCC) (also known as cutaneous squamous cell carcinoma (CSCC) or epidermoid carcinoma) is the second most common form of skin cancer. Similar to BCC, SCC also originates from the basal keratinocytes and is a slow growing cancer, usually found in UV exposed areas such as the head and neck. In some instances, SCC is further classified into subtypes and the subtypes comprises squamous cell carcinoma in situ (also known as Bowen's disease), invasive squamous cell carcinoma (SCCI), clear cell SCC, spindle cell (sarcomatoid) SCC, SCC with single cell infiltrates, de novo SCC, verrucous carcinoma (VC), and lymphoepithelioma-like carcinoma of the skin. In some instances, the SCC subtype also comprises keratoacanthomas.

Diagnosis of skin cancers include both invasive techniques and non-invasive methods with the gold standard being biopsy followed by histopathology evaluation. In some instances, non-invasive methods have reduced specificity and/or sensitivity, and often require a biopsy step for conclusive diagnosis.

Provided herein are methods and compositions for non-invasively diagnosing or detecting a skin disease, e.g., a non-melanoma skin cancer (NMSC) or melanoma. In some instances, methods and compositions as described herein are used for diagnosing or detecting BCC. In other instances, methods and compositions as described herein are used for diagnosing or detecting SCC. In some cases, methods and compositions as described herein comprise improved sensitivity and specificity for diagnosing or detecting a skin disease, e.g., a NMSC such BCC or SCC.

Carcinoma Assay

Methods and compositions as described herein are used for detecting gene expression levels of a gene of interest. In some instances, the gene of interest is implicated in a skin disease. In some instances, the skin disease is a non-melanoma skin cancer (NMSC). In some instances, the NMSC is BCC or SCC. In some cases, the skin disease is melanoma. Exemplary genes associated with a skin disease (e.g., a NMSC such as BCC or SCC) and, in some instances, detected using methods described herein include, but are not limited to, MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In some instances, the gene of interest is MMP1. In some instances, the gene of interest is S100A7. In some instances, the gene of interest is CMPK2. In some instances, the gene of interest is IRF7. In some instances, the gene of interest is IGFL1. In some instances, the gene of interest is CXCL1. In some instances, the gene of interest is UPP1. In some instances, the gene of interest is DEFB4A. In some instances, the gene of interest is FOS. In some instances, the gene of interest is OAS3. In some instances, the gene of interest is SCD5. In some instances, the gene of interest is RTP4. In some instances, the gene of interest is VEGFA. In some instances, the gene of interest is COL5A2. In some instances, the gene of interest is IL24. In some instances, the gene of interest is AADACL2. In some instances, the gene of interest is PTCH1. In some instances, the gene of interest is CD68. In some instances, the gene of interest is PRKACA. In some instances, the gene of interest is SPP1.

In some embodiments, the gene expression levels of one or more genes of interest are detected. In some instances, at least two of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 are detected. In some instances, at least three of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 are detected. In some instances, at least four of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 are detected. In some instances, at least five of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 are detected. In some instances, at least six of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 are detected. In some instances, at least seven of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 are detected. In some instances, at least eight of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 are detected. In some instances, at least nine of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 are detected. In some instances, at least ten of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 are detected. In some instances, at least eleven of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 are detected. In some instances, at least twelve of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 are detected. In some instances, all of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 are detected.

In some embodiments, the gene expression level of one or more genes selected from IGFL1, MMP1, COL5A2, IL24, AADACL2, PTCH1, CD68, PRKACA, and SPP1 is detected. In some cases, the gene expression levels of two or more genes selected from IGFL1, MMP1, COL5A2, IL24, AADACL2, PTCH1, CD68, PRKACA, and SPP1 are detected. In some cases, the gene expression levels of three or more genes selected from IGFL1, MMP1, COL5A2, IL24, AADACL2, PTCH1, CD68, PRKACA, and SPP1 are detected. In some cases, the gene expression levels of four or more genes selected from IGFL1, MMP1, COL5A2, IL24, AADACL2, PTCH1, CD68, PRKACA, and SPP1 are detected. In some cases, the gene expression levels of five or more genes selected from IGFL1, MMP1, COL5A2, IL24, AADACL2, PTCH1, CD68, PRKACA, and SPP1 are detected. In some cases, the gene expression levels of six or more genes selected from IGFL1, MMP1, COL5A2, IL24, AADACL2, PTCH1, CD68, PRKACA, and SPP1 are detected. In some cases, the gene expression levels of seven or more genes selected from IGFL1, MMP1, COL5A2, IL24, AADACL2, PTCH1, CD68, PRKACA, and SPP1 are detected. In some cases, the gene expression levels of eight or more genes selected from IGFL1, MMP1, COL5A2, IL24, AADACL2, PTCH1, CD68, PRKACA, and SPP1 are detected. In some cases, the gene expression levels of IGFL1, MMP1, COL5A2, IL24, AADACL2, PTCH1, CD68, PRKACA, and SPP1 are detected.

In some instances, the gene expression levels of IGFL1 in combination with one or more of COL5A2, IL24, AADACL2, PTCH1, CD68, PRKACA, and SPP1 are detected. In some cases, the gene expression levels of IGFL1 in combination with two or more of COL5A2, IL24, AADACL2, PTCH1, CD68, PRKACA, and SPP1 are detected. In some cases, the gene expression levels of IGFL1 in combination with three or more of COL5A2, IL24, AADACL2, PTCH1, CD68, PRKACA, and SPP1 are detected. In some cases, the gene expression levels of IGFL1 in combination with four or more of COL5A2, IL24, AADACL2, PTCH1, CD68, PRKACA, and SPP1 are detected. In some cases, the gene expression levels of IGFL1 in combination with five or more of COL5A2, IL24, AADACL2, PTCH1, CD68, PRKACA, and SPP1 are detected. In some cases, the gene expression levels of IGFL1 in combination with six or more of COL5A2, IL24, AADACL2, PTCH1, CD68, PRKACA, and SPP1 are detected. In some cases, the gene expression levels of IGFL1 in combination with COL5A2, IL24, AADACL2, PTCH1, CD68, PRKACA, and SPP1 are detected.

In some instances, the gene expression levels of MMP1 in combination with one or more of COL5A2, IL24, AADACL2, PTCH1, CD68, PRKACA, and SPP1 are detected. In some cases, the gene expression levels of MMP1 in combination with two or more of COL5A2, IL24, AADACL2, PTCH1, CD68, PRKACA, and SPP1 are detected. In some cases, the gene expression levels of MMP1 in combination with three or more of COL5A2, IL24, AADACL2, PTCH1, CD68, PRKACA, and SPP1 are detected. In some cases, the gene expression levels of MMP1 in combination with four or more of COL5A2, IL24, AADACL2, PTCH1, CD68, PRKACA, and SPP1 are detected. In some cases, the gene expression levels of MMP1 in combination with five or more of COL5A2, IL24, AADACL2, PTCH1, CD68, PRKACA, and SPP1 are detected. In some cases, the gene expression levels of MMP1 in combination with six or more of COL5A2, IL24, AADACL2, PTCH1, CD68, PRKACA, and SPP1 are detected. In some cases, the gene expression levels of MMP1 in combination with COL5A2, IL24, AADACL2, PTCH1, CD68, PRKACA, and SPP1 are detected.

In some instances, the gene expression levels of IGFL1 and MMP in combination with one or more of COL5A2, IL24, AADACL2, PTCH1, CD68, PRKACA, and SPP1 are detected. In some cases, the gene expression levels of IGFL1 and MMP in combination with two or more of COL5A2, IL24, AADACL2, PTCH1, CD68, PRKACA, and SPP1 are detected. In some cases, the gene expression levels of IGFL1 and MMP in combination with three or more of COL5A2, IL24, AADACL2, PTCH1, CD68, PRKACA, and SPP1 are detected. In some cases, the gene expression levels of IGFL1 and MMP in combination with four or more of COL5A2, IL24, AADACL2, PTCH1, CD68, PRKACA, and SPP1 are detected. In some cases, the gene expression levels of IGFL1 and MMP in combination with five or more of COL5A2, IL24, AADACL2, PTCH1, CD68, PRKACA, and SPP1 are detected. In some cases, the gene expression levels of IGFL1 and MMP in combination with six or more of COL5A2, IL24, AADACL2, PTCH1, CD68, PRKACA, and SPP1 are detected. In some cases, the gene expression levels of IGFL1 and MMP1 in combination with COL5A2, IL24, AADACL2, PTCH1, CD68, PRKACA, and SPP1 are detected.

In some embodiments, the gene expression levels of at least two of MMP1, S100A7, CMPK2, IRF7, IGFL1, CXCL1, and UPP1 are detected. In some embodiments, the gene expression levels of at least three of MMP1, S100A7, CMPK2, IRF7, IGFL1, CXCL1, and UPP1 are detected. In some embodiments, the gene expression levels of at least four of MMP1, S100A7, CMPK2, IRF7, IGFL1, CXCL1, and UPP1 are detected. In some embodiments, the gene expression levels of at least five of MMP1, S100A7, CMPK2, IRF7, IGFL1, CXCL1, and UPP1 are detected. In some embodiments, the gene expression levels of at least six of MMP1, S100A7, CMPK2, IRF7, IGFL1, CXCL1, and UPP1 are detected. In some embodiments, the gene expression levels of all of MMP1, S100A7, CMPK2, IRF7, IGFL1, CXCL1, and UPP1 are detected.

In some embodiments, the gene expression levels of at least two of MMP1, S100A7, CMPK2, IRF7, IGFL1, and CXCL1 are detected. In some embodiments, the gene expression levels of at least three of MMP1, S100A7, CMPK2, IRF7, IGFL1, and CXCL1 are detected. In some embodiments, the gene expression levels of at least four of MMP1, S100A7, CMPK2, IRF7, IGFL1, and CXCL1 are detected. In some embodiments, the gene expression levels of at least five of MMP1, S100A7, CMPK2, IRF7, IGFL1, and CXCL1 are detected. In some embodiments, the gene expression levels of all of MMP1, S100A7, CMPK2, IRF7, IGFL1, and CXCL1 are detected.

In some embodiments, the gene expression levels of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, SPP1, or a combination thereof are used to differentiate cancer samples from non-cancer samples. In some embodiments, the gene expression levels of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, SPP1, or a combination thereof in cancer samples and non-cancer samples are analyzed using various algorithmic models. In some instances, the algorithmic model is random forest (rf) model, boosting model, logit model, lasso model, or combinations thereof. In some instances, the algorithmic model is the rf model. In some embodiments, methods for differentiating cancer samples from non-cancer samples comprises various variables including, but not limited to, interactions between MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In some instances, the interactions are among at least or about 2 genes, 3 genes, 4 genes, 5 genes, 6 genes, 7 genes, 8 genes, 9 genes, 10 genes, 11 genes, 12 genes, or 13 genes. In some instances, the interactions are among at least or about 1, 2, 3, 4, 5, 6, 7, 8, 9, 10, 11, 12, 13, 14, 15, or more than 15 pairs of genes. Exemplary gene interactions are seen in Tables 1-3.

TABLE 1

| rank | rf | boosting | lasso | logit |
|---|---|---|---|---|
| 1 | MMP1.S100A7 | Genes with low expression | Genes with low expression | IGFL1.MMP1 |
| 2 | CMPK2.IRF7 | CXCL1.OAS3 | IGFL1.MMP1 | CMPK2.SCD5 |
| 3 | Genes with low expression | IGFL1.CMPK2 | SCD5.S100A7 | UPP1v2.RTP4 |
| 4 | IGFL1.CXCL1 | CMPK2.IRF7 | DEFB4A | UPP1v2.SCD5 |
| 5 | IGFL1.CMPK2 | MMP1.CMPK2 | UPP1v2.SCD5 | IGFL1.IRF7 |
| 6 | UPP1v2.CMPK2 | IGFL1.IRF7 | MMP1.S100A7 | IGFL1.DEFB4A |
| 7 | MMP1.CMPK2 | MMP1.S100A7 | CXCL1.IRF7 | FOS.SCD5 |
| 8 | CXCL1.IRF7 | UPP1v2.CMPK2 | MMP1.SCD5 | FOS.IRF7 |
| 9 | IGFL1.SCD5 | CXCL1.RTP4 | CMPK2 | IGFL1.RTP4 |
| 10 | IGFL1.IRF7 | CXCL1.IRF7 | CMPK2.RTP4 | RTP4 |
| 11 | CXCL1.SCD5 | MMP1.SCD5 | FOS.IRF7 | S100A7 |
| 12 | CMPK2.S100A7 | FOS.IRF7 | FOS.RTP4 | DEFB4A.FOS |
| 13 | CXCL1.S100A7 | CXCL1.SCD5 | S100A7 | SCD5 |

TABLE 1-continued

| rank | rf | boosting | lasso | logit |
|---|---|---|---|---|
| 14 | IGFL1.MMP1 | CXCL1.CMPK2 | FOS.CMPK2 | UPP1v2.OAS3 |
| 15 | CXCL1.CMPK2 | FOS.CMPK2 | CMPK2.SCD5 | UPP1v2.MMP1 |

TABLE 2

| rank | rf | boosting | lasso | logit |
|---|---|---|---|---|
| 1 | SCD5.S100A7 | CXCL1.SCD5 | Genes with low expression | Genes with low expression |
| 2 | CMPK2.IRF7 | CMPK2.IRF7 | UPP1v2.FOS | UPP1v2.FOS |
| 3 | CXCL1.SCD5 | MMP1.OAS3 | SCD5.VEGFA | IGFL1.VEGFA |
| 4 | MMP1.CMPK2 | SCD5.S100A7 | CXCL1.CMPK2 | FOS |
| 5 | CMPK2.S100A7 | CMPK2.S100A7 | CXCL1.SCD5 | DEFB4A.FOS |
| 6 | SCD5.VEGFA | CMPK2.SCD5 | IGFL1.SCD5 | UPP1v2.CMPK2 |
| 7 | IGFL1.CMPK2 | Genes with low expression | CMPK2.VEGFA | IGFL1.SCD5 |
| 8 | MMP1.S100A7 | FOS.SCD5 | IGFL1.RTP4 | IGFL1.DEFB4A |
| 9 | CMPK2.SCD5 | MMP1.CMPK2 | FOS.IRF7 | IGFL1.IRF7 |
| 10 | CXCL1.IRF7 | CXCL1.OAS3 | DEFB4A | UPP1v2.IRF7 |
| 11 | CMPK2.VEGFA | IGFL1.CMPK2 | DEFB4A.FOS | UPP1v2.SCD5 |
| 12 | CXCL1.OAS3 | SCD5.VEGFA | CMPK2.OAS3 | UPP1v2 |
| 13 | MMP1.SCD5 | MMP1.S100A7 | DEFB4A.RTP4 | UPP1v2.CXCL1 |
| 14 | CXCL1.CMPK2 | MMP1.SCD5 | CXCL1.OAS3 | IGFL1.RTP4 |
| 15 | MMP1.OAS3 | CXCL1.CMPK2 | UPP1v2.IRF7 | UPP1v2.DEFB4A |

TABLE 3

| Rank | rf | boosting | logit | lasso |
|---|---|---|---|---|
| 1 | IGFL1.COL5A2 | IL24.AADACL2 | SPP1 | PRKACA.SPP1 |
| 2 | IL24.AADACL2 | IGFL1.COL5A2 | COL5A2.AADACL2 | IGFL1.AADACL2 |
| 3 | PTCH1.CD68 | PRKACA.SPP1 | CD68.PRKACA | COL5A2 |
| 4 | PRKACA.SPP1 | AADACL2.MMP1 | PTCH1.MMP1 | IGFL1.SPP1 |
| 5 | AADACL2.MMP1 | AADACL2.SPP1 | IGFL1 | CD68.MMP1 |
| 6 | IGFL1.IL24 | PTCH1.CD68 | IGFL1.CD68 | COL5A2.CD68 |
| 7 | AADACL2.SPP1 | PRKACA.MMP1 | IGFL1.PTCH1 | PTCH1.SPP1 |
| 8 | IGFL1 | IGFL1.IL24 | IL24 | COL5A2.AADACL2 |
| 9 | PRKACA.MMP1 | IGFL1.PRKACA | AADACL2.CD68 | SPP1.MMP1 |
| 10 | IGFL1.PRKACA | AADACL2.CD68 | PTCH1.PRKACA | IGFL1.MMP1 |
| 11 | IGFL1.SPP1 | IL24.PRKACA | IGFL1.PRKACA | COL5A2.SPP1 |
| 12 | AADACL2.CD68 | SPP1.MMP1 | COL5A2.SPP1 | PTCH1.MMP1 |
| 13 | IL24.PRKACA | CD68.PRKACA | PTCH1 | IL24.CD68 |
| 14 | IGFL1.PTCH1 | COL5A2.AADACL2 | AADACL2.MMP1 | IGFL1.COL5A2 |
| 15 | IGFL1.AADACL2 | COL5A2.CD68 | PRKACA | IGFL1.CD68 |

In some embodiments, methods for differentiating cancer samples from non-cancer samples comprise detecting the gene expression levels of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, SPP1, or a combination thereof in cancer samples and non-cancer samples. In some instances, the cancer samples comprise basal cell carcinoma (BCC), squamous cell carcinoma (SCC), or a combination thereof. In some instances, the cancer samples comprise BCC and SCC. In some instances, the non-cancer samples comprise actinic keratosis (AK), seborrheic keratosis (SK), normal samples, or a combination thereof. In some instances, the non-cancer samples comprise actinic keratosis (AK), seborrheic keratosis (SK), and normal samples.

In some embodiments, the gene expression levels of IGFL1, MMP1, COL5A2, IL24, PTCH1, PRKACA, AADACL2, CD68, or SPP1 are upregulated in a skin disease, e.g., a non-melanoma skin cancer sample (optionally, BCC and/or SCC sample). In some instances, an upregulated gene expression level of IGFL1, MMP1, COL5A2, IL24, PTCH1, PRKACA, AADACL2, CD68, or SPP1, or a combination thereof are used to distinguish between a cancer sample from a non-cancer sample. For example, an upregulated gene expression level of IGFL1, MMP1, COL5A2, IL24, PTCH1, PRKACA, AADACL2, CD68, or SPP1, or a combination thereof are used to distinguish between BCC and/or SCC samples from AK, SK, normal sample or a combination thereof.

In some instances, BCC and SCC samples are compared to AK, SK, and normal samples. In some instances, BCC and SCC samples are compared to AK and SK samples. In some instances, BCC and SCC samples are compared to AK and normal samples. In some instances, BCC and SCC samples are compared SK and normal samples. In some instances, BCC and SCC samples are compared to AK samples. In some instances, BCC and SCC samples are compared to SK samples. In some instances, BCC and SCC samples are compared to normal samples. In some instances, BCC samples are compared to AK, SK, and normal samples. In some instances, BCC samples are compared to AK and normal samples. In some instances, BCC samples are compared to AK and SK samples. In some instances, BCC samples are compared to SK and normal samples. In some instances, BCC samples are compared to AK samples. In some instances, BCC samples are compared to SK samples. In some instances, BCC samples are compared to normal samples. In some instances, SCC samples are compared to AK, SK, and normal samples. In some instances, SCC samples are compared to AK and normal samples. In some instances, SCC samples are compared to AK and SK samples. In some instances, SCC samples are compared to SK and normal samples. In some instances, SCC samples are compared to AK samples. In some instances, SCC samples are compared to SK samples. In some instances, SCC samples are compared to normal samples. In some instances, BCC samples are compared to SCC samples.

In some embodiments, methods for differentiating cancer samples from non-cancer samples comprising detecting the gene expression levels of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, SPP1, or a combination thereof comprise improved specificity and sensitivity. In some embodiments, the specificity is at least or about 70%, 75%, 80%, 85%, 90%, or more than 95% when detecting the gene expression levels of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, SPP1, or a combination thereof. In some embodiments, the specificity is at least or about 70%, 75%, 80%, 85%, 90%, or more than 95% when detecting the gene expression levels of IGFL1, MMP1, COL5A2, IL24, AADACL2, PTCH1, CD68, PRKACA, SPP1, or a combination thereof. In some embodiments, the specificity is at least or about 70%, 75%, 80%, 85%, 90%, or more than 95% when detecting the gene expression levels of MMP1, S100A7, CMPK2, IRF7, IGFL1, CXCL1, UPP1, or a combination thereof. In some embodiments, the specificity is at least or about 70%, 75%, 80%, 85%, 90%, or more than 95% when detecting the gene expression levels of MMP1, S100A7, CMPK2, IRF7, IGFL1, CXCL1, or a combination thereof.

In some embodiments, the sensitivity is at least or about 70%, 75%, 80%, 85%, 90%, or more than 95% when detecting the gene expression levels of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, SPP1, or a combination thereof. In some embodiments, the sensitivity is at least or about 70%, 75%, 80%, 85%, 90%, or more than 95% when detecting the gene expression levels of IGFL1, MMP1, COL5A2, IL24, AADACL2, PTCH1, CD68, PRKACA, SPP1, or a combination thereof. In some embodiments, the sensitivity is at least or about 70%, 75%, 80%, 85%, 90%, or more than 95% when detecting the gene expression levels of MMP1, S100A7, CMPK2, IRF7, IGFL1, CXCL1, UPP1, or a combination thereof. In some embodiments, the sensitivity is at least or about 70%, 75%, 80%, 85%, 90%, or more than 95% when detecting the gene expression levels of MMP1, S100A7, CMPK2, IRF7, IGFL1, CXCL1, or a combination thereof.

In some embodiments, cancer samples are differentiated from non-cancer samples when amplification of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, SPP1, or a combination thereof is detected. In some embodiments, amplification of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, SPP1, or a combination thereof is not detected in non-cancer samples.

Various methods for detecting gene expression levels are contemplated herein. For example, a set of probes are used to detect at least two of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In some cases, no more than 3, 4, 5, 6, 7, 8, 9, 10, 15, 20, or 22 genes are detected. In some instances, a set of probes are used to detect at least three of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In some instances, a set of probes are used to detect at least four of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In some instances, a set of probes are used to detect at least five of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In some instances, a set of probes are used to detect at least six of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In some instances, a set of probes are used to detect at least seven of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In some instances, a set of probes are used to detect at least eight of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In some instances, a set of probes are used to detect at least nine of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In some instances, a set of probes are used to detect at least ten of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In some instances, a set of probes are used to detect at least eleven of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In some instances, a set of probes are used to detect at least twelve of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In some instances, a set of probes are used to detect all of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1.

In some embodiments, the set of probes are used to detect at least the gene expression levels of at least two of IGFL1, MMP1, COL5A2, IL24, AADACL2, PTCH1, CD68, PRKACA, and SPP1. In some cases, no more than 3, 4, 5, 6, 7, 8, or 9 genes are detected. In some cases, the set of probes are used to detect at least the gene expression levels of at least three of IGFL1, MMP1, COL5A2, IL24, AADACL2, PTCH1, CD68, PRKACA, and SPP1. In some cases, the set of probes are used to detect at least the gene expression levels of at least four of IGFL1, MMP1, COL5A2, IL24, AADACL2, PTCH1, CD68, PRKACA, and SPP1. In some cases, the set of probes are used to detect at least the gene expression levels of at least five of IGFL1, MMP1, COL5A2, IL24, AADACL2, PTCH1, CD68, PRKACA, and SPP1. In some cases, the set of probes are used to detect at least the gene expression levels of at least six of IGFL1, MMP1, COL5A2, IL24, AADACL2, PTCH1, CD68, PRKACA, and SPP1. In some cases, the set of probes are used to detect at least the gene expression levels of IGFL1, MMP1, COL5A2, IL24, AADACL2, PTCH1, CD68, PRKACA, and SPP1.

In some embodiments, the set of probes are used to detect at least the gene expression levels of at least two of MMP1, S100A7, CMPK2, IRF7, IGFL1, CXCL1, and UPP1. In some embodiments, the set of probes are used to detect at least three of MMP1, S100A7, CMPK2, IRF7, IGFL1, CXCL1, and UPP1. In some embodiments, the set of probes are used to detect at least four of MMP1, S100A7, CMPK2, IRF7, IGFL1, CXCL1, and UPP1. In some embodiments, the set of probes are used to detect at least five of MMP1, S100A7, CMPK2, IRF7, IGFL1, CXCL1, and UPP1. In some embodiments, the set of probes are used to detect at least six of MMP1, S100A7, CMPK2, IRF7, IGFL1, CXCL1, and UPP1. In some embodiments, the set of probes are used to detect all of MMP1, S100A7, CMPK2, IRF7, IGFL1, CXCL1, and UPP1.

In some embodiments, the set of probes are used to detect the gene expression levels of at least two of MMP1, S100A7, CMPK2, IRF7, IGFL1, and CXCL1. In some embodiments, the set of probes are used to detect at least three of MMP1, S100A7, CMPK2, IRF7, IGFL1, and CXCL1. In some embodiments, the set of probes are used to detect at least four of MMP1, S100A7, CMPK2, IRF7, IGFL1, and CXCL1. In some embodiments, the set of probes are used to detect at least five of MMP1, S100A7, CMPK2, IRF7, IGFL1, and CXCL1. In some embodiments, the set of probes are used to detect of all of MMP1, S100A7, CMPK2, IRF7, IGFL1, and CXCL1.

In some embodiments, the set of probes comprises polynucleotides. In some instances, the set of probes comprises polynucleotides for two different exons of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, or SPP1. In some instances, the gene expression levels are detected following hybridization of the set of probes to at least two of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In some embodiments, the set of probes detects RNA. In some embodiments, the set of probes detects mRNA. In some embodiments, the set of probes detects DNA.

Probes for detecting gene expression levels of at least two of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, or SPP1, in certain embodiments, are used for an amplification reaction. In some embodiments, the amplification reaction is PCR. In some embodiments, the amplification reaction is quantitative such as qPCR. In some embodiments, the PCR reaction utilizes a TaqMan™ or a similar quantitative PCR technology.

In some embodiments, a number of probes in the set of probes is at least or about 1, 2, 3, 5, 6, 7, 8, 9, 10, 11, 12, 13, 14, 15, 16, 17, 18, 19, 20, 25, 30, or more than 30 probes. In some embodiments, the number of probes in the set of probes is about 6 probes. In some embodiments, the number of probes in the set of probes is about 7 probes. In some embodiments, the number of probes in the set of probes is about 8 probes. In some embodiments, the number of probes in the set of probes is about 9 probes. In some embodiments, the number of probes in the set of probes is about 13 probes.

In some embodiments, the set of probes comprises one or more primer pairs. In some embodiments, a number of primer pairs is at least or about 1, 2, 3, 5, 6, 7, 8, 9, 10, 11, 12, 13, 14, 15, 16, 17, 18, 19, 20, 25, 30, or more than 30 primer pairs. In some embodiments, the number of primer pairs is about 6 primer pairs. In some embodiments, the number of primer pairs is about 7 primer pairs. In some embodiments, the number of primer pairs is about 13 primer pairs.

In some embodiments, one or more probes in the set of probes is labeled. In some embodiments, the one or more probe is labeled with a radioactive label, a fluorescent label, an enzyme, a chemiluminescent tag, a colorimetric tag, an affinity tag or other labels or tags that are known in the art.

Exemplary affinity tags include, but are not limited to, biotin, desthiobiotin, histidine, polyhistidine, myc, hemagglutinin (HA), FLAG, glutathione S transferase (GST), or derivatives thereof. In some embodiments, the affinity tag is recognized by avidin, streptavidin, nickel, or glutathione.

In some embodiments, the fluorescent label is a fluorophore, a fluorescent protein, a fluorescent peptide, quantum dots, a fluorescent dye, a fluorescent material, or variations or combinations thereof.

Exemplary fluorophores include, but are not limited to, Alexa-Fluor dyes (e.g., Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor®700, and Alexa Fluor® 750), APC, Cascade Blue, Cascade Yellow and R-phycoerythrin (PE), DyLight 405, DyLight 488, DyLight 550, DyLight 650, DyLight 680, DyLight 755, DyLight 800, FITC, Pacific Blue, PerCP, Rhodamine, and Texas Red, Cy5, Cy5.5, Cy7.

Examples of fluorescent peptides include GFP (Green Fluorescent Protein) or derivatives of GFP (e.g., EBFP, EBFP2, Azurite, mKalamal, ECFP, Cerulean, CyPet, YFP, Citrine, Venus, and YPet.

Examples of fluorescent dyes include, but are not limited to, xanthenes (e.g., rhodamines, rhodols and fluoresceins, and their derivatives); bimanes; coumarins and their derivatives (e.g., umbelliferone and aminomethyl coumarins); aromatic amines (e.g., dansyl; squarate dyes); benzofurans; fluorescent cyanines; indocarbocyanines; carbazoles; dicyanomethylene pyranes; polymethine; oxabenzanthrane; xanthene; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; and derivatives of such dyes. In some embodiments, the fluorescein dye is, but not limited to, 5-carboxyfluorescein, fluorescein-5-isothiocyanate, fluorescein-6-isothiocyanate and 6-carboxyfluorescein. In some embodiments, the rhodamine dye is, but not limited to, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, and rhodamine 101 sulfonyl chloride (sold under the tradename of TEXAS RED®). In some embodiments, the cyanine dye is Cy3, Cy3B, Cy3.5, Cy5, Cy5.5, Cy7, IRDYE680, Alexa Fluor 750, IRDye800CW, or ICG.

In some embodiments, the gene expression levels of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, SPP1, or a combination thereof is measured using PCR. Examples of PCR techniques include, but are not limited to quantitative PCR (qPCR), single cell PCR, PCR-RFLP, digital PCR (dPCR), droplet digital PCR (ddPCR), single marker qPCR, hot start PCR, and Nested PCR.

In some embodiments, the expression levels are measured using qPCR. In some embodiments, the qPCR comprises use of fluorescent dyes or fluorescent probes. In some embodiments, the fluorescent dye is an intercalating dye. Examples of intercalating dyes include, but are not limited to, intercalating dyes include SYBR green I, SYBR green II, SYBR gold, ethidium bromide, methylene blue, Pyronin Y, DAPI, acridine orange, Blue View, or phycoerythrin. In some embodiments, the qPCR comprises use of more than one fluorescent probe. In some embodiments, the use of more than one fluorescent probes allows for multiplexing. For example, different non-classical variants are hybridized to different fluorescent probes and can be detected in a single qPCR reaction.

Methods and compositions described herein, in some embodiments, further comprise detecting a mutational change in a gene of interest. In some instances, the mutational change is detected in TERT, CDKN2A, TP53, PTCH1, or a combination thereof. In some instances, the mutational change is detected in TERT. In some instances, the mutational change is detected in CDKN2A. In some instances, the mutational change is detected in TP53. In some instances, the mutational change is detected in PTCH1. Exemplary amino acid sequences for TERT, CDKN2A, TP53, and PTCH11 are illustrated in Table 4.

TABLE 4

| SEQ ID NO | Gene Name | Accession Number | Amino Acid Sequence |
|---|---|---|---|
| 1 | TP53 | P04637 | MEEPQSDPSVEPPLSQETFSDLWKLLPENNVLSPLPSQA MDDLMLSPDDIEQWFTEDPGPDEAPRMPEAAPPVAPAPA APTPAAPAPAPSWPLSSSVPSQKTYQGSYGFRLGFLHSG TAKSVTCTYSPALNKMFCQLAKTCPVQLWVDSTPPPGTR VRAMAIYKQSQHMTEVVRRCPHHERCSDSDGLAPPQHLI RVEGNLRVEYLDDRNTFRHSVVVPYEPPEVGSDCTTIHY NYMCNSSCMGGMNRRPILTIITLEDSSGNLLGRNSFEVR VCACPGRDRRTEEENLRKKGEPHHELPPGSTKRALPNNT SSSPQPKKKPLDGEYFTLQIRGRERFEMFRELNEALELK DAQAGKEPGGSRAHSSHLKSKKGQSTSRHKKLMFKTEGP DSD |
| 2 | TERT | O14746 | MPRAPRCRAVRSLLRSHYREVLPLATFVRRLGPQGWRLV QRGDPAAFRALVAQCLVCVPWDARPPPAAPSFRQVSCLK ELVARVLQRLCERGAKNVLAFGFALLDGARGGPPEAFTT SVRSYLPNTVTDALRGSGAWGLLLRRVGDDVLVHLLARC ALFVLVAPSCAYQVCGPPLYQLGAATQARPPPHASGPRR RLGCERAWNHSVREAGVPLGLPAPGARRRGGSASRSLPL PKRPRRGAAPEPERTPVGQGSWAHPGRTRGPSDRGFCVV SPARPAEEATSLEGALSGTRHSHPSVGRQHHAGPPSTSR PPRPWDTPCPPVYAETKHFLYSSGDKEQLRPSFLLSSLR PSLTGARRLVETIFLGSRPWMPGTPRRLPRLPQRYWQMR PLFLELLGNHAQCPYGVLLKTHCPLRAAVTPAAGVCARE KPQGSVAAPEEEDTDPRRLVQLLRQHSSPWQVYGFVRAC LRRLVPPGLWGSRHNERRFLRNTKKFISLGKHAKLSLQE LTWKMSVRDCAWLRRSPGVGCVPAAEHRLREEILAKFLH WLMSVYVVELLRSFFYVTETTFQKNRLFFYRKSVWSKLQ SIGIRQHLKRVQLRELSEAEVRQHREARPALLTSRLRFI PKPDGLRPIVNMDYVVGARTFRREKRAERLTSRVKALFS VLNYERARRPGLLGASVLGLDDIHRAWRTFVLRVRAQDP PPELYFVKVDVTGAYDTIPQDRLTEVIASIIKPQNTYCV RRYAVVQKAAHGHVRKAFKSHVSTLTDLQPYMRQFVAHL QETSPLRDAVVIEQSSSLNEASSGLFDVFLRFMCHHAVR IRGKSYVQCQGIPQGSILSTLLCSLCYGDMENKLFAGIR RDGLLLRLVDDFLLVTPHLTHAKTFLRTLVRGVPEYGCV VNLRKTVVNFPVEDEALGGTAFVQMPAHGLFPWCGLLLD TRTLEVQSDYSSYARTSIRASLTFNRGFKAGRNMRRKLF GVLRLKCHSLFLDLQVNSLQTVCTNIYKILLLQAYRFHA CVLQLPFHQQVWKNPTFFLRVISDTASLCYSILKAKNAG MSLGAKGAAGPLPSEAVQWLCHQAFLLKLTRHRVTYVPL LGSLRTAQTQLSRKLPGTTLTALEAAANPALPSDFKTIL D |
| 3 | PTCH1 (isoform L) | Q13635 | MASAGNAAEPQDRGGGGSGCIGAPGRPAGGGRRRRTGGL RRAAAPDRDYLHRPSYCDAAFALEQISKGKATGRKAPLW LRAKFQRLLFKLGCYIQKNCGKFLVVGLLIFGAFAVGLK AANLETNVEELWVEVGGRVSRELNYTRQKIGEEAMFNPQ LMIQTPKEEGANVLTTEALLQHLDSALQASRVHVYMYNR QWKLEHLCYKSGELITETGYMDQIIEYLYPCLIITPLDC FWEGAKLQSGTAYLLGKPPLRWTNFDPLEFLEELKKINY QVDSWEEMLNKAEVGHGYMDRPCLNPADPDCPATAPNKN STKPLDMALVLNGGCHGLSRKYMHWQEELIVGGTVKNST GKLVSAHALQTMFQLMTPKQMYEHFKGYEYVSHINWNED KAAAILEAWQRTYVEVVHQSVAQNSTQKVLSFTTTTLDD ILKSFSDVSVIRVASGYLLMLAYACLTMLRWDCSKSQGA |

TABLE 4-continued

| SEQ ID NO | Gene Name | Accession Number | Amino Acid Sequence |
|---|---|---|---|
| | | | VGLAGVLLVALSVAAGLGLCSLIGISFNAATTQVLPFLA<br>LGVGVDDVFLLAHAFSETGQNKRIPFEDRTGECLKRTGA<br>SVALTSISNVTAFFMAALIPIPALRAFSLQAAVVVVFNF<br>AMVLLIFPAILSMDLYRREDRRLDIFCCFTSPCVSRVIQ<br>VEPQAYTDTHDNTRYSPPPPYSSHSFAHETQITMQSTVQ<br>LRTEYDPHTHVYYTTAEPRSEISVQPVTVTQDTLSCQSP<br>ESTSSTRDLLSQFSDSSLHCLEPPCTKWTLSSFAEKHYA<br>PFLLKPKAKVVVIFLFLGLLGVSLYGTTRVRDGLDLTDI<br>VPRETREYDFIAAQFKYFSFYNMYIVTQKADYPNIQHLL<br>YDLHRSFSNVKYVMLEENKQLPKMWLHYFRDWLQGLQDA<br>FDSDWETGKIMPNNYKNGSDDGVLAYKLLVQTGSRDKPI<br>DISQLTKQRLVDADGIINPSAFYIYLTAWVSNDPVAYAA<br>SQANIRPHRPEWVHDKADYMPETRLRIPAAEPIEYAQFP<br>FYLNGLRDTSDFVEAIEKVRTICSNYTSLGLSSYPNGYP<br>FLFWEQYIGLRHWLLLFISVVLACTFLVCAVFLLNPWTA<br>GIIVMVLALMTVELFGMMGLIGIKLSAVPVVILIASVGI<br>GVEFTVHVALAFLTAIGDKNRRAVLALEHMFAPVLDGAV<br>STLLGVLMLAGSEFDFIVRYFFAVLAILTILGVLNGLVL<br>LPVLLSFFGPYPEVSPANGLNRLPTPSPEPPPSVVRFAM<br>PPGHTHSGSDSSDSEYSSQTTVSGLSEELRHYEAQQGAG<br>GPAHQVIVEATENPVFAHSTVVHPESRHHPPSNPRQQPH<br>LDSGSLPPGRQGQQPRRDPPREGLWPPPYRPRRDAFEIS<br>TEGHSGPSNRARWGPRGARSHNPRNPASTAMGSSVPGYC<br>QPITTVTASASVTVAVHPPPVPGPGRNPRGGLCPGYPET<br>DHGLFEDPHVPFHVRCERRDSKVEVIELQDVECEERPRG<br>SSSN |
| 4 | PTCH1 (isoform S) | NP_001077074.1 | MFNPQLMIQTPKEEGANVLTTEALLQHLDSALQASRVHV<br>YMYNRQWKLEHLCYKSGELITETGYMDQIIEYLYPCLII<br>TPLDCFWEGAKLQSGTAYLLGKPPLRWTNFDPLEFLEEL<br>KKINYQVDSWEEMLNKAEVGHGYMDRPCLNPADPDCPAT<br>APNKNSTKPLDMALVLNGGCHGLSRKYMHWQEELIVGGT<br>VKNSTGKLVSAHALQTMFQLMTPKQMYEHFKGYEYVSHI<br>NWNEDKAAAILEAWQRTYVEVVHQSVAQNSTQKVLSFTT<br>TTLDDILKSFSDVSVIRVASGYLLMLAYACLTMLRWDCS<br>KSQGAVGLAGVLLVALSVAAGLGLCSLIGISFNAATTQV<br>LPFLALGVGVDDVFLLAHAFSETGQNKRIPFEDRTGECL<br>KRTGASVALTSISNVTAFFMAALIPIPALRAFSLQAAVV<br>VVFNFAMVLLIFPAILSMDLYRREDRRLDIFCCFTSPCV<br>SRVIQVEPQAYTDTHDNTRYSPPPPYSSHSFAHETQITM<br>QSTVQLRTEYDPHTHVYYTTAEPRSEISVQPVTVTQDTL<br>SCQSPESTSSTRDLLSQFSDSSLHCLEPPCTKWTLSSFA<br>EKHYAPFLLKPKAKVVVIFLFLGLLGVSLYGTTRVRDGL<br>DLTDIVPRETREYDFIAAQFKYFSFYNMYIVTQKADYPN<br>IQHLLYDLHRSFSNVKYVMLEENKQLPKMWLHYFRDWLQ<br>GLQDAFDSDWETGKIMPNNYKNGSDDGVLAYKLLVQTGS<br>RDKPIDISQLTKQRLVDADGIINPSAFYIYLTAWVSNDP<br>VAYAASQANIRPHRPEWVHDKADYMPETRLRIPAAEPIE<br>YAQFPPFYLNGLRDTSDFVEAIEKVRTICSNYTSLGLSSY<br>PNGYPFLFWEQYIGLRHWLLLFISVVLACTFLVCAVFLL<br>NPWTAGIIVMVLALMTVELFGMMGLIGIKLSAVPVVILI<br>ASVGIGVEFTVHVALAFLTAIGDKNRRAVLALEHMFAPV<br>LDGAVSTLLGVLMLAGSEFDFIVRYFFAVLAILTILGVL<br>NGLVLLPVLLSFFGPYPEVSPANGLNRLPTPSPEPPPSV<br>VRFAMPPGHTHSGSDSSDSEYSSQTTVSGLSEELRHYEA<br>QQGAGGPAHQVIVEATENPVFAHSTVVHPESRHHPPSNP<br>RQQPHLDSGSLPPGRQGQQPRRDPPREGLWPPPYRPRRD<br>AFEISTEGHSGPSNRARWGPRGARSHNPRNPASTAMGSS<br>VPGYCQPITTVTASASVTVAVHPPPVPGPGRNPRGGLCP<br>GYPETDHGLFEDPHVPFHVRCERRDSKVEVIELQDVECE<br>ERPRGSSSN |
| 5 | CDKN2A | P42771 | MEPAAGSSMEPSADWLATAAARGRVEEVRALLEAGALPN<br>APNSYGRRPIQVMMMGSARVAELLLLHGAEPNCADPATL<br>TRPVHDAAREGFLDTLVVLHRAGARLDVRDAWGRLPVDL<br>AEELGHRDVARYLRAAAGGTRGSNHARIDAAEGPSDIPD |

TERT, also known as Telomerase Reverse Transcriptase or Telomerase-Associated Protein 2, encodes the TERT protein. The TERT protein is the catalytic subunit of the protein telomerase. In some instances, a mutation in TERT is correlated with a non-melanoma skin cancer (e.g., BCC and/or SCC). In some instances, a mutation is in the TERT promoter. In some instances, a mutation is at least or about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, or more than 200 base pairs upstream of the translation start site of the TERT promoter. In some instances, one or more mutations are in the TERT promoter. In some instances, the one or more mutations in the TERT promoter are a G to A mutation. In some instances, the one or more mutations in the TERT promoter are a T to G mutation. In some instances, the one or more mutations in the TERT promoter are a C to T mutation. In some instances, one or more mutations in the TERT promoter result in increased expression of TERT. In some instances, one or more mutations in the TERT promoter result in increased expression or activity of TERT protein.

Exemplary mutations in TERT include, but not limited to, 1,295,228 C>T (C228T) and 1,295,250 C>T (C250T). In some instances, C228T is a mutation corresponding to −124 C>T from the translation start site in the TERT promoter. In some instances, C250T is a mutation corresponding to −146 C>T from the translation start site in the TERT promoter. In some instances, a mutation is a nucleotide sequence of TERT. For example, the mutation in the nucleotide sequence includes, but not limited to, 571A>G, 648G>T, 1127C>T, 1135T>C, 1216G>A, 1217G>A, 1281C>T, 1284G>A, 1405C>T, 1461C>T, 1529G>A, 1541T>A, 1566G>A, 1689C>T, 1695G>A, 1782G>A, 1831G>A, 1841C>T, 1882G>A, 1928G>A, 2009C>A, 2067C>T, 2152G>A, 2162C>G, 2163C>T, 2178G>A, 2208G>A, 2254C>A, 2262C>G, 2271G>A, 2272G>A, 2283C>T, 2328C>T, 2361G>A, 2391C>T, 2405G>A, 2436C>T, 2456G>A, 2472C>T, 2499G>A, 2508C>A, 2568G>A, 2589C>T, 2633C>T, 2640G>A, 2725G>A, 2750C>T, 2755T>A, 2758G>A, 2773C>T, 2784C>T, 2786C>T, 2896G>A, 3015C>T, 3057C>T, 3084C>A, 3096C>T, 3097C>T, 3139C>T, 3198C>T, 3200C>T, 3284C>G, 3345G>A, 3363G>A, 1-100C>T, 1-101C>T, 1-101_1-100CC>TT, 1-106_1-105CC>TT, 1-111C>T, 1-124C>A, 1-124C>T, 1-125C>T, 1-125_1-124CC>TT, 1-126C>T, 1-126_1-124CCC>TTT, 1-126_1-125CC>TT, 1-127_1-126CC>TT, 1-139_1-138CC>TT, 1-144C>T, 1-145C>T, 1-146C>T, 1-149C>T, 1-150C>T, 1-154C>T, 1-156C>T, 1-156C>T, 1-159C>T, 1-176C>T, 1-187C>T, 1-242C>T, 1-46C>T, 1-57A>C, 1-58C>T, 1-90_1-89GC>TT, and 1-91C>T.

In some instances, a mutation in TERT is in exon 1, 2, 3, 4, 5, 6, 7, 8, 9, 10, 11, 12, 13, 14, 15, 16, or a combination thereof of TERT. In some instances, a mutation in TERT is a mutation in a peptide sequence. In some instances, the mutation results in a missense substitution, a nonsense substitution (*), a coding silent substitution, deletion (del), an insertion (ins), or a frameshift (fs). Exemplary mutations include, but are not limited to, S191G, L216L, P376L, L379L, G406R, G406E, A427A, R428R, L469L, F487F, W510*, V514E, R522R, V563V, E565E, K594K, E611K, P614L, D628N, R643K, A670E, A689A, D718N, P721R, P721P, T726T, Q736Q, H752N, H754Q, K757K, A758T, S761S, F776F, R787R, S797S, S802N, F812F, R819H, S824S, Q833Q, I836I, G856G, L863L, T878I, A880A, V909I, T917M, F919I, V920I, H925Y, F928F, P929L, A966T, L1005L, L1019L, N1028K, F1032F, L1033L, A1040T, L1047L, P1066P, S1067F, S1095*, L1115L, and P1121P. In some cases, the mutation(s) are at the corresponding residue positions as set forth in SEQ ID NO: 2.

The gene CDKN2A, also known as cyclin-dependent kinase inhibitor 2A, encodes two proteins p16$^{INK4a}$ and p14$^{ARF}$. p16$^{INK4a}$ is transcribed from exon 1α and p14$^{ARF}$ is transcribed from exon 1 and both genes are involved in cellular senescence. In some instances, a mutation in CDKN2A is correlated with a non-melanoma skin cancer (e.g., BCC and/or SCC). In some instances, a mutation is a nucleotide sequence of CDKN2A. For example, the mutation in the nucleotide sequence includes, but not limited to, 1_471del471, 4G>A, 9_32del24, 10G>T, 12G>A, 42C>G, 44G>A, 45G>A, 47_50delTGGC, 58G>C, 66_67GG>AA, 68delG, 83T>G, 92T>C, 95_112del18, 97G>T, 104G>A, 104G>T, 106delG, 107C>G, 109C>T, 113C>T, 128_129delGT, 132delC, 142_143CC>TT, 143C>T, 144G>A, 147_148CC>AT, 147_148CC>TT, 148C>T, 151_457del307, 158_159delTG, 161T>A, 163G>C, 164G>A, 166_167insA, 168_169insG, 169_170GC>TT, 170C>T, 170_172CCC>TTT, 171C>T, 171_172CC>TT, 171_178delCCGAGTGG, 172C>T, 172_173insC, 172_179delCGAGTGGC, 172delC, 176T>G, 179C>T, 179_180insC, 181G>T, 181_202>AC, 185T>C, 188T>C, 192G>A, 194T>C, 196_198CAC>TAG, 198_199insA, 199G>A, 202G>A, 203_204delCG, 203delC, 204G>A, 205G>T, 209C>T, 212A>T, 215G>A, 218C>T, 219C>T, 222C>A, 223C>T, 223_224CC>T, 225_243del19, 227C>T, 236C>T, 237C>T, 237_238CC>TT, 238C>T, 238_247del10, 239G>A, 241C>T, 242C>A, 242C>T, 242_243CC>TT, 243_244ins19, 243_244insC, 244G>A, 245T>A, 245T>C, 247C>G, 247C>T, 248A>G, 248A>T, 248_249AC>CT, 249C>G, 250G>A, 250_270del21, 254C>T, 257_259delCCC, 259C>T, 259delC, 260G>A, 261_262GG>AA, 262G>A, 262G>T, 264_265GG>AA, 266delG, 268T>C, 270C>T, 286_294del9, 290T>C, 290T>G, 290_294delTGCAC, 295C>T, 297G>A, 297_298GC>AC, 299C>T, 301G>T, 304G>A, 305C>T, 311T>G, 319C>T, 320G>A, 329G>A, 329_330GG>AA, 330G>A, 331G>A, 334C>G, 335G>C, 341C>A, 341C>T, 341_342CC>TT, 342C>T, 346G>T, 346_347insG, 370C>T, 371G>A, 373G>A, 373_374insCG, 377T>A, 380delC, 386_387AC>TT, 387C>G, 389T>G, 406G>A, 413G>A, 442G>A, 443C>G, 457G>A, 470G>C, 1_150del150, 1_457del457, 151-1_151GG>AA, 151_151G>A, 151_457del307, 151_457del321, 458_471del14, (199_204)delG, 150+15T>C, 150+1G>A, 150+2T>C, 150+8G>C, 151-1G>A, 151-1G>T, 151-2A>G, 151-2A>T, 151-42C>T, 457+1G>A, and 458-2A>G.

In some instances, mutations in CDKN2A comprise deletions and/or mutations throughout the coding region. In some instances, a mutation in CDKN2A is in exon 1, 2, 3, 4, 5, 6, 7, 8, or a combination thereof of CDKN2A.

In some instances, a mutation in CDKN2A is a mutation in a peptide sequence. In some instances, the mutation results in a missense substitution, a nonsense substitution (*), a coding silent substitution, deletion (del), an insertion (ins), or a frameshift (fs). Exemplary mutations include, but are not limited to, E2K, P3_P11del, A4S, A4A, D14E, W15*, W15*, L16fs*9, A20P, G23S, G23fs*3, R24P, V28G, L31P, L32_L37del, L32_L37del, E33*, G35E, G35V, A36fs*17, A36G, A36T, L37L, P38L, S43fs*76, Y44fs*1, P48L, P48L, P48P, P48L, I49M, Q50*, Q50*, Q50*, Q50*, V5ifs, M53I, M53fs*66, M54K, M54R, G55R, G55D, S56fs*64, A57fs*63, A57F, A57V, A57_R58>V*, A57A, R58*, R58fs*59, R58*, R58fs*62, R58fs*59, R58fs*88, R58*, V59G, A60V, A60fs*, E61fs*59, E61*, E61fs*52, L62P, L63P, L64L, L65P, H66*, G67*, G67fs*53, G67S, A68T, A68fs*51, A68fs*78, A68A, E69*, P70L, N71I, C72Y, A73V, A73A, D74E, P75S, P75fs*71, A76fs*64, A76V, T79I, T79T, R80*, R80*, R80fs*63, R80Q, R80*, R80, P81S, P81H, P81L, P81L, P81L, V82fs*44, V82fs*38, V82M, V82E, V82A, H83D, H83Y, H83R, H83L, H83P, H83Q, H83N, H83Y, D84N, D84_F90del, A85V, A86_R87>G, R87W, R87fs*59, R87Q, E87K, E88K, E88*, E88*, G89S, G89fs*57, F90L, F90F, V96_H98del, L97P, L97R, L97fs*21, R99W, R99R, A100P, A100V, G101W, G101W, A102T, A102V, L104R, R107C, R107H, A109V, W110*, W110*, W110*, W110*, G111S, R112G, R112P, P114H, P114L, P114L, P114P, P114L, D116Y, D116fs*4, R124C, R124H, D125N, D125fs*22, V126D, V126D, A127fs*19, Y129F, Y129*, L130R, L130R, G136S, R138K, A148T, A148G, D153N, and *157S. In some cases, the mutation(s) are at the corresponding residue positions as set forth in SEQ ID NO: 5.

In some instances, CDKN2A comprises one or more mutations in the protein region QVMMMGSARVAEL-LLLHGAEPNCADPATL-TRPVHDAAREGFLDTLVVLHRAGARLDVRDAW GRLPVDLAEELGHRDVARYLRAAAGGTRGSN-HARIDAAEGPS (SEQ ID NO: 6). In some cases, CDKN2A comprises a mutation at V5ifs, M53I, R58*, E61*, G67*, E69*, or R80*, or a combination thereof, in which fs denotes frameshift and (*) denotes nonsense substitution.

TP53, also known as p53, cellular tumor antigen p53, phosphoprotein p53, tumor suppressor p53, antigen NY-CO-13, or transformation-related protein 53 (TRP53), encodes the tumor protein p53 (TP53). TP53 is a phosphoprotein made of 393 amino acids and comprises four domains. TP53 plays a role in cell cycle control and apoptosis. In some instances, a mutation in TP53 is associated with a non-melanoma skin cancer (e.g., BCC and/or SCC). In some instances, a mutation is a nucleotide sequence of TP53. For example, the mutation in the nucleotide sequence includes, but not limited to, 96+1G>A, 96+1G>T, 97-1G>A, 375+1G>A, 375+2T>C, 375_375+1GG>AT, 376-1G>A, 376-1G>T, 559+1G>A, 559+2T>G, 560-1G>A, 560-1G>T, 560-1_560GG>AA, 560-2A>C, 672+1G>A, 673-1G>A, 673-8T>A, 782+1G>C, 782_782+1GG>AA, 783-2A>T, 919+1G>A, 920-1G>T, 993+1G>A, 994-1G>A, 19G>C, 31G>A, 37C>T, 69G>A, 79C>T, 101C>T, 102C>G, 136T>C, 139_140delCC, 140delC, 142G>A, 151G>T, 158G>A, 159G>A, 159G>C, 162C>T, 166G>T, 173delC, 175_176GG>AA, 181G>A, 202G>A, 206C>T, 211C>T, 212C>T, 214C>G, 214C>T, 215C>G, 216_217insC, 217G>A, 229C>T, 238C>T, 239C>T, 242C>T, 242delC, 245C>T, 248C>A, 250G>A, 250_251insT, 251C>T, 251_252CC>TT, 253C>T, 254C>T, 257_279del23, 265C>T, 265_266CC>TT, 266C>T, 269C>T, 272G>A, 273G>A, 275C>T, 281C>T, 284C>T, 287C>T, 289G>A, 292C>T, 293C>T, 296C>T, 298C>T, 305C>T, 309C>G, 310C>T, 312delG, 313delG, 321C>A, 321C>G, 322G>A, 325_330delTTCCGT, 326T>C, 327_328CC>TT, 328C>T, 328delC, 332T>A, 349delG, 358A>G, 365_367delTGA, 375G>A, 375G>T, 380C>T, 380_381CC>TT, 382C>T, 386C>T, 388C>T, 388delC, 394C>A, 394A>G, 395A>T, 396G>T, 398T>A, 400T>C, 403T>C, 404G>A, 404G>C, 405C>A, 405_406CC>TT, 406C>T, 409C>A, 412delG, 413C>T, 413_414CC>TT, 415A>T, 416delA, 417G>C, 418_419insA, 419C>T, 424C>T, 424_425CC>TT, 425C>T, 428T>A, 428T>G, 430delC, 432G>A, 434_435TG>GT, 437G>A, 438G>A, 442_465del24, 446C>T, 447C>T, 449C>T, 451C>T, 452C>A, 452_453CC>TT, 453C>T, 453_454insN, 454C>T, 454_455CC>TT, 455C>G, 455C>T, 457_461delCCCGG, 456_457insC, 459_460insN, 463_464delAC, 465C>T, 466C>T, 466delC, 467G>C, 468_469delCG, 468_487del20, 469G>A, 469G>T, 471_472CC>TT, 472C>T, 474C>T, 475G>A, 476C>T, 476_477CC>TT, 477C>T, 480G>A, 480G>C, 481G>A, 482C>T, 483C>T, 487T>C, 487T>G, 493C>T, 496T>G, 502C>T, 502_503insN, 502_511del10, 507G>A, 508A>G, 509C>T, 511G>C, 513delG, 517G>A, 517G>C, 518T>G, 521G>A, 522G>C, 524G>A, 527G>A, 527G>T, 528C>G, 529C>T, 529_530CC>TT, 530C>T, 530_531CC>AT, 530_531CC>TT, 528delC, 531_532CC>TT, 532C>A, 532C>T, 532_533insN, 534_535CC>AT, 534_535CC>TT, 535C>A, 535C>T, 536A>T, 541C>T, 542C>A, 546C>T, 548C>A, 548C>T, 550G>A, 556G>A, 559G>A, 565G>A, 565_591del27, 566C>T, 567C>T, 568C>T, 568_569CC>TT, 569C>T, 571C>T, 572C>T, 573T>A, 574C>T, 580C>T, 581T>G, 582_586delTATCC, 583A>T, 585_586CC>TT, 586C>T, 587G>T, 590T>A, 592G>A, 592G>T, 599delA, 600_601insN, 601T>G, 603_604GC>TT, 603_604insAAATTTG, 605G>C, 605G>T, 605_606GT>CG, 606delT, 613T>G, 614A>G, 617T>A, 620_627delATGACAGA, 622G>T, 626G>A, 626_627delGA, 632C>T, 637C>T, 638G>A, 638G>C, 640_647delCATAGTGT, 645T>G, 647T>G, 652G>A, 653T>A, 653T>G, 656C>T, 656_657CC>TT, 658T>A, 659A>G, 660_661insN, 662_672+40del51, 664_665CC>TT, 665C>T, 666G>C, 667delC, 670G>T, 674T>C, 677G>A, 677G>C, 680C>T, 682G>A, 683A>C, 685_686delTG, 688A>G, 689C>T, 690C>A, 691A>T, 697delC, 700T>A, 700T>C, 701A>C, 702C>A, 703A>G, 704A>G, 704A>T, 706T>A, 706T>C, 712T>A, 713G>A, 713G>T, 714T>G, 721T>C, 722C>T, 722_723CC>TT, 723C>T, 724T>A, 724T>G, 725G>A, 726C>T, 727A>T, 728T>G, 730G>A, 733G>A, 733G>T, 733_734GG>AA, 734G>A, 734G>T, 737T>C, 737T>G, 738G>A, 739A>T, 740A>C, 741_742CC>TT, 742C>T, 742_744CGG>TGC, 743G>A, 743G>C, 743G>T, 743_744GG>AA, 744G>A, 745A>T, 745_768del24, 746G>C, 746G>T, 747G>C, 747G>T, 748C>G, 748C>T, 748_749CC>TT, 749C>T, 749_750CC>TG, 750C>T, 752T>A, 755T>C, 756C>T, 757A>G, 758C>T, 759C>T, 762delC, 770T>C, 771_772GG>AA, 772G>A, 775delG, 776A>T, 781A>T, 791delT, 794T>C, 795G>A, 795_796GG>AA, 796G>A, 796G>T, 796_797GG>AA, 797G>A, 799C>T, 800G>C, 806G>A, 808T>A, 811G>A, 812_815delAGGT, 814G>A, 815T>A, 815T>G, 817C>G, 817C>T, 817_825delCGTGTTTG . . . , 818G>A, 818G>T, 820G>A, 821T>C, 824G>A, 824G>C, 825T>G, 826G>C, 827C>A, 827C>T, 827_829CCT>TC, 829T>G, 830G>A, 830G>T, 832C>A, 832C>T, 832_833CC>TT, 833C>G, 833C>T, 834_835insN, 835G>A, 836G>A, 836_837GG>AA, 837G>A, 838A>T, 839G>A, 839G>C, 841G>A, 843C>A, 843C>G, 843C>T, 843_844CC>AT, 843_844CC>TT, 844C>G, 844C>T, 845G>A, 845G>T, 847C>T, 852A>T, 853G>A, 853G>C, 854A>T, 855G>A, 855_856GG>AA, 856G>A, 856G>C, 856G>T, 857A>T, 859G>A, 863delA, 865C>T, 867C>T, 868C>T, 868delC, 869G>A, 870C>G, 880G>A, 880G>T, 882G>A, 884C>T, 888_889CC>TT, 890delA, 892G>T, 898C>T, 899C>G, 898delC, 901C>T, 902_903insC, 904delG, 908G>C, 919G>T, 947C>T, 948_949CC>TT, 949C>T, 955A>G, 960G>A, 965C>T, 968T>C, 972T>A, 976G>T, 981T>A, 986_987CC>TT, 987C>A, 989T>G, 991C>T, 992_993insN, 1006G>T, 1009C>T, 1014C>T, 1023_1024CC>TT, 1024C>T, 1045G>T, 1050delC, 1051A>G, 1072G>A, 1082G>A, 1083delG, 1084delA, 1133C>T, 1143A>T, 559+11G>T, 559+37T>G, 74+12C>T, 783-57A>G, and 919+40delG.

In some instances, mutations in TP53 comprise deletions and mutations throughout the coding region. In some instances, a mutation in TP53 is in exon 1, 2, 3, 4, 5, 6, 7, 8, 9, 10, 11, or a combination thereof of TP53. In some instances, a mutation in TP53 is in exon 5, 7, 8, or a combination thereof of TP53. In some instances, a mutation in TP53 is in exon 5. In some instances, a mutation in TP53 is in exon 7. In some instances, a mutation in TP53 is in exon 8.

In some instances, a mutation in TP53 is a mutation in a peptide sequence. In some instances, the mutation results in a missense substitution, a nonsense substitution (*), a coding silent substitution, deletion (del), an insertion (ins), or a frameshift (fs). Exemplary mutations include, but are not limited to, D7H, E11K, P13S, W23*, P27S, V31I, P34L, P34P, S46P, S46F, P47fs*4, P47fs*76, D48N, E51*, W53*, W53*, W53C, F54F, E56*, P58fs*65, G59N, D61N, E68K, A69V, P71S, P71L, P72A, P72S, P72R, V73fs*76, V73M, P77S, P77del, P80S, P80L, T81I, T81fs*42, P82L, A83E, A84T, A84fs*65, A84V, A84V, P85S, P85L, A86fs*55, P87S, P89S, P89F, P89L, S90F, W91*, W91*, P92L, S94L, S95F, S96F, V97I, P98S, P98L, P98L, S99F, Q100*, T102I, Y103*, Q104*, Q104*, G105fs*18, G105fs*18, Y107*, Y107*, G108S, F109_R110delFR, F109S, R110C, R110C, R110fs*13, L111Q, T118fs*5, K120E, V122_T123>A, T125T, T125T, Y126*, S127F, S127F, S127F, P128S, A129V, L130F, L130fs*40, N131K, K132Q, K132E, K132M, K132N, M133K, F134L, C135R, C135Y, C135S, C135*, Q136*, Q136*, L137M, A138fs*32, A138V, A138V, K139*, K139fs*31, K139N, T140fs*9, T140I, P142S, P142F, P142L, V143E, V143G, Q144fs*26, Q144Q, L145R, W146*, W146*, V147A, D148_T155delDST PP . . . , S149F, S149S, T150I, P151S, P151H, P151L, P151P, P152fs*29, P152S, P152L, P152R, P152L, P152L, P152S, P153fs*26, G154fs*27, G154fs*27, T155fs*25, T155T, R156C, R156fs*14, R156P, V157fs*23, V157fs*17, V157I, V157F, R158C, R158C, R158R, A159T, A159V, A159V, A159A, M160I, M160I, A161T, A161V, A161A, Y163H, Y163D, Q165*, S166A, H168Y, H168fs*13, H168fs*3, M169I, T170A, T170M, E171Q, V172fs*2, V173M, V173L, V173G, V173L, R174K, R174S, R175 (e.g., R175H), C176Y, C176F, C176W, P177S, P177F, P177L, P177H, P177L, P177S, H178fs*69, H178Y, H178N, H178Y, H178fs*3, H178_H179>QY, H179Y, H179N, H179Y, H179L, H179Y, R181C, R181H, C182C, S183*, S183L, D184N, D186N, G187S, G187D, A189T, A189_V197delAPPQHL, A189V, A189A, P190S, P190F, P190L, P191S, P191L, P191P, Q192*, L194F, L194R, I195fs*12, I195F, R196*, R196*, R196L, R196*, V197E, E198K, E198*, N200fs*47, L201fs*8, L201V, L201_R202>FC, R202fs*9, R202P, R202L, R202P, V203fs*44, Y205D, Y205C, L206*, D207fs*6, D208Y, R209K, R209fs*6, T211I, R213*, R213Q, R213P, H214fs*5, S215R, V216G, V216G, V216M, V218M, V218E, V218G, V218G, P219L, P219L, P219L, Y220N, Y220C, E221fs*4, E221fs*4, P222L, P222L, P222P, P223fs*24, E224*, V225A, G226D, G226A, S227F, D228N, D228A, C229fs*10, T230A, T230I, T230T, T231S, H233fs*14, Y234N, Y234H, Y234S, Y234*, Y234S, N235D, N235S, N235I, Y236N, Y236H, C238S, C238Y, C238F, C238W, S240, S241P, S241F, S241F, S241S, C242S, C242G, C242Y, C242C, M243L, M243R, G244S, G245 (e.g., G245S, G245C, G245N, G245D, G245V, G245D, G245R), M246T, M246R, M246I, N247Y, N247T, R248 (e.g., R248W, R248W, R248C, R248Q, R248P, R248L, R248Q, R248R, R248Q, R248W, R248Y), R249 (e.g., R249W, R249_T256delRPILTI . . . , R249T, R249M, R249S, R249S), P250A, P250S, P250F, P250L, P250L, P250P, I251N, L252P, L252L, T253A, T253I, T253T, I255fs*90, L257P, E258K, E258K, D259fs*86, D259V, D259Y, S261C, L264fs*81, L265P, L265L, G266R, G266R, G266*, G266K, G266E, R267W, R267R, S269N, F270I, E271K, E271fs*73, V272M, V272E, V272G, R273 (e.g., R273G, R273C, R273_C275delRVC, R273H, R273L, R273C, R273H), V274I, V274A, C275Y, C275S, C275W, A276P, A276D, A276V, A276fs*69, C277G, C277Y, C277F, P278T, P278S, P278F, P278R, P278L, P278F, P278S, G279fs*27, G279R, G279E, G279E, G279G, G279W, R280*, R280K, R280T, D281N, D281E, D281E, D281D, D281_R282>EW, R282 (e.g., R282W, R282G, R282W, R282Q, R282L), R283C, T284 (e.g., T284T), E285K, E285Q, E285V, E285E, E286K, E286K, E286Q, E286*, E286V, E287K, N288fs*57, L289F, L289L, R290C, R290fs*55, R290H, R290R, E294K, E294*, E294E, P295L, H297Y, H297fs*48, E298*, P300S, P300R, P301fs*44, P301S, G302fs*4, S303fs*42, S303T, A307S, P316L, Q317*, Q317*, Q317*, K319E, K320K, P322L, L323P, D324E, E326*, Y327*, T329I, T329T, L330R, Q331*, Q331fs*6, E336*, R337C, F338F, R342*, R342*, E349*, K351fs*19, K351E, E358K, G361E, S362fs*8, S362fs*8, T377P, S378F, and K381N. In some instances, a mutation is R175, S240, G245, R248, R249, R273, R282, T284, or combinations thereof. In some cases, the mutation(s) are at the corresponding residue positions as set forth in SEQ ID NO: 1.

PTCH1, also known as Patched 1 or Protein Patched Homolog 1, is a gene that encodes PTCH1, a member of the patched family of proteins. PTCH1 is involved in hedgehog signaling pathway. In some instances, mutations in PTCH1 are involved in a non-melanoma skin cancer (e.g., BCC and/or SCC). In some instances, a mutation is a nucleotide sequence of PTCH1. For example, the mutation in the nucleotide sequence includes, but not limited to, 394+1delG, 584_584+1GG>AA, 747-1G>A, 1067+1G>A, 1068-2A>T, 1068-2_1068-1AG>CT, 1216-4_1227del16, 1216-6C>T, 1347+1G>A, 1504-8T>C, 1603-1G>A, 1729-1G>T, 1847+3A>T, 1848-1G>A, 2251-1G>A, 2561-1G>A, 3168+5G>T, 3306+1G>A, 3449+1G>A, 3549+5G>A, 204G>A, 250C>A, 250C>T, 262_274del13, 271G>A, 272G>A, 277_278insA, 286A>T, 290_291insT, 292_310del19, 304T>A, 343_344GG>AA, 378delG, 387G>A, 394G>A, 404G>A, 426T>A, 430_431ins11, 441_442TG>AT, 445G>T, 451G>A, 463C>T, 475A>T, 478C>T, 493G>T, 523C>T, 528_529AC>CT, 549_550CC>TT, 550C>T, 584G>A, 584G>T, 631A>G, 652C>T, 654G>A, 666T>A, 681G>A, 707G>A, 708G>A, 708_709GG>AA, 709G>A, 712_713insA, 713G>A, 717G>C, 724C>T, 751_760del10, 754C>T, 757C>A, 757C>T, 758_776del19, 767G>A, 768G>A, 804_807delAAAG, 809_818del10, 813_819delAAACTAT, 833G>A, 834G>A, 838G>A, 851_872del22, 857_861AGGTT>G, 862G>A, 863G>A, 865delC, 864_871delTCATGGTT, 879_880CC>TT, 992C>T, 994A>T, 1031G>A, 1047delC, 1055G>A, 1062_1063insC, 1062_1063insT, 1082A>C, 1085C>T, 1092_1093CC>TT, 1093C>T, 1106_1107CC>TT, 1108_1111delAAGC, 1138G>T, 1160G>A, 1161G>A, 1167_1168GG>AT, 1196G>A, 1229G>A, 1249C>T, 1249_1250ins28, 1285delG, 1292T>A, 1316T>C, 1324delG, 1356T>G, 1361_1389del29, 1393_1394insC, 1396C>T, 1433C>T, 1434_1437delACTG, 1439C>G, 1450G>A, 1481C>T, 1481_1485delCCTTT, 1510C>T, 1511C>A, 1511C>T, 1557C>T, 1585A>T, 1594C>T, 1595C>T, 1615G>T, 1634G>A, 1667delT, 1673_1695del23, 1688C>T, 1703C>T, 1703_1704CC>TT, 1703_1711delCCGCT . . . , 1717T>A, 1719delC, 1721_1722CC>TT, 1722C>T, 1725C>T, 1726C>T, 1777_1778CC>TT, 1778C>T, 1796_1799delATTT, 1800A>T, 1804C>T, 1847G>A, 1847G>C, 1854C>A, 1863_1864delAG, 1887delC, 1893_1894insC, 1922C>T, 1930C>T, 1959_1969del11, 1977G>A, 1980C>T, 1986_1987CC>TT, 1992C>T, 1993C>G, 1993C>T, 2004C>T, 2008C>T, 2011C>T, 2020delG, 2033C>T, 2038G>T, 2042G>T, 2048C>T, 2050G>T, 2062C>T, 2066C>T, 2072C>T, 2105C>T, 2107C>T, 2120C>T, 2126G>A, 2128G>A, 2128delG, 2134_2144del11, 2146delT, 2147_2148CC>TT, 2178_2179insC, 2207C>T, 2209G>A, 2209G>T, 2265C>T, 2287G>A, 2287delG, 2307_2308CC>TT, 2308C>T, 2321G>A, 2334G>A, 2345C>T, 2364T>A, 2372T>C, 2380C>T, 2385_2399del15, 2397_2418del22, 2400C>T, 2421C>T, 2421_2422CC>TT, 2438C>A, 2439delG, 2446C>T, 2477delT, 2485G>A, 2492_2493insAGTA, 2557C>T, 2566_2568CAG>T, 2588G>A, 2589G>A, 2666A>G, 2693A>G, 2708_2709insAT, 2709_2710insAA, 2713C>T, 2716_2729del14, 2747_2748CC>AT, 2758_2771del14, 2765_2766ins14, 2777G>A, 2777_2778GG>AA, 2778G>A, 2778_2779GG>AA, 2791_2793CCC>T, 2793_2794ins22, 2794_2795insC, 2810C>T, 2812C>T, 2843G>A, 2847C>T, 2865C>A, 2866_2867delAT, 2873delA, 2885G>C, 2891_2892ins17, 2910delG, 2965G>T, 2974G>T, 2985G>T, 3027C>T, 3046C>T, 3054G>A, 3054_3055GG>AA, 3072C>T, 3120C>T, 3138C>T, 3148C>T, 3152_3153GG>AA, 3153G>A, 3196G>T, 3209T>G, 3236G>T, 3240C>T, 3249delG, 3261C>T, 3320_3321CC>TT, 3340A>T, 3356T>A, 3374_3375CC>TT, 3378_3379CC>TT, 3389C>T, 3401T>A, 3422C>T, 3425G>A, 3435C>T, 3487G>A, 3499G>A, 3499G>T, 3509_3538>GGA, 3514C>T, 3583A>T, 3584C>T, 3586C>T, 3590C>T, 3591C>T, 3592C>T, 3603C>T, 3605C>T, 3634G>A, 3641C>T, 3662C>T, 3708_3709GG>AA, 3715C>T, 3724G>A, 3739G>A, 3748C>T, 3815_3816CC>TT, 3833C>T, 3844C>T, 3856_3867del12, 3857C>T, 3859C>T, 3883C>T, 3906C>T, 3917C>T, 3918C>T, 3944T>C, 3970G>A, 4058C>T, 4140C>T, 4179C>T, 4187G>A, 4204C>T, 4205C>T, 4235C>T, 4249C>T, 4324C>T, 4328G>T, 1405_1406ins, 1728_1728+1delGG, 3169-1_3169GG>AA, 1503+3A>T, 1729-2A>T, 2250+25T>C, 3169-2A>G, 3450-1G>A, 3450-2A>T, 3550-27C>T, 394+1G>A, 584+5G>A, 654+1G>A, 654+2T>A, and 945+5G>C.

In some instances, mutations in PTCH1 comprise deletions and mutations throughout the coding region. In some instances, a mutation in PTCH1 is in exon 1, 2, 3, 4, 5, 6, 7, 8, 9, 10, 11, 12, 13, 14, 15, 16, 17, 18, 19, 20, 21, 22, 23, 24, or a combination thereof of PTCH1. In some instances, a mutation in PTCH1 is in exon 2, 3, 5, 6, 8, 10, 12, 14, 15, 17, 18, 22, 23, or a combination thereof of PTCH1. In some instances, a mutation in PTCH1 is in exon 14, 15, 17, or a combination thereof of PTCH1. In some instances, a mutation in PTCH1 is in exon 2, 3, 5, 6, 8, 10, 12, 18, 22, 23, or a combination thereof of PTCH1. In some instances, a mutation in PTCH1 is in exon 14, 15, 17, or a combination thereof and further in combination with one or more from exon 2, 3, 5, 6, 8, 10, 12, 18, 22, or 23. In some instances, a mutation in PTCH1 is in exon 2 of PTCH1. In some instances, a mutation in PTCH1 is in exon 3 of PTCH1. In some instances, a mutation in PTCH1 is in exon 5 of PTCH1. In some instances, a mutation in PTCH1 is in exon 6 of PTCH1. In some instances, a mutation in PTCH1 is in exon 8 of PTCH1. In some instances, a mutation in PTCH1 is in exon 10 of PTCH1. In some instances, a mutation in PTCH1 is in exon 12 of PTCH1. In some instances, a mutation in PTCH1 is in exon 14 of PTCH1. In some instances, a mutation in PTCH1 is in exon 15 of PTCH1. In some instances, a mutation in PTCH1 is in exon 17 of PTCH1. In some instances, a mutation in PTCH1 is in exon 18 of PTCH1. In some instances, a mutation in PTCH1 is in exon 22 of PTCH1. In some instances, a mutation in PTCH1 is in exon 23 of PTCH1.

In some instances, a mutation in PTCH1 is a mutation in a peptide sequence. In some instances, the mutation results in a missense substitution, a nonsense substitution (*), a coding silent substitution, deletion (del), an insertion (ins), or a frameshift (fs). Exemplary mutations include, but are not limited to, G68G, Q84K, Q84*, F88fs*25, G91S, G91D, Y93fs*1, K96*, C98fs*42, C98fs*13, L102M, G115K, E127fs*10, W129*, V132I, R135Q, Y142*, R144fs*19, G148*, E149*, A151T, P155S, I159L, Q160*, E165*, L175F, Q177*, Q184*, Q184*, R195K, R195M, T211A, Q218*, Q218Q, Y222*, L227L, W236*, W236*, W236_E237>*, E237K, G238fs*14, G238E, A239A, Q242*, K251fs*15, P252S, P253T, P253S, L254fs*9, W256*, W256*, K270fs*1, K270fs*10, N272fs*9, W278*, W278*, E280K, K284fs*33, E286fs*37, G288S, G288D, H289fs*35, Y291fs*25, R294C, S331F, R332*, G344D, N349fs*18, G352E, V355fs*82, V355fs*82, Q361P, T362I, Q365*, Q365*, P369L, K370fs*61, E380*, H384fs*, W387*, W387*, D390Y, W399*, S410N, Q417*, Q417fs*29, D429fs*3, L431Q, V439A, V442fs*14, Y452*, C454fs*1, Q466fs*31, Q466*, V469M, A478V, L479fs*11, S480*, A483G, G484R, S494F, S494fs*1, P504S, P504Q, P504L, A519A, K529*, P532S, P532L, E539*, G545E, V556fs*9, F559fs*60, A563V, P568L, P568L, P568_L570delPAL, F573I, S574fs*6, S574F, S574S, L575L, Q576*, P593F, P593L, P593L, L600fs*22, L600F, R602*, S616N, S616T, C618*, R621fs*5, Q628*, Y630fs*63, D632fs*22, P641L, P644S, E653fs*24, Q659Q, S660S, Q663*, L664L, R665G, R665C, E667*, Y668Y, P670S, H671Y, V674fs*19, T678I, E680*, P681L, S683F, E684*, Q688*, P689L, T691I, P702L, E703*, S707F, R709K, D710N, D710fs*36, S713fs*21, S716fs*30, S716F, C727fs*11, A736V, E737K, E737*, A741V, F755F, V763I, V763fs*9, R770*, R770*, G774E, T778T, P782L, Y788*, I791T, Q794*, K796_F800del, F800fs*23, F800F, T807T, Q808*, P813Q, N814fs*16, Q816*, F826fs*4, V829M, Y831*, Q853*, Q853*, Q856fs*1, W863*, W863*, Q889R, D898G, K904fs*21, Q905fs*20, Q905*, L907fs*4, P916H, Y920fs*34, Y922fs*1, W926*, W926*, W926*, W926_V927>*, W926*, P931fs*27, V932fs*34, V932fs*27, S937F, Q938*, W948*, V949V, Y955*, M956fs*2, T959fs*3, R962T, A965fs*36, E970fs*25, L981F, E989*, E992*, R995S, Y1009Y, Y1013*, L1016F, W1018*, W1018_E1019>*, L1024L, F1040F, F1046F, P1050S, W1051*, W1051*, E1066*, M1070R, S1079I, A1080A, V1084fs*3, I1087I, A1107V, R1114W, L1119Q, P1125L, (=), A1130V, L1134Q, A1141V, G1142E, F1145F, G1163S, G1167R, G1167W, L1170_P1180>WT, P1172S, T1195S, T1195I, P1196S, S1197F, S1197S, P1198S, P1201P, P1202L, G1212S, T1214M, S1221F, E1237K, R1239W, E1242K, E1242K, A1247T, P1250S, P1272L, P1278L, P1282S, P1286_D1289del, P1286L, H1287Y, P1295S, P1302P, P1306L, P1306P, L1315P, P1315L, E1324K, A1353V, A1380A, P1387S, P1393P, G1396E, P1402S, P1402L, P1412L, H1417Y, R1442W, and G1443V.

In some instances, a mutation is S616N, S616T, C618*, R621fs*5, Y630fs*63, D632fs*22, P641L, P644S, E653fs*24, Q659Q, Q663*, L664L, R665G, Y668Y, P670S, H671Y, T678I, E680*, P681L, S683F, E684*, Q688*, P689L, T691I, P702L, S707F, S716fs*30, C727fs*11, A736V, or combinations thereof. In some cases, the mutation(s) are at the corresponding residue positions as set forth in SEQ ID NO: 3 or 4.

Expression level or mutational change once detected, in certain embodiments, provides information regarding a disease in an individual. In some instances, expression level of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, SPP1, or combinations thereof provides information regarding the disease in the individual. In some instances, mutational change of TERT, CDKN2A, TP53, PTCH1, or combinations thereof provides information regarding the disease of the individual. In some instances, both expression level and mutational change provide information regarding the disease in the individual. Information regarding the disease includes, but is not limited to, identification of a disease state, likelihood of treatment success for a given disease state, identification of progression of a disease state, and identification of a disease stage. In some instances, at least one of expression level and mutational change are compared to a control sample for identification of the disease state, determining likelihood of treatment success for the given disease state, identification of progression of the disease state, or identification of the disease stage. In some instances, the control sample is any sample that is used for making any one of these determinations. In some instances, the control sample is from a healthy individual. In some instances, the control is a sample from an individual with a known disease or disorder. In some instances, the control is from a database or reference. In some instances, the control is a normal sample from the same individual. In some instances, the normal sample is a sample that does not comprise cancer, disease, or disorder, or a sample that would test negative for cancer, disease, or disorder. In some instances, the normal sample is assayed at the same time or at a different time.

In some instances, an expression level of one or more genes of interest from a biological sample varies as compared to a control sample. In some instances, the control sample is a non-cancer sample. In some instances, the expression level is of at least two genes selected from a group consisting of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1. In some instances, the expression level is at least or about 5%, 6%, 7%, 8%, 9%, 10%, 11%, 12%, 13%, 14%, 15%, 16%, 17%, 18%, 19%, 20%, 22%, 24%, 28%, 30%, 35%, 40%, 45%, 50%, 55%, 60%, 65%, 70%, 75%, 80%, 85%, 90%, 95% or more than 95% increased as compared to control. In some instances, the expression level is increased in a range of about 1% to about 100%, about 10% to about 90%, about 20% to about 80%, about 30% to about 70%, or about 40% to about 60%.

In some instances, a mutational change in one or more genes of interest from a biological sample comprises at least one mutation as compared to a control sample. In some instances, the mutational change is in TERT, CDKN2A, TP53, PTCH1, or a combination thereof. In some instances, TERT, CDKN2A, TP53, PTCH1, or a combination thereof from the biological sample comprises at least or about 1, 2, 3, 4, 5, 6, 7, 8, 9, 10, or more than 10 mutations. In some instances, TERT, CDKN2A, TP53, PTCH1, or a combination thereof from the biological sample comprises at least or about at least 1.5×, 2×, 3×, 4×, 5×, 6×, 7×, 8×, 9×, OX, IX, or 12× more mutations compared to a normal biological sample.

In some instances, at least one of expression level and mutational change of a gene of interest provide information regarding a skin cancer. In some instances, the skin cancer is melanoma, basal cell carcinoma (BCC), or squamous cell carcinoma (SCC). In some instances, the skin cancer is BCC. In some instances, the skin cancer is SCC. For example, the at least one of expression level and mutational change of a gene of interest provide information regarding a stage of skin cancer. In some instances, the at least one of expression level and mutational change of a gene of interest is associated with a stage of skin cancer. In some instances, one or more mutations in a gene of interest indicate a risk factor for skin cancer or the stage of skin cancer. In some instances, the gene of interest is MMP1, S100A7, CMPK2, IRF7, IGFL1, CXCL1, UPP1, DEFB4A, FOS, OAS3, SCD5, RTP4, VEGFA, COL5A2, 1L24, AADACL2, PTCH1, CD68, PRKACA, and SPP. In some instances, the gene of interest is at least one of TERT, CDKN2A, TP53, and PTCH1.

Methods and compositions provided herein comprising detecting at least one of expression level and mutational change result in improved sensitivity and specificity for diagnosis or prognosis of disease. In some instances, detecting at least one of expression level and mutational change result in improved sensitivity and specificity for diagnosis or prognosis of skin cancer. In some instances, sensitivity is improved by at least or about 55%, 60%, 65%, 70%, 75%, 80%, 85%, 90%, 95% or more than 95% as compared to other diagnosis or prognosis methods. In some instances, specificity is improved by at least or about 55%, 60%, 65%, 70%, 75%, 80%, 85%, 90%, 95% or more than 95% as compared to other diagnosis or prognosis methods. The other diagnosis or prognosis methods include, but are not limited to, morphology histopathology, pattern histopathology, and RNA only based gene expression assays.

Computer Implemented Methods and Systems for Carcinoma Assay

Described herein, in some embodiments, are computer-implemented methods for differentiating one or more cancer samples from one or more non-cancer samples, comprising: (a) hybridizing a set of probes that recognizes MMP1, S100A7, CMPK2, IRF7, IGFL1, CXCL1, UPP1, DEFB4A, FOS, OAS3, SCD5, RTP4, VEGFA, COL5A2, 1L24, AADACL2, PTCH1, CD68, PRKACA, or SPP1 to generate gene expression data; (b) obtaining, by a processor, the gene expression data; and (c) analyzing, by the processor, the gene expression data to differentiate the one or more cancer samples from the one or more non-cancer samples, wherein the analysis comprises: (i) generating a plurality of pair-wise interactions between at least two genes of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 in a set of samples; (ii) analyzing the plurality of pair-wise interactions using a machine learning method to determine an area under a curve (AUC) value for each of the plurality of pair-wise interactions; and (iii) differentiating the one or more cancer samples from the one or more non-cancer samples when an AUC value is greater than above about 0.8. In some instances, the pair-wise interactions are set out in Table 1. In some instances, the pair-wise interactions are set out in Table 2. In some instances, the pair-wise interactions are set out in Table 3. In some instances, the pair-wise interactions comprises MMP1, S100A7; CMPK2, IRF7; IGFL1, CXCL1; and IGFL1, CMPK2. In some instances, the pair-wise interactions comprises MMP1, S100A7; CMPK2, IRF7; IGFL1, CXCL1; IGFL1, CMPK2; and UPP1, CMPK2. In some instances, the pair-wise interactions comprises SCD5, S100A7 and CMPK2, IRF7. In some instances, the pair-wise interactions comprises IGFL1, COL5A2; IL24, AADACL2; PTCH1, CD68; PRKACA, SPP1; AADACL2, MMP1; or a combination thereof. In some instances, the pair-wise interactions comprises IGFL1, COL5A2 or AADACL2, MMP1. In some instances, the pair-wise interactions comprises IL24, AADACL2; PTCH1, CD68; or PRKACA, SPP1. In some instances, the pair-wise interactions comprises IGFL1, COL5A2; IL24, AADACL2; PTCH1, CD68; PRKACA, SPP1; or AADACL2, MMP1. In some instances, the pair-wise interactions comprises IGFL1, COL5A2; IL24, AADACL2; PTCH1, CD68; PRKACA, SPP1; and AADACL2, MMP. In some instances, the machine learning method utilizes an algorithm selected from: random forest (rf) model, boosting model, logit model, or lasso model. In some instances, the set of samples comprises basal cell carcinoma, squamous cell carcinoma, actinic keratosis (AK), seborrheic keratosis (SK), normal samples, or a combination thereof. In some instances, the set of samples comprises basal cell carcinoma, squamous cell carcinoma, actinic keratosis (AK), seborrheic keratosis (SK), and normal samples. In some instances, the set of samples comprises basal cell carcinoma, squamous cell carcinoma, and actinic keratosis (AK). In some instances, the set of samples comprises basal cell carcinoma and squamous cell carcinoma. In some instances, the one or more cancer samples are differentiated from the one or more non-cancer samples when an AUC value is greater than above about 0.6, 0.65, 0.7, 0.75, 0.8, 0.85, 0.9, or 0.95.

Described herein, in some embodiments, are computer-implemented systems comprising a digital processing device comprising: (a) a first computing device comprising a processor, a memory module, an operating system, and a computer program including instructions executable by the processor to create a data acquisition application for receiving gene expression from a sample, the data acquisition application comprising: a data receiving module for receiving gene expression data of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, SPP1, or a combination thereof, and (b) a second computing device comprising a processor, a memory module, an operating system, and a computer program including instructions executable by the processor to create a data analysis application for differentiating a cancer sample from a non-cancer sample, the data analysis application comprising a data analysis module to: (i) generate a plurality of pair-wise interactions between at least two genes of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 from the gene expression data; and (ii) analyze the plurality of pair-wise interactions with a control using a machine learning method to differentiate a cancer sample from a non-cancer sample, wherein the machine learning method comprises: (1) identifying a plurality of weights associated with the plurality of pair-wise interactions based on a top score; (2) determining an area under a curve (AUC) value for each of the plurality of pair-wise interactions; and (3) classifying the sample as a cancer or non-cancer sample based on the plurality of pair-wise interactions and the plurality of weights when the AUC value is greater than about 0.8. In some instances, the pair-wise interactions are set out in Table 1. In some instances, the pair-wise interactions are set out in Table 2. In some instances, the pair-wise interactions are set out in Table 3. In some instances, the pair-wise interactions comprises MMP1, S100A7; CMPK2, IRF7; IGFL1, CXCL1; and IGFL1, CMPK2. In some instances, the pair-wise interactions comprises MMP1, S100A7; CMPK2, IRF7; IGFL1, CXCL1; IGFL1, CMPK2; and UPP1, CMPK2. In some instances, the pair-wise interactions comprises SCD5, S100A7 and CMPK2, IRF7. In some instances, the pair-wise interactions comprises IGFL1, COL5A2; IL24, AADACL2; PTCH1, CD68; PRKACA, SPP1; AADACL2, MMP1; or a combination thereof. In some instances, the pair-wise interactions comprises IGFL1, COL5A2 or AADACL2, MMP1. In some instances, the pair-wise interactions comprises IL24, AADACL2; PTCH1, CD68; or PRKACA, SPP1. In some instances, the pair-wise interactions comprises IGFL1, COL5A2; IL24, AADACL2; PTCH1, CD68; PRKACA, SPP1; or AADACL2, MMP1. In some instances, the pair-wise interactions comprises IGFL1, COL5A2; IL24, AADACL2; PTCH1, CD68; PRKACA, SPP1; and AADACL2, MMP. In some instances, the machine learning method utilizes an algorithm selected from: random forest (rf) model, boosting model, logit model, or lasso model. In some instances, the machine learning method utilizes rf model, boosting model, or lasso model. In some instances, the control dataset comprises a first set of pair-wise interactions between at least two genes of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 from gene expression data obtained from at least one cancer sample; and a second set of pair-wise interactions between at least two genes of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 obtained from at least one non-cancer sample. In some instances, the at least one cancer sample comprises basal cell carcinoma, squamous cell carcinoma, or a combination thereof. In some instances, the at least one non-cancer sample comprises actinic keratosis (AK), seborrheic keratosis (SK), a normal sample, or a combination thereof. In some instances, the gene expression data comprises one or more cycle threshold (Ct) values. In some instances, the data receiving module further receives gene expression data from a set of samples. In some instances, the set of samples comprises: basal cell carcinoma, squamous cell carcinoma, actinic keratosis (AK), seborrheic keratosis (SK), a normal sample, or a combination thereof, or basal cell carcinoma, squamous cell carcinoma, and actinic keratosis (AK). In some instances, the one or more cancer samples are differentiated from the one or more non-cancer samples when an AUC value is greater than above about 0.6, 0.65, 0.7, 0.75, 0.8, 0.85, 0.9, or 0.95.

Described herein, in some embodiments, are non-transitory computer-readable medium with instructions stored thereon, that when executed by a processor, perform the steps comprising: (a) generating gene expression data of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1 from a set of biological samples by a hybridizing method; (b) obtaining, by a processor, the gene expression data; (c) generating a plurality of pair-wise interactions between at least two genes of MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, and SPP1; (d) analyzing the plurality of pair-wise interactions using a machine learning method to determine an area under a curve (AUC) value for each of the plurality of pair-wise interactions; and (e) differentiating the one or more cancer samples from the one or more non-cancer samples when an AUC value is greater than above about 0.8. In some instances, the pair-wise interactions are set out in Table 1. In some instances, the pair-wise interactions are set out in Table 2. In some instances, the pair-wise interactions are set out in Table 3. In some instances, the pair-wise interactions comprises MMP1, S100A7; CMPK2, IRF7; IGFL1, CXCL1; and IGFL1, CMPK2. In some instances, the pair-wise interactions comprises MMP1, S100A7; CMPK2, IRF7; IGFL1, CXCL1; IGFL1, CMPK2; and UPP1, CMPK2. In some instances, the pair-wise interactions comprises SCD5, S100A7 and CMPK2, IRF7. In some instances, the pair-wise interactions comprises IGFL1, COL5A2; IL24, AADACL2; PTCH1, CD68; PRKACA, SPP1; AADACL2, MMP1; or a combination thereof. In some instances, the pair-wise interactions comprises IGFL1, COL5A2 or AADACL2, MMP1. In some instances, the pair-wise interactions comprises IL24, AADACL2; PTCH1, CD68; or PRKACA, SPP1. In some instances, the pair-wise interactions comprises IGFL1, COL5A2; IL24, AADACL2; PTCH1, CD68; PRKACA, SPP1; or AADACL2, MMP1. In some instances, the pair-wise interactions comprises IGFL1, COL5A2; IL24, AADACL2; PTCH1, CD68; PRKACA, SPP1; and AADACL2, MMP. In some instances, the machine learning method utilizes an algorithm selected from: random forest (rf) model, boosting model, logit model, or lasso model. In some instances, the set of samples comprises basal cell carcinoma, squamous cell carcinoma, actinic keratosis (AK), seborrheic keratosis (SK), normal samples, or a combination thereof. In some instances, the set of samples comprises basal cell carcinoma, squamous cell carcinoma, actinic keratosis (AK), seborrheic keratosis (SK), and normal samples. In some instances, the set of samples comprises basal cell carcinoma, squamous cell carcinoma, and actinic keratosis (AK). In some instances, the one or more cancer samples are differentiated from the one or more non-cancer samples when an AUC value is greater than above about 0.6, 0.65, 0.7, 0.75, 0.8, 0.85, 0.9, or 0.95.

Biological Samples and Methods of Use

Biological samples are obtained using a variety of methods. In some instances, obtaining a biological sample such as a skin sample comprises, but is not limited to, scraping of the skin, biopsy, suction, blowing and other techniques. In some instances, obtaining the biological sample is non-invasive. For example, the biological sample is obtained from a skin using a skin sample collector. In some cases, the biological sample is obtained by applying an adhesive patch to a skin sample in a manner sufficient to adhere a sample of the skin to the adhesive patch, and removing the adhesive patch from the skin in a manner sufficient to retain the adhered skin sample to the adhesive patch. In some instances, the patch comprises a rubber adhesive on a polyurethane film. In some instances, about one to about ten adhesive patches or one to ten applications of the patch are applied to and removed from the skin.

In some instances, an effective amount of skin sample is removed by the adhesive patch. In some instances, the effective amount comprises between about 50 microgram to about 500 microgram, between about 100 microgram to about 450 microgram, between about 100 microgram to about 350 microgram, between about 100 microgram to about 300 microgram, between about 120 microgram to about 250 microgram, or between about 150 microgram to about 200 microgram of nucleic acid material.

In some instances, the adhesive patch comprises various materials. In some embodiments, the adhesive patch comprises a matrix comprising a synthetic rubber compound. In some embodiments, the adhesive patch does not comprise a latex material, a silicone material, or a combination thereof.

In some embodiments, the adhesive patch comprises a first central collection area having a skin facing surface comprising the adhesive matrix and a second area extending from the periphery of the first collection area creating a tab. In some cases, the first central collection area and the second area are comprised of different materials. In some cases, the first central collection area is comprised of a polyurethane carrier film.

In some embodiments, the skin sample is obtained from a site on a body. In some instances, the skin sample is obtained from a chest, forehead, hand, mastoid, temple, abdomen, arm, or leg. In some cases, the skin sample is not obtained from an area located on the palms, soles of feet, or mucous membranes.

In some embodiments, the skin sample is obtained from a skin lesion. In some cases, the skin lesion is a pigmented skin lesion comprising a mole, dark colored skin spot, or melanin containing skin area. In some cases, the skin lesion is an area on the skin surface that is suspicious for melanoma, lupus, rubeola, acne, hemangioma, psoriasis, eczema, candidiasis, impetigo, shingles, leprosy, Crohn's disease, inflammatory dermatoses, bullous diseases, infections, basal cell carcinoma, actinic keratosis, merkel cell carcinoma, sebaceous carcinoma, squamous cell carcinoma, and dermatofibrosarcoma protuberans. In some instances, the skin lesion is suspicious for skin cancer. Exemplary skin cancer include, but are not limited to, melanoma, basal cell carcinoma (BCC), squamous cell carcinoma (SCC), angiosarcoma, cutaneous B-cell lymphoma, cutaneous T-cell lymphoma, dermatofibrosarcoma protuberans, Merkel cell carcinoma, and sebaceous gland carcinoma. In some instances, the skin lesion is suspicious for melanoma. In some instances, the skin lesion is suspicious for basal cell carcinoma. In some instances, the skin lesion is suspicious for squamous cell carcinoma.

In some cases, the skin lesion is from about 5 mm to about 20 mm in diameter.

Methods and compositions as described herein, in certain embodiments, result in obtaining various layers of skin. In some instances, the layers of skin include epidermis or dermis. The epidermis is further subdivided into stratum corneum, stratum lucidum, stratum granulosum, stratum spinosum, and stratum germinativum. In some instances, the skin sample is obtained from the epidermis layer, optionally from one or more of stratum corneum, stratum lucidum, stratum granulosum, stratum spinosum, and stratum germinativum. In some instances, the skin sample is obtained from the dermis layer. In some instances, cells are obtained from the skin using methods and compositions as described herein. Exemplary cells that are obtained include, but are not limited to, keratinocytes, melanocytes, basal cells, T-cells, Merkel cells, Langerhans cells, fibroblasts, macrophages, adipocytes, and dendritic cells.

Provided herein are methods and compositions for extraction of nucleic acids from a biological sample such as a sample collected using an adhesive patch. In some instances, nucleic acids are extracted using any technique that does not interfere with subsequent analysis. In some instances, this technique uses alcohol precipitation using ethanol, methanol or isopropyl alcohol. In some instances, this technique uses phenol, chloroform, or any combination thereof. In some instances, this technique uses cesium chloride. In some instances, this technique uses sodium, potassium or ammonium acetate or any other salt commonly used to precipitate the nucleic acids.

In some instances, the nucleic acid is a RNA molecule or a fragmented RNA molecule (RNA fragments). In some instances, the RNA is a microRNA (miRNA), a pre-miRNA, a pri-miRNA, a mRNA, a pre-mRNA, a viral RNA, a viroid RNA, a virusoid RNA, circular RNA (circRNA), a ribosomal RNA (rRNA), a transfer RNA (tRNA), a pre-tRNA, a long non-coding RNA (lncRNA), a small nuclear RNA (snRNA), a circulating RNA, a cell-free RNA, an exosomal RNA, a vector-expressed RNA, a RNA transcript, a synthetic RNA, or combinations thereof. In some instances, the RNA is mRNA. In some instances, the RNA is cell-free circulating RNA.

In some instances, the nucleic acid is DNA. DNA includes, but not limited to, genomic DNA, viral DNA, mitochondrial DNA, plasmid DNA, amplified DNA, circular DNA, circulating DNA, cell-free DNA, or exosomal DNA. In some instances, the DNA is single-stranded DNA (ssDNA), double-stranded DNA, denaturing double-stranded DNA, synthetic DNA, and combinations thereof. In some instances, the DNA is genomic DNA. In some instances, the DNA is cell-free circulating DNA.

Following extraction of nucleic acids from a biological sample, the nucleic acids, in some instances, are further purified. In some instances, the nucleic acids are RNA. In some instances, the nucleic acids are DNA. In some instances, nucleic acids are purified using a column or resin based nucleic acid purification scheme. In some instances, this technique utilizes a support comprising a surface area for binding the nucleic acids. In some instances, the support is made of glass, silica, latex or a polymeric material. In some instances, the support comprises spherical beads.

Methods and compositions for isolating nucleic acids, in certain embodiments, comprise using spherical beads. In some instances, the beads comprise material for isolation of nucleic acids. Exemplary material for isolation of nucleic acids using beads include, but not limited to, glass, silica, latex, and a polymeric material. In some instances, the beads are magnetic. In some instances, the beads are silica coated. In some instances, the beads are silica-coated magnetic beads. In some instances, a diameter of the spherical bead is at least or about 0.5 um, 1 um, 1.5 um, 2 um, 2.5 um, 3 um, 3.5 um, 4 um, 4.5 um, 5 um, 5.5 um, 6 um, 6.5 um, 7 um, 7.5 um, 8 um, 8.5 um, 9 um, 9.5 um, 10 um, or more than 10 um.

In some cases, a yield of the nucleic acids products obtained using methods described herein is about 500 picogram or higher, about 1000 picogram or higher, about 2000 picogram or higher, about 3000 picogram or higher, about 4000 picogram or higher, about 5000 picogram or higher, about 6000 picogram or higher, about 7000 picogram or higher, about 8000 picogram or higher, about 9000 picogram or higher, about 10000 picogram or higher, about 20000 picogram or higher, about 30000 picogram or higher, about 40000 picogram or higher, about 50000 picogram or higher, about 60000 picogram or higher, about 70000 picogram or higher, about 80000 picogram or higher, about 90000 picogram or higher, or about 100000 picogram or higher.

In some cases, methods described herein provide less than less than 10%, less than 8%, less than 5%, less than 2%, less than 1%, or less than 0.5% product yield variations between samples.

In some cases, methods described herein provide a substantially homogenous population of a nucleic acid product.

In some cases, methods described herein provide less than 30%, less than 25%, less than 20%, less than 15%, less than 10%, less than 8%, less than 5%, less than 2%, less than 1%, or less than 0.5% contaminants.

In some instances, following extraction, nucleic acids are stored. In some instances, the nucleic acids are stored in water, Tris buffer, or Tris-EDTA buffer before subsequent analysis. In some instances, this storage is less than 8° C. In some instances, this storage is less than 4° C. In certain embodiments, this storage is less than 0° C. In some instances, this storage is less than −20° C. In certain embodiments, this storage is less than −70° C. In some instances, the nucleic acids are stored for about 1, 2, 3, 4, 5, 6, or 7 days.

In some instances, the nucleic acids are stored for about 1, 2, 3, or 4 weeks. In some instances, the nucleic acids are stored for about 1, 2, 3, 4, 5, 6, 7, 8, 9, 10, 11, or 12 months.

In some instances, nucleic acids isolated using methods described herein are subjected to an amplification reaction following isolation and purification. Non-limiting amplification reactions include, but are not limited to, quantitative PCR (qPCR), self-sustained sequence replication, transcriptional amplification system, Q-Beta Replicase, rolling circle replication, or any other nucleic acid amplification known in the art. In some instances, the amplification reaction is PCR. In some instances, the amplification reaction is quantitative such as qPCR.

Provided herein are methods and compositions for detecting an expression level of one or more genes of interest from nucleic acids isolated from a biological sample. In some instances, the expression level is detected following an amplification reaction. In some instances, the nucleic acids are RNA. In some instances, the expression level is determined using PCR. In some instances, the expression level is determined using qPCR. In some instances, primers and probes for use in the qPCR are specific to MMP1, S100A7, CMPK2, IRF7, IGFL1, CXCL1, UPP1, DEFB4A, FOS, OAS3, SCD5, RTP4, VEGFA, COL5A2, IL24, AADACL2, PTCH1, CD68, PRKACA, SPP1, or a combination thereof. In some instances, the expression level is determined using a microarray. In some instances, the expression level is determined by sequencing.

Provided herein are methods and compositions for detecting a mutational change of one or more genes of interest from nucleic acids isolated from a biological sample. In some instances, the mutational change is detected following an amplification reaction. In some instances, the nucleic acids are RNA. In some instances, the nucleic acids are DNA. In some instances, the mutational change is detected using allele specific PCR. In some instances, the mutational change is detected using sequencing. In some instances, the sequencing is performed using the Sanger sequencing method. In some instances, the sequencing involves the use of chain terminating dideoxynucleotides. In some instances, the sequencing involves gel-electrophoresis. In some instances, the sequencing is performed using a next generation sequencing method. In some instances, sequencing includes, but not limited to, single-molecule real-time (SMRT) sequencing, Polony sequencing, sequencing by synthesis, sequencing by ligation, reversible terminator sequencing, proton detection sequencing, ion semiconductor sequencing, nanopore sequencing, electronic sequencing, pyrosequencing, Maxam-Gilbert sequencing, chain termination sequencing, +S sequencing, and sequencing by synthesis.

Components of the Skin Collection Kit

In some embodiments, the adhesive patch from the sample collection kit described herein comprises a first collection area comprising an adhesive matrix and a second area extending from the periphery of the first collection area. The adhesive matrix is located on a skin facing surface of the first collection area. The second area functions as a tab, suitable for applying and removing the adhesive patch. The tab is sufficient in size so that while applying the adhesive patch to a skin surface, the applicant does not come in contact with the matrix material of the first collection area. In some embodiments, the adhesive patch does not contain a second area tab. In some instances, the adhesive patch is handled with gloves to reduce contamination of the adhesive matrix prior to use.

In some embodiments, the first collection area is a polyurethane carrier film. In some embodiments, the adhesive matrix is comprised of a synthetic rubber compound. In some embodiments, the adhesive matrix is a styrene-isoprene-styrene (SIS) linear block copolymer compound. In some instances, the adhesive patch does not comprise latex, silicone, or both. In some instances, the adhesive patch is manufactured by applying an adhesive material as a liquid-solvent mixture to the first collection area and subsequently removing the solvent.

The matrix material is sufficiently sticky to adhere to a skin sample. The matrix material is not so sticky that is causes scarring or bleeding or is difficult to remove. In some embodiments, the matrix material is comprised of a transparent material. In some instances, the matrix material is biocompatible. In some instances, the matrix material does not leave residue on the surface of the skin after removal. In certain instances, the matrix material is not a skin irritant.

In some embodiments, the adhesive patch comprises a flexible material, enabling the patch to conform to the shape of the skin surface upon application. In some instances, at least the first collection area is flexible. In some instances, the tab is plastic. In an illustrative example, the adhesive patch does not contain latex, silicone, or both. In some embodiments, the adhesive patch is made of a transparent material, so that the skin sampling area of the subject is visible after application of the adhesive patch to the skin surface. The transparency ensures that the adhesive patch is applied on the desired area of skin comprising the skin area to be sampled. In some embodiments, the adhesive patch is between about 5 and about 100 mm in length. In some embodiments, the first collection area is between about 5 and about 40 mm in length. In some embodiments, the first collection area is between about 10 and about 20 mm in length. In some embodiments the length of the first collection area is configured to accommodate the area of the skin surface to be sampled, including, but not limited to, about 19 mm, about 20 mm, about 21 mm, about 22 mm, about 23 mm, about 24 mm, about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, and about 100 mm. In some embodiments, the first collection area is elliptical.

In further embodiments, the adhesive patch of this invention is provided on a peelable release sheet in the adhesive skin sample collection kit. In some embodiments, the adhesive patch provided on the peelable release sheet is configured to be stable at temperatures between −80° C. and 30° C. for at least 6 months, at least 1 year, at least 2 years, at least 3 years, and at least 4 years. In some instances, the peelable release sheet is a panel of a tri-fold skin sample collector.

In some instances, nucleic acids are stable on adhesive patch or patches when stored for a period of time or at a particular temperature. In some instances, the period of time is at least or about 1 day, 2 days, 3 days, 4 days, 5 days, 6 days, 7 days, 2 weeks, 3 weeks, 4 weeks, or more than 4 weeks. In some instances, the period of time is about 7 days. In some instances, the period of time is about 10 days. In some instances, the temperature is at least or about −80° C., −70° C., −60° C., −50° C., −40° C., −20° C., −10° C., −4° C., 0° C., 5° C., 15° C., 18° C., 20° C., 25° C., 30° C., 35° C., 40° C., 45° C., 50° C., or more than 50° C. The nucleic acids on the adhesive patch or patches, in some embodiments, are stored for any period of time described herein and any particular temperature described herein. For example, the nucleic acids on the adhesive patch or patches are stored for at least or about 7 days at about 25° C., 7 days at about 30° C., 7 days at about 40° C., 7 days at about 50° C., 7 days at about 60° C., or 7 days at about 70° C. In some instances, the nucleic acids on the adhesive patch or patches are stored for at least or about 10 days at about −80° C.

The peelable release sheet, in certain embodiments, is configured to hold a plurality of adhesive patches, including, but not limited to, 12, 11, 10, 9, 8, 7, 6, 5, 4, 3, 2, 1, from about 2 to about 8, from about 2 to about 7, from about 2 to about 6, from about 2 to about 4, from about 3 to about 6, from about 3 to about 8, from about 4 to about 10, from about 4 to about 8, from about 4 to about 6, from about 4 to about 5, from about 6 to about 10, from about 6 to about 8, or from about 4 to about 8. In some instances, the peelable release sheet is configured to hold about 12 adhesive patches. In some instances, the peelable release sheet is configured to hold about 11 adhesive patches. In some instances, the peelable release sheet is configured to hold about 10 adhesive patches. In some instances, the peelable release sheet is configured to hold about 9 adhesive patches. In some instances, the peelable release sheet is configured to hold about 8 adhesive patches. In some instances, the peelable release sheet is configured to hold about 7 adhesive patches. In some instances, the peelable release sheet is configured to hold about 6 adhesive patches. In some instances, the peelable release sheet is configured to hold about 5 adhesive patches. In some instances, the peelable release sheet is configured to hold about 4 adhesive patches. In some instances, the peelable release sheet is configured to hold about 3 adhesive patches. In some instances, the peelable release sheet is configured to hold about 2 adhesive patches. In some instances, the peelable release sheet is configured to hold about 1 adhesive patch.

Provided herein, in certain embodiments, are methods and compositions for obtaining a sample using an adhesive patch, wherein the adhesive patch is applied to the skin and removed from the skin. After removing the used adhesive patch from the skin surface, the patch stripping method, in some instances, further comprise storing the used patch on a placement area sheet, where the patch remains until the skin sample is isolated or otherwise utilized. In some instances, the used patch is configured to be stored on the placement area sheet for at least 1 week at temperatures between −80° C. and 30° C. In some embodiments, the used patch is configured to be stored on the placement area sheet for at least 2 weeks, at least 3 weeks, at least 1 month, at least 2 months, at least 3 months, at least 4 months, at least 5 months, and at least 6 months at temperatures between −80° C. to 30° C.

In some instances, the placement area sheet comprises a removable liner, provided that prior to storing the used patch on the placement area sheet, the removable liner is removed. In some instances, the placement area sheet is configured to hold a plurality of adhesive patches, including, but not limited to, 12, 11, 10, 9, 8, 7, 6, 5, 4, 3, 2, 1, from about 2 to about 8, from about 2 to about 7, from about 2 to about 6, from about 2 to about 4, from about 3 to about 6, from about 3 to about 8, from about 4 to about 10, from about 4 to about 8, from about 4 to about 6, from about 4 to about 5, from about 6 to about 10, from about 6 to about 8, or from about 4 to about 8. In some instances, the placement area sheet is configured to hold about 12 adhesive patches. In some instances, the placement area sheet is configured to hold about 11 adhesive patches. In some instances, the placement area sheet is configured to hold about 10 adhesive patches. In some instances, the placement area sheet is configured to hold about 9 adhesive patches. In some instances, the placement area sheet is configured to hold about 8 adhesive patches. In some instances, the placement area sheet is configured to hold about 7 adhesive patches. In some instances, the placement area sheet is configured to hold about 6 adhesive patches. In some instances, the placement area sheet is configured to hold about 5 adhesive patches. In some instances, the placement area sheet is configured to hold about 4 adhesive patches. In some instances, the placement area sheet is configured to hold about 3 adhesive patches. In some instances, the placement area sheet is configured to hold about 2 adhesive patches. In some instances, the placement area sheet is configured to hold about 1 adhesive patch.

The used patch, in some instances, is stored so that the matrix containing, skin facing surface of the used patch is in contact with the placement area sheet. In some instances, the placement area sheet is a panel of the tri-fold skin sample collector. In some instances, the tri-fold skin sample collector further comprises a clear panel. In some instances, the tri-fold skin sample collector is labeled with a unique barcode that is assigned to a subject. In some instances, the tri-fold skin sample collector comprises an area for labeling subject information.

In an illustrative embodiment, the adhesive skin sample collection kit comprises the tri-fold skin sample collector comprising adhesive patches stored on a peelable release panel. In some instances, the tri-fold skin sample collector further comprises a placement area panel with a removable liner. In some instances, the patch stripping method involves removing an adhesive patch from the tri-fold skin sample collector peelable release panel, applying the adhesive patch to a skin sample, removing the used adhesive patch containing a skin sample and placing the used patch on the placement area sheet. In some instances, the placement area panel is a single placement area panel sheet. In some instances, the identity of the skin sample collected is indexed to the tri-fold skin sample collector or placement area panel sheet by using a barcode or printing patient information on the collector or panel sheet. In some instances, the indexed tri-fold skin sample collector or placement sheet is sent to a diagnostic lab for processing. In some instances, the used patch is configured to be stored on the placement panel for at least 1 week at temperatures between −80° C. and 25° C. In some embodiments, the used patch is configured to be stored on the placement area panel for at least 2 weeks, at least 3 weeks, at least 1 month, at least 2 months, at least 3 months, at least 4 months, at least 5 months, and at least 6 months at temperatures between −80° C. and 25° C. In some embodiments, the indexed tri-fold skin sample collector or placement sheet is sent to a diagnostic lab using UPS or FedEx.

In an exemplary embodiment, the patch stripping method further comprises preparing the skin sample prior to application of the adhesive patch. Preparation of the skin sample includes, but is not limited to, removing hairs on the skin surface, cleansing the skin surface and/or drying the skin surface. In some instances, the skin surface is cleansed with an antiseptic including, but not limited to, alcohols, quaternary ammonium compounds, peroxides, chlorhexidine, halogenated phenol derivatives and quinolone derivatives. In some instances, the alcohol is about 0 to about 20%, about 20 to about 40%, about 40 to about 60%, about 60 to about 80%, or about 80 to about 100% isopropyl alcohol. In some instances, the antiseptic is 70% isopropyl alcohol.

In some embodiments, the patch stripping method is used to collect a skin sample from the surfaces including, but not limited to, the face, head, neck, arm, chest, abdomen, back, leg, hand or foot. In some instances, the skin surface is not located on a mucous membrane. In some instances, the skin surface is not ulcerated or bleeding. In certain instances, the skin surface has not been previously biopsied. In certain instances, the skin surface is not located on the soles of the feet or palms.

The patch stripping method, devices, and systems described herein are useful for the collection of a skin sample from a skin lesion. A skin lesion is a part of the skin that has an appearance or growth different from the surrounding skin. In some instances, the skin lesion is pigmented. A pigmented lesion includes, but is not limited to, a mole, dark colored skin spot and a melanin containing skin area. In some embodiments, the skin lesion is from about 5 mm to about 16 mm in diameter. In some instances, the skin lesion is from about 5 mm to about 15 mm, from about 5 mm to about 14 mm, from about 5 mm to about 13 mm, from about 5 mm to about 12 mm, from about 5 mm to about 11 mm, from about 5 mm to about 10 mm, from about 5 mm to about 9 mm, from about 5 mm to about 8 mm, from about 5 mm to about 7 mm, from about 5 mm to about 6 mm, from about 6 mm to about 15 mm, from about 7 mm to about 15 mm, from about 8 mm to about 15 mm, from about 9 mm to about 15 mm, from about 10 mm to about 15 mm, from about 11 mm to about 15 mm, from about 12 mm to about 15 mm, from about 13 mm to about 15 mm, from about 14 mm to about 15 mm, from about 6 to about 14 mm, from about 7 to about 13 mm, from about 8 to about 12 mm and from about 9 to about 11 mm in diameter. In some embodiments, the skin lesion is from about 10 mm to about 20 mm, from about 20 mm to about 30 mm, from about 30 mm to about 40 mm, from about 40 mm to about 50 mm, from about 50 mm to about 60 mm, from about 60 mm to about 70 mm, from about 70 mm to about 80 mm, from about 80 mm to about 90 mm, and from about 90 mm to about 100 mm in diameter. In some instances, the diameter is the longest diameter of the skin lesion. In some instances, the diameter is the smallest diameter of the skin lesion.

The adhesive skin sample collection kit, in some embodiments, comprises at least one adhesive patch, a sample collector, and an instruction for use sheet. In an exemplary embodiment, the sample collector is a tri-fold skin sample collector comprising a peelable release panel comprising at least one adhesive patch, a placement area panel comprising a removable liner, and a clear panel. The tri-fold skin sample collector, in some instances, further comprises a barcode and/or an area for transcribing patient information. In some instances, the adhesive skin sample collection kit is configured to include a plurality of adhesive patches, including but not limited to 12, 11, 10, 9, 8, 7, 6, 5, 4, 3, 2, 1, from about 2 to about 8, from about 2 to about 7, from about 2 to about 6, from about 2 to about 4, from about 3 to about 6, from about 3 to about 8, from about 4 to about 10, from about 4 to about 8, from about 4 to about 6, from about 4 to about 5, from about 6 to about 10, from about 6 to about 8, or from about 4 to about 8. The instructions for use sheet provides the kit operator all of the necessary information for carrying out the patch stripping method. The instructions for use sheet preferably includes diagrams to illustrate the patch stripping method.

In some instances, the adhesive skin sample collection kit provides all the necessary components for performing the patch stripping method. In some embodiments, the adhesive skin sample collection kit includes a lab requisition form for providing patient information. In some instances, the kit further comprises accessory components. Accessory components include, but are not limited to, a marker, a resealable plastic bag, gloves and a cleansing reagent. The cleansing reagent includes, but is not limited to, an antiseptic such as isopropyl alcohol. In some instances, the components of the skin sample collection kit are provided in a cardboard box.

Tissue Sampling and Cellular Material

The methods and devices provided herein, in certain embodiments, involve applying an adhesive or other similar patch to the skin in a manner so that an effective or sufficient amount of a tissue, such as a skin sample, adheres to the adhesive matrix of the adhesive patch. For example, the effective or sufficient amount of a skin sample is an amount that removably adheres to a material, such as the matrix or adhesive patch. The adhered skin sample, in certain embodiments, comprises cellular material including nucleic acids and proteins. In some instances, the nucleic acid is RNA or DNA. An effective amount of a skin sample contains an amount of cellular material sufficient for performing a diagnostic assay. In some instances, the diagnostic assay is performed using the cellular material isolated from the adhered skin sample on the used adhesive patch. In some instances, the diagnostic assay is performed on the cellular material adhered to the used adhesive patch. In some embodiments, an effect amount of a skin sample comprises an amount of RNA sufficient to perform a gene expression analysis. Sufficient amounts of RNA includes, but not limited to, picogram, nanogram, and microgram quantities.

In still further or additional embodiments, the adhered skin sample comprises cellular material including nucleic acids such as RNA or DNA, or a polypeptide such as a protein, in an amount that is at least about 1 picogram. In some embodiments, the amount of cellular material is no more than about 1 nanogram. In further or additional embodiments, the amount of cellular material is no more than about 1 microgram. In still further or additional embodiments, the amount of cellular material is no more than about 1 gram.

In further or additional embodiments, the amount of cellular material is from about 1 picogram to about 1 gram. In further or additional embodiments, the cellular material comprises an amount that is from about 50 microgram to about 1 gram, from about 100 picograms to about 500 micrograms, from about 500 picograms to about 100 micrograms, from about 750 picograms to about 1 microgram, from about 1 nanogram to about 750 nanograms, or from about 1 nanogram to about 500 nanograms.

In further or additional embodiments, the amount of cellular material, including nucleic acids such as RNA or DNA, or a polypeptide such as a protein, comprises an amount that is from about 50 microgram to about 500 microgram, from about 100 microgram to about 450 microgram, from about 100 microgram to about 350 microgram, from about 100 microgram to about 300 microgram, from about 120 microgram to about 250 microgram, from about 150 microgram to about 200 microgram, from about 500 nanograms to about 5 nanograms, or from about 400 nanograms to about 10 nanograms, or from about 200 nanograms to about 15 nanograms, or from about 100 nanograms to about 20 nanograms, or from about 50 nanograms to about 10 nanograms, or from about 50 nanograms to about 25 nanograms.

In further or additional embodiments, the amount of cellular material, including nucleic acids such as RNA or DNA, or a polypeptide such as a protein, is less than about 1 gram, is less than about 500 micrograms, is less than about 490 micrograms, is less than about 480 micrograms, is less than about 470 micrograms, is less than about 460 micrograms, is less than about 450 micrograms, is less than about 440 micrograms, is less than about 430 micrograms, is less than about 420 micrograms, is less than about 410 micrograms, is less than about 400 micrograms, is less than about 390 micrograms, is less than about 380 micrograms, is less than about 370 micrograms, is less than about 360 micrograms, is less than about 350 micrograms, is less than about 340 micrograms, is less than about 330 micrograms, is less than about 320 micrograms, is less than about 310 micrograms, is less than about 300 micrograms, is less than about 290 micrograms, is less than about 280 micrograms, is less than about 270 micrograms, is less than about 260 micrograms, is less than about 250 micrograms, is less than about 240 micrograms, is less than about 230 micrograms, is less than about 220 micrograms, is less than about 210 micrograms, is less than about 200 micrograms, is less than about 190 micrograms, is less than about 180 micrograms, is less than about 170 micrograms, is less than about 160 micrograms, is less than about 150 micrograms, is less than about 140 micrograms, is less than about 130 micrograms, is less than about 120 micrograms, is less than about 110 micrograms, is less than about 100 micrograms, is less than about 90 micrograms, is less than about 80 micrograms, is less than about 70 micrograms, is less than about 60 micrograms, is less than about 50 micrograms, is less than about 20 micrograms, is less than about 10 micrograms, is less than about 5 micrograms, is less than about 1 microgram, is less than about 750 nanograms, is less than about 500 nanograms, is less than about 250 nanograms, is less than about 150 nanograms, is less than about 100 nanograms, is less than about 50 nanograms, is less than about 25 nanograms, is less than about 15 nanograms, is less than about 1 nanogram, is less than about 750 picograms, is less than about 500 picograms, is less than about 250 picograms, is less than about 100 picograms, is less than about 50 picograms, is less than about 25 picograms, is less than about 15 picograms, or is less than about 1 picogram.

In some embodiments, isolated RNA from a collected skin sample is reverse transcribed into cDNA, for example for amplification by PCR to enrich for target genes. The expression levels of these target genes are quantified by quantitative PCR in a gene expression test. In some instances, in combination with quantitative PCR, a software program performed on a computer is utilized to quantify RNA isolated from the collected skin sample. In some instances, a software program or module is utilized to relate a quantity of RNA from a skin sample to a gene expression signature, wherein the gene expression signature is associated with a disease such as skin cancer. In some embodiments, a software program or module scores a sample based on gene expression levels. In some embodiments, the sample score is compared with a reference sample score to determine if there is a statistical significance between the gene expression signature and a disease.

Computer Program

The methods, software, media, and systems disclosed herein comprise at least one computer processor, or use of the same. In some instances, the computer processor comprises a computer program. In some instances, a computer program includes a sequence of instructions, executable in the digital processing device's CPU, written to perform a specified task. In some instances, computer readable instructions are implemented as program modules, such as functions, features, Application Programming Interfaces (APIs), data structures, and the like, that perform particular tasks or implement particular abstract data types. In light of the disclosure provided herein, those of skill in the art will recognize that a computer program, in some embodiments, are written in various versions of various languages.

The functionality of the computer readable instructions, in certain embodiments, are combined or distributed as desired in various environments. In some instances, a computer program comprises one sequence of instructions. In some instances, a computer program comprises a plurality of sequences of instructions. In some instances, a computer program is provided from one location. In some instances, a computer program is provided from a plurality of locations. In some instances, a computer program includes one or more software modules. In some instances, a computer program includes, in part or in whole, one or more web applications, one or more mobile applications, one or more standalone applications, one or more web browser plug-ins, extensions, add-ins, or add-ons, or combinations thereof.

Web Application

In some instances, a computer program includes a web application. In light of the disclosure provided herein, those of skill in the art will recognize that a web application, in certain embodiments, utilizes one or more software frameworks and one or more database systems. In some instances, a web application is created upon a software framework such as Microsoft® .NET or Ruby on Rails (RoR). In some instances, a web application utilizes one or more database systems including, by way of non-limiting examples, relational, non-relational, feature oriented, associative, and XML database systems. Suitable relational database systems includes, by way of non-limiting examples, Microsoft® SQL Server, mySQL™, and Oracle®. Those of skill in the art will also recognize that a web application, in certain embodiments, is written in one or more versions of one or more languages. In some instances, a web application is written in one or more markup languages, presentation definition languages, client-side scripting languages, server-side coding languages, database query languages, or combinations thereof. In some instances, a web application is written to some extent in a markup language such as Hypertext Markup Language (HTML), Extensible Hypertext Markup Language (XHTML), or eXtensible Markup Language (XML). In some instances, a web application is written to some extent in a presentation definition language such as Cascading Style Sheets (CSS). In some instances, a web application is written to some extent in a client-side scripting language such as Asynchronous Javascript and XML (AJAX), Flash® Actionscript, Javascript, or Silverlight®. In some instances, a web application is written to some extent in a server-side coding language such as Active Server Pages (ASP), ColdFusion®, Perl, Java™, JavaServer Pages (SP), Hypertext Preprocessor (PHP), Python™, Ruby, Tcl, Smalltalk, WebDNA, or Groovy. In some instances, a web application is written to some extent in a database query language such as Structured Query Language (SQL). In some instances, a web application integrates enterprise server products such as IBM® Lotus Domino®. In some instances, a web application includes a media player element. In some instances, a media player element utilizes one or more of many suitable multimedia technologies including, by way of non-limiting examples, Adobe® Flash®, HTML 5, Apple® QuickTime®, Microsoft® Silverlight®, Java™, and Unity.

Mobile Application

In some instances, a computer program includes a mobile application provided to a mobile digital processing device. In some instances, the mobile application is provided to a mobile digital processing device at the time it is manufactured. In some instances, the mobile application is provided to a mobile digital processing device via the computer network described herein.

In some instances, the mobile application is created by techniques known to those of skill in the art using hardware, languages, and development environments known to the art. Those of skill in the art will recognize that mobile applications, in certain embodiments, are written in several languages. Suitable programming languages include, by way of non-limiting examples, C, C++, C#, Featureive-C, Java™, Javascript, Pascal, Feature Pascal, Python™, Ruby, VB.NET, WML, and XHTML/HTML with or without CSS, or combinations thereof.

Suitable mobile application development environments, in some instances, are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. In some instances, other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palmo OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry App World, App Store for Palm devices, App Catalog for webOS, Windows® Marketplace for Mobile, Ovi Store for Nokia® devices, Samsung® Apps, and Nintendo® DSi Shop.

Standalone Application

In some instances, a computer program includes a standalone application, which is a program that is run as an independent computer process, not an add-on to an existing process, e.g., not a plug-in. Those of skill in the art will recognize that standalone applications are often compiled. In some instances, a compiler is a computer program(s) that transforms source code written in a programming language into binary feature code such as assembly language or machine code. Suitable compiled programming languages include, by way of non-limiting examples, C, C++, Featureive-C, COBOL, Delphi, Eiffel, Java™, Lisp, Python™, Visual Basic, and VB .NET, or combinations thereof. Compilation are often performed, at least in part, to create an executable program. In some instances, a computer program includes one or more executable complied applications.

Web Browser Plug-in

In some instances, a computer program includes a web browser plug-in. In computing, a plug-in, in some instances, is one or more software components that add specific functionality to a larger software application. In some instances, makers of software applications support plug-ins to enable third-party developers to create abilities which extend an application, to support easily adding new features, and to reduce the size of an application. In some instances, when supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash© Player, Microsoft® Silverlight®, and Apple® QuickTime®. In some instances, the toolbar comprises one or more web browser extensions, add-ins, or add-ons. In some instances, the toolbar comprises one or more explorer bars, tool bands, or desk bands.

In view of the disclosure provided herein, those of skill in the art will recognize that several plug-in frameworks, in some instances, are available that enable development of plug-ins in various programming languages, including, by way of non-limiting examples, C++, Delphi, Java™, PHP, Python™, and VB .NET, or combinations thereof.

In some instances, web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple Safari, Opera Software® Opera, and KDE Konqueror. In some instances, web browser is a mobile web browser. In some instances, the mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

The medium, method, and system disclosed herein comprise one or more softwares, servers, and database modules, or use of the same. In view of the disclosure provided herein, software modules, in certain embodiments, are created by techniques known to those of skill in the art using machines, software, and languages known to the art. The software modules disclosed herein, in certain embodiments, are implemented in a multitude of ways. In some instances, a software module comprises a file, a section of code, a programming feature, a programming structure, or combinations thereof. In some instances, a software module comprises a plurality of files, a plurality of sections of code, a plurality of programming features, a plurality of programming structures, or combinations thereof. In some instances, the one or more software modules comprises, by way of non-limiting examples, a web application, a mobile application, and a standalone application. In some instances, software modules are in one computer program or application. In some instances, software modules are in more than one computer program or application. In some instances, software modules are hosted on one machine. In some instances, software modules are hosted on more than one machine. In some instances, software modules are hosted on cloud computing platforms. In some instances, software modules are hosted on one or more machines in one location. In some instances, software modules are hosted on one or more machines in more than one location.

Databases

The medium, method, and system disclosed herein comprise one or more databases, or use of the same. In view of the disclosure provided herein, those of skill in the art will recognize that many databases, in certain embodiments, are suitable for storage and retrieval of geologic profile, operator activities, division of interest, and/or contact information of royalty owners. Suitable databases include, by way of non-limiting examples, relational databases, non-relational databases, feature oriented databases, feature databases, entity-relationship model databases, associative databases, and XML databases. In some instances, a database is internet-based. In some instances, a database is web-based. In some instances, a database is cloud computing-based. In some instances, a database is based on one or more local computer storage devices.

Definitions

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/− 10% thereof, or 10% below the lower listed limit and 10% above the higher listed limit for the values listed for a range.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

As disclosed herein, a gene of interest described above comprises MMP1 (also known as matrix metallopeptidase 1, interstitial collagenase, fibroblast collagenase, or CLGN). In some instances, MMP1 has Gene ID: 4312.

As disclosed herein, a gene of interest described above comprises S100A7 (also known as S100 calcium binding protein A7, PSOR1, or psoriasin 1). In some instances, S100A7 has Gene ID: 6278.

As disclosed herein, a gene of interest described above comprises CMPK2 (also known as cytidine/uridine monophosphate kinase 2, nucleoside-diphosphate kinase, thymidine monophosphate kinase 2, TMPK2, TYKi, or NDK). In some instances, CMPK2 has Gene ID: 129607.

As disclosed herein, a gene of interest described above comprises IRF7 (also known as interferon regulatory factor 7 or IMD39). In some instances, IRF7 has Gene ID: 3665.

As disclosed herein, a gene of interest described above comprises IGFL1 (also known as IGF like family member 1, APRG644, or UNQ644). In some instances, IGFL1 has Gene ID: 374918.

As disclosed herein, a gene of interest described above comprises CXCL1 (also known as C-X-C motif chemokine ligand 1, GRO1 oncogene (melanoma growth stimulating activity, alpha), growth-regulated alpha protein, fibroblast secretory protein, NAP-3, SCYB1, or GRO1). In some instances, CXCL1 has Gene ID: 2919.

As disclosed herein, a gene of interest described above comprises UPP1 (also known as Uridine phosphorylase 1, UrdPase 1, UP, UPASE, or UPP). In some instances, UPP1 has Gene ID: 7378.

As disclosed herein, a gene of interest described above comprises DEFB4A (also known as defensin beta 4A, skin-antimicrobial peptide 1, DEFB102, or HBD-2). In some instances, DEFB4A has Gene ID: 1673.

As disclosed herein, a gene of interest described above comprises FOS (also known as Fos proto-oncogen, AP-1 transcription factor subunit; FBJ murine osteosarcoma viral oncogene homolog; G0/G1 switch regulatory protein 7; C-FOS; GOS7; or P55). In some instances, FOS has Gene ID: 2353.

As disclosed herein, a gene of interest described above comprises OAS3 (also known as 2'-5'-oligoacehylate synthetase 3, P100 OA, or P100). In some instances, OAS3 has Gene ID: 4940.

As disclosed herein, a gene of interest described above comprises SCD5 (also known as stearoyl-CoA desaturase 5, acyl-CoA-desaturase 4, SCD4, SCD2, or FADS4). In some instances, SCD5 has Gene ID: 79966.

As disclosed herein, a gene of interest described above comprises RTP4 (also known as receptor transporter protein 4, 28KDa interferon-responsive protein, 3CxxC-type zinc finger protein 4, or IFRG28). In some instances, RTP4 has Gene ID: 64108.

As disclosed herein, a gene of interest described above comprises VEGFA (also known as vascular endothelial growth factor A or VPF). In some instances, VEGFA has Gene ID: 7422.

As disclosed herein, a gene of interest described above comprises COL5A2 (also known as collagen type V alpha 2 chain, AB collagen, or EDSC). In some instances, COL5A2 has Gene ID: 1290.

As disclosed herein, a gene of interest described above comprises IL24 (also known as ST16, MDA7, FISP, or MOBS). In some instances, IL24 has Gene ID: 11009.

As disclosed herein, a gene of interest described above comprises AADACL2 (also known as arylacetamide deacetylase-like 2). In some instances, AADACL2 has Gene ID: 344752.

As disclosed herein, a gene of interest described above comprises PTCH1 (also known as patched 1 or BCNS). In some instances, PTCH1 has Gene ID: 5727.

As disclosed herein, a gene of interest described above comprises CD68 (also known as scavenger receptor class D, member 1; macrophage antigen CD68, GP110, or LAMP4). In some instances, CD68 has Gene ID: 968.

As disclosed herein, a gene of interest described above comprises PRKACA (also known as protein kinase CAMP-activated catalytic subunit alpha or PPNAD4). In some instances, PRKACA has Gene ID: 5566.

As disclosed herein, a gene of interest described above comprises SPP1 (also known as secreted phosphoprotein 1, osteopontin, nephropontin, BNSP, OPN, or BSPI). In some instances, SPP1 has Gene ID: 6696.

EXAMPLES

The following examples are given for the purpose of illustrating various embodiments of the disclosure and are not meant to limit the present disclosure in any fashion. The present examples, along with the methods described herein are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

Example 1

Figure 2B:
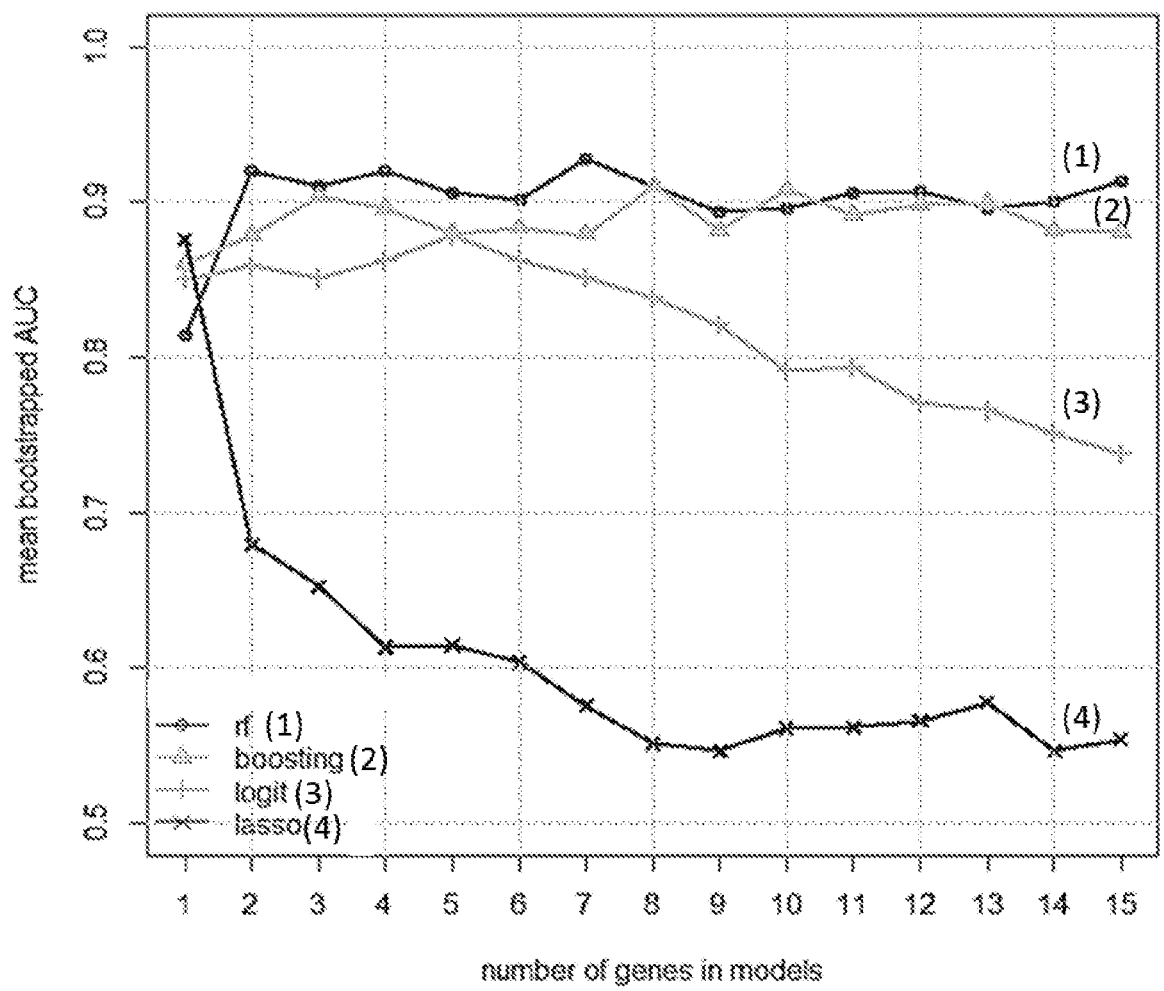

Non-Invasive Gene Expression Assay for Cutaneous Basal Cell and Squamous Cell Carcinoma A qPCR gene expression test was designed using identified target genes. The identified target genes were evaluated in prospectively collected basal cell carcinoma (BCC), squamous cell carcinoma (SCC), actinic keratosis (AK), seborrheic keratosis (SK), and normal samples obtained from subjects via non-invasive adhesive patch biopsies. Total RNA were extracted from these samples and quantified with real time quantitative PCR (qPCR, TaqMan qPCR) based on a house keeping gene (beta-actin). Cycle threshold (Ct) values from qPCR analyses were used to demonstrate changes in target gene expression. Algorithms were developed (FIGS. 2A-2B), trained, and subjected to primary validation in histopathologically confirmed samples (n=160 cases). The variables for analysis included interactions among MMP1, S100A7, CMPK2, IRF7, IGFL1, CXCL1, UPP1, DEFB4A, FOS, OAS3, SCD5, RTP4, and VEGFA genes as seen in Table 1 and Table 2.

Figure 3A:
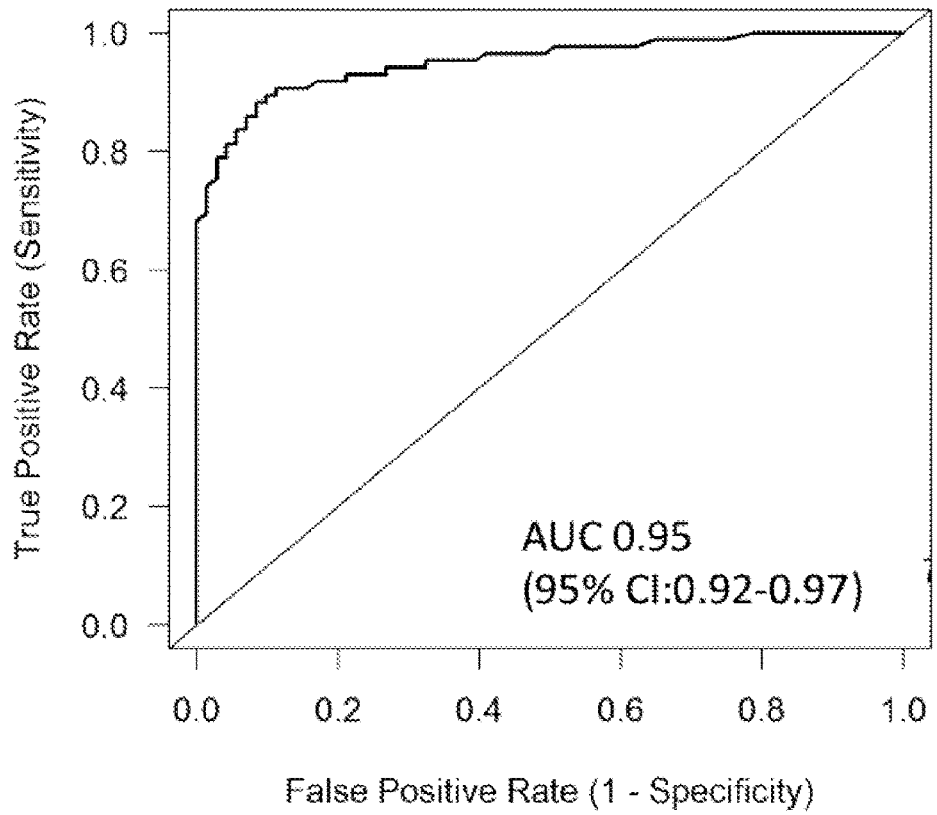
FIG. 3A-FIG. 3B illustrate graphs of an assay area under a curve (AUC) from the random forest (rf) analysis model.
Figure 3B:
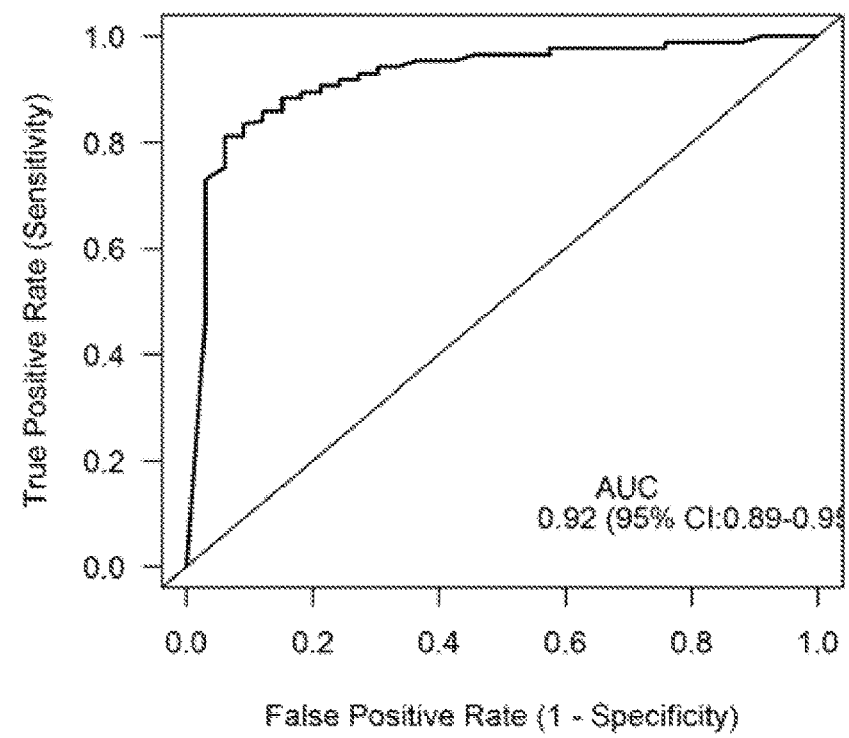

Gene expression changes of the target genes in the samples (cancer or non-cancer) were analyzed and compared with target-specific qPCR that received a normalized input of total RNA from each sample. Cancer samples and non-cancer samples were differentiated on the different gene expression patterns of these target genes. Using a 13-target gene panel (MMP1, S100A7, CMPK2, IRF7, IGFL1, CXCL1, UPP1, DEFB4A, FOS, OAS3, SCD5, RTP4, and VEGFA), BCC and SCC samples were differentiated from AK and other non-cancerous skin lesions of similar appearance with a sensitivity of 91% (95% CI 86%-95%) and a specificity of 87% (95% CI 80%-92%) based on 160 non-invasively collected adhesive patch skin biopsies (p<0.001) when employing the best performing random forest (rf) model. An area under the curve (AUC) value of 0.95 was observed (FIG. 3A) when comparing BCC and SCC to AK, SK, and NML samples. AUC values were also determined following comparison of BCC and SCC with SK samples (FIG. 3B).

This example shows that non-invasive gene expression analysis differentiates primary cutaneous BCC and SCC samples from benign and precursor lesions such as AK with high sensitivity and specificity.

Example 2

Non-Invasive Gene Expression Assay Utilizing a 9-Target Gene Panel

Figure 4:
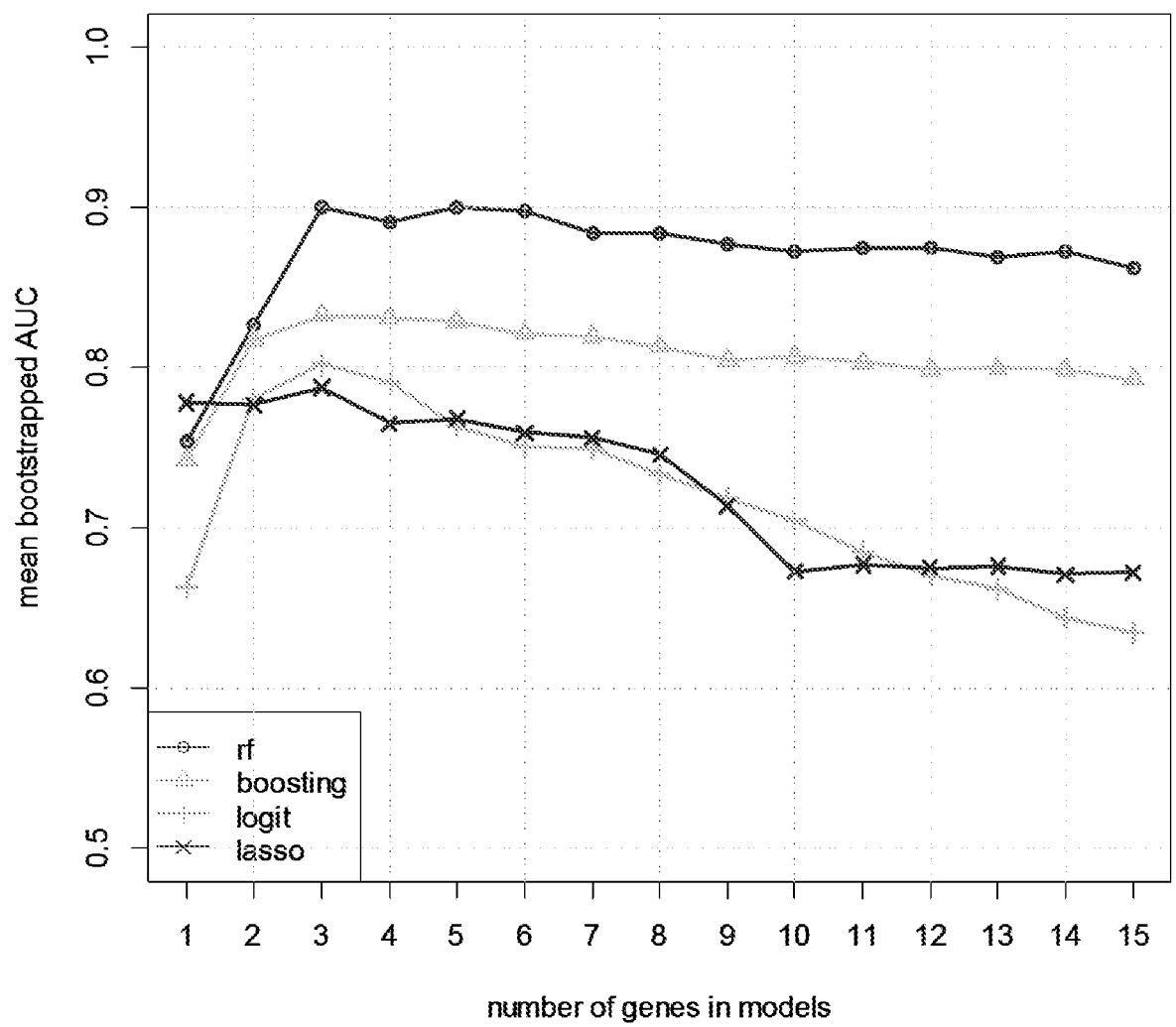
FIG. 4 shows algorithmic models for comparison of basal cell carcinoma (BCC) and squamous cell carcinoma (SCC) to actinic keratosis (AK), seborrheic keratosis (SK), and normal samples.
Figure 5A:
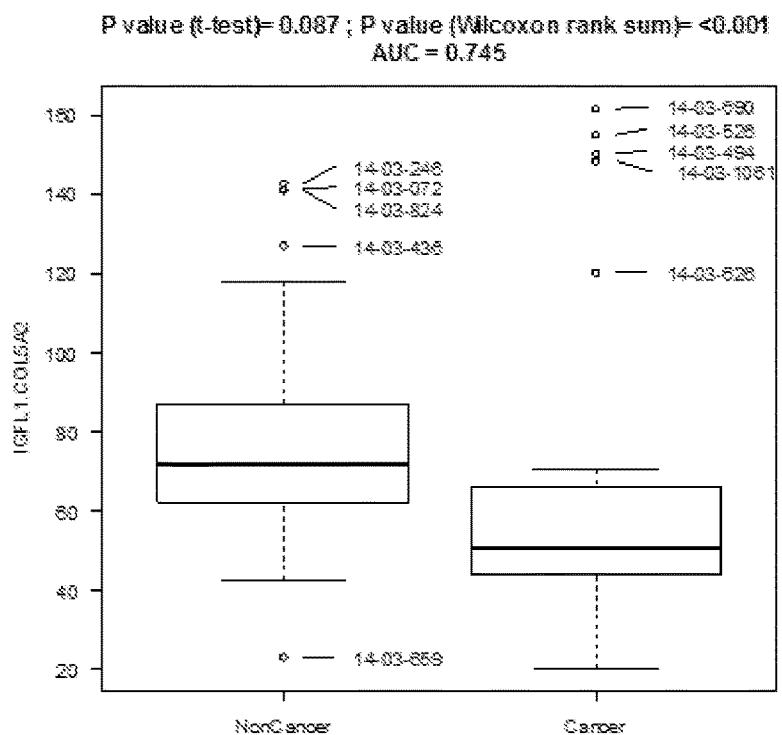
FIG. 5A-FIG. 5E show the boxplots of IGFL1, COL5A2 (FIG. 5A); IL24, AADACL2 (FIG. 5B); PTCH1, CD68 (FIG. 5C); PRKACA, SPP1 (FIG. 5D); or AADACL2, MMP1 (FIG. 5E) from Table 3.
Figure 5B:
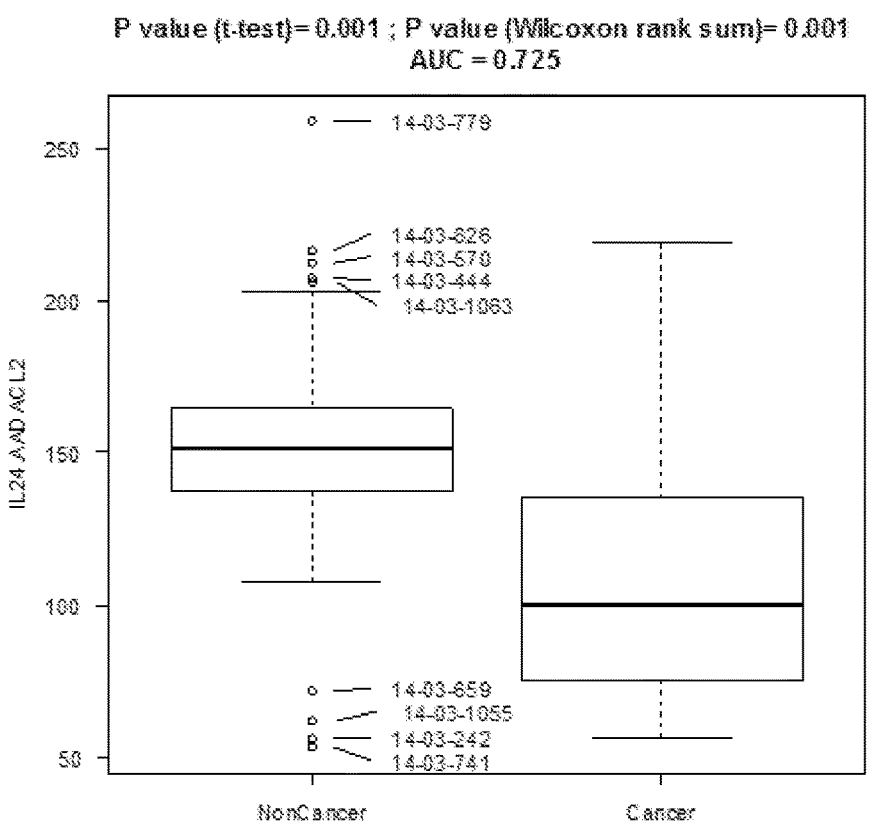
Figure 5C:
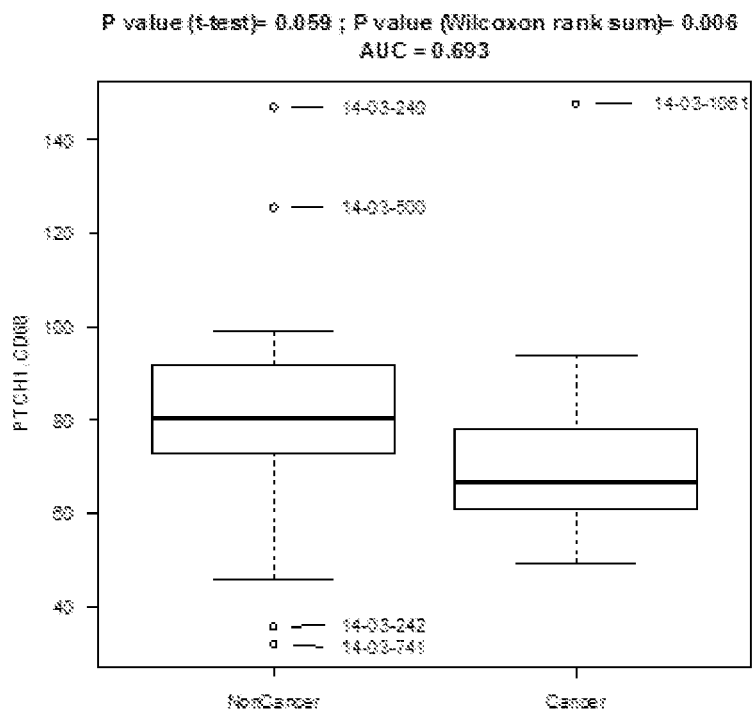
Figure 5D:
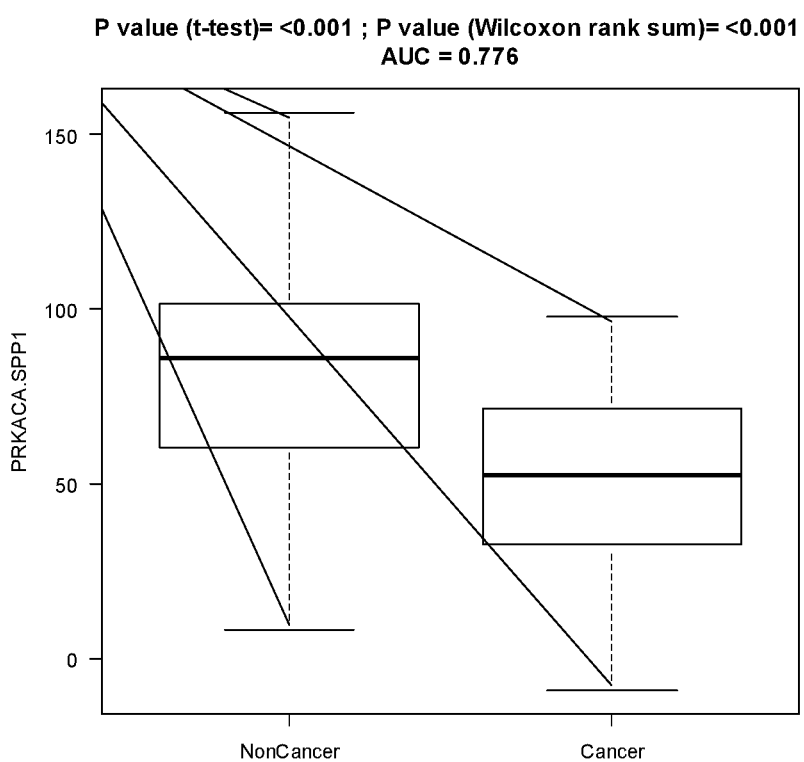
Figure 5E:
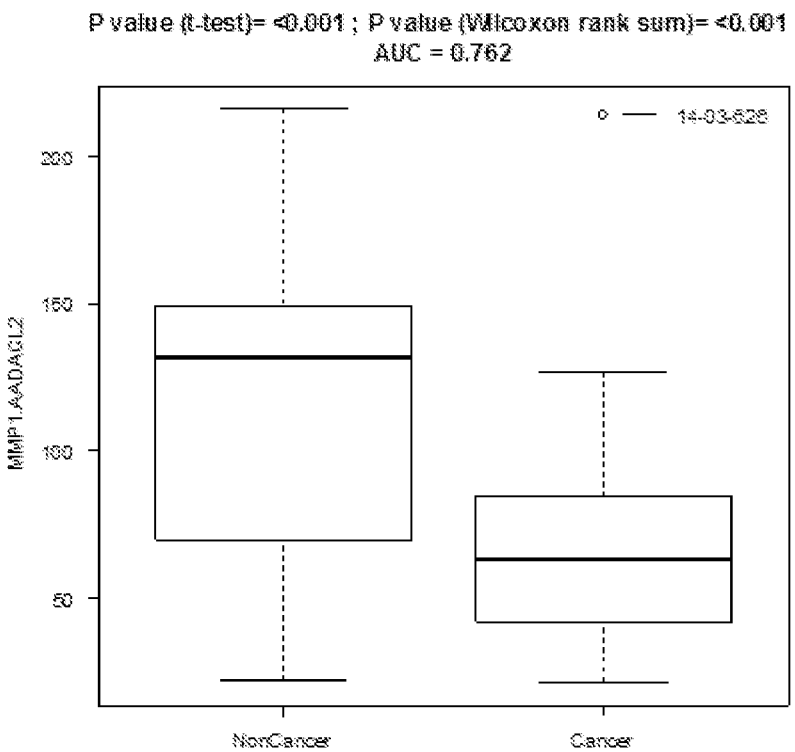

A qPCR gene expression test was designed using identified target genes. The identified target genes were evaluated in prospectively collected basal cell carcinoma (BCC), squamous cell carcinoma (SCC), actinic keratosis (AK), seborrheic keratosis (SK), and normal samples obtained from subjects via non-invasive adhesive patch biopsies. Total RNA were extracted from these samples and quantified with real time quantitative PCR (qPCR, TaqMan qPCR) based on a house keeping gene (beta-actin). Cycle threshold (Ct) values from qPCR analyses were used to demonstrate changes in target gene expression. Algorithms were developed (FIG. 4), trained, and subjected to primary validation in histopathologically confirmed samples. The variables for analysis included interactions among IGFL1, MMP1, COL5A2, IL24, AADACL2, PTCH1, CD68, PRKACA, and SPP1 as seen in Table 3.

Figure 6A:
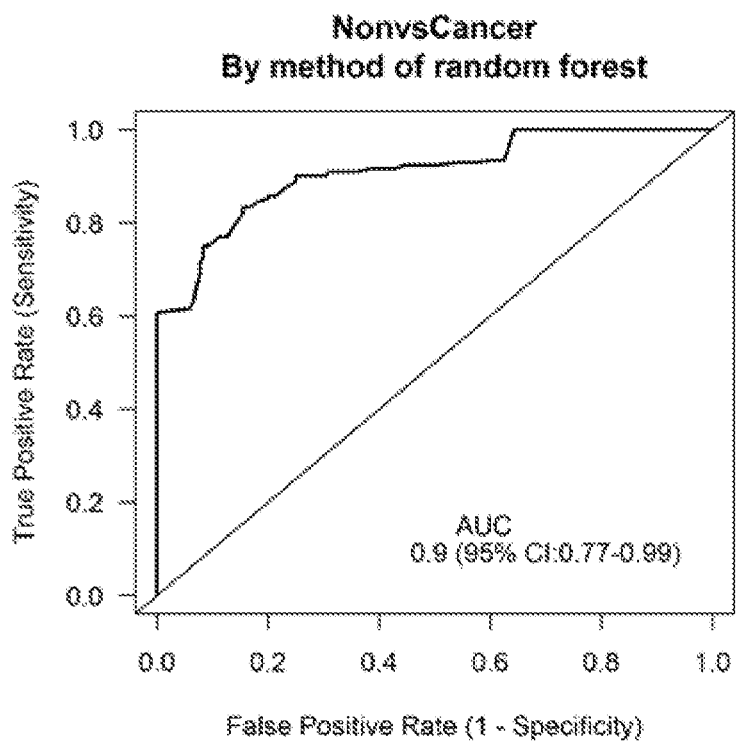

Gene expression changes of the target genes in the samples (cancer or non-cancer) were analyzed and compared with target-specific qPCR that received a normalized input of total RNA from each sample. Cancer samples and non-cancer samples were differentiated on the different gene expression patterns of these target genes. Using a 9-target gene panel (IGFL1, MMP1, COL5A2, IL24, AADACL2, PTCH1, CD68, PRKACA, and SPP1) (FIGS. 5A-5E) BCC and SCC samples were differentiated from AK and other non-cancerous skin lesions of similar appearance with a sensitivity of about 90% and a specificity of from about 70% to 75% (FIGS. 6A-6C).

This example shows that non-invasive gene expression analysis differentiates BCC and SCC samples from benign and precursor lesions such as AK with high sensitivity and specificity.

Example 3

Biplex PCR Amplifications of CDKN2A and TERT Exons

FIG. 7A shows an exemplary biplex PCR amplification of CDKN2A and TERT exons. FIG. 7B shows an exemplary Sanger sequencing of CDKN2A and TERT wild-type sequences. The locations of the CDKN2A mutations are further denoted in FIG. 7B. The PCR reaction was prepared based on the reaction setup illustrated in Table 5.

|  | Vol (µl) |
|---|---|
| H2O | 3.7 |
| AccuStart II GelTrack PCR SuperMix (2x) | 12.5 |
| Forward Primer (5 uM) (CDKN2A) | 0.5 |
| Reverse Primer (5 uM) (CDKN2A) | 0.5 |
| Forward Primer (5 uM) (TERT) | 1.0 |
| Reverse Primer (5 uM) (TERT) | 1.0 |
| DMSO (3%) | 0.8 |
| gDNA, 100 pg total input | 5.0 |
| Total | 25.0 |

Example 4

PCR Amplification of PTCH1

About 305 BCC samples and about 25 SCC samples were processed for detection mutations in PTCH1. About 167 BCC PTCH1 mutations and about 14 SCC PTCH1 mutations were detected from the tested samples.

Figure 8A:
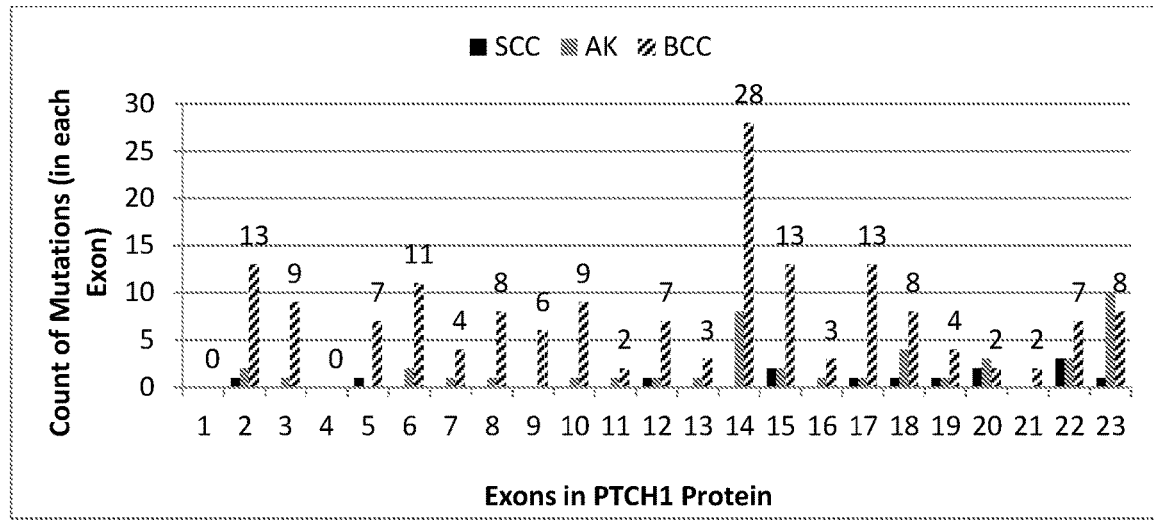
FIGS. 8A and 8B illustrate the mutation analysis of exemplary exons in PTCH1.
Figure 8B:
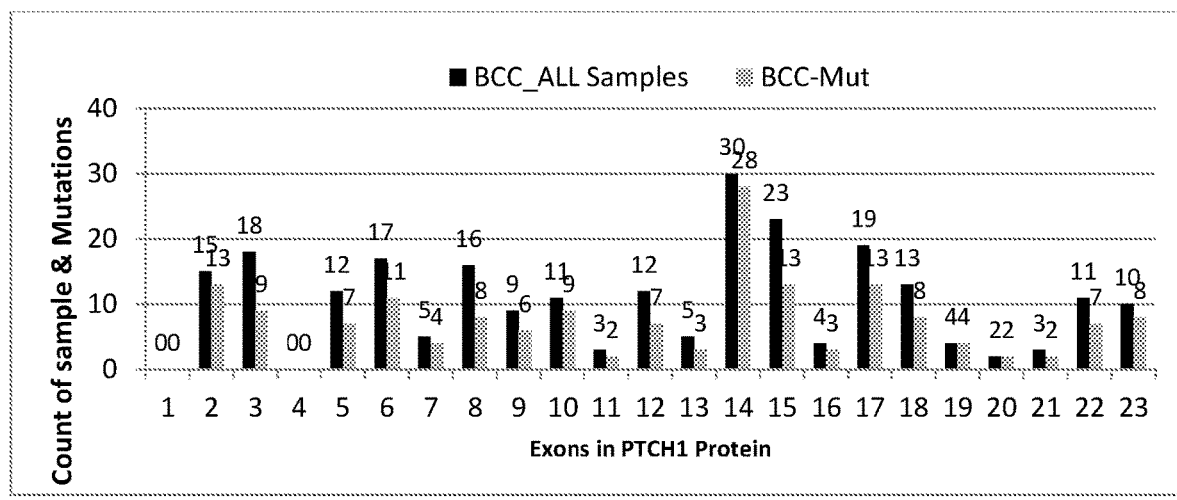

FIGS. 8A and 8B illustrate the mutation analysis of exemplary exons in PTCH1. FIG. 8A shows the number of mutations detected with respect to each exon from BCC, SCC, and AK. FIG. 8B shows the number of exons detected and the number of mutations detected within each exon in the tested BCC samples.

Figure 9:
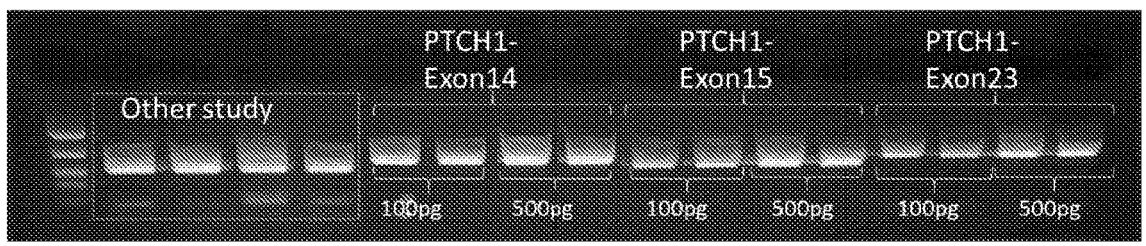
FIG. 9 illustrates the PCR amplification of exon 14, exon 15, and exon 23.

FIG. 9 illustrates the PCR amplification of exon 14, exon 15, and exon 23.

The PCR reaction was prepared based on the reaction setup illustrated in Table 6.

|  | Vol (µl) |
|---|---|
| H2O | 5.50 |
| AccuStart II GelTrack PCR SuperMix (2x) | 12.50 |
| Ptch 1 Forward (5 uM) | 1.00 |
| Ptch 1 Reverse (5 uM) | 1.00 |
| gDNA, 100 pg/ul | 5.00 |
| Total | 25.00 |

Example 5

PCR Amplification of TP53

Figure 10A:
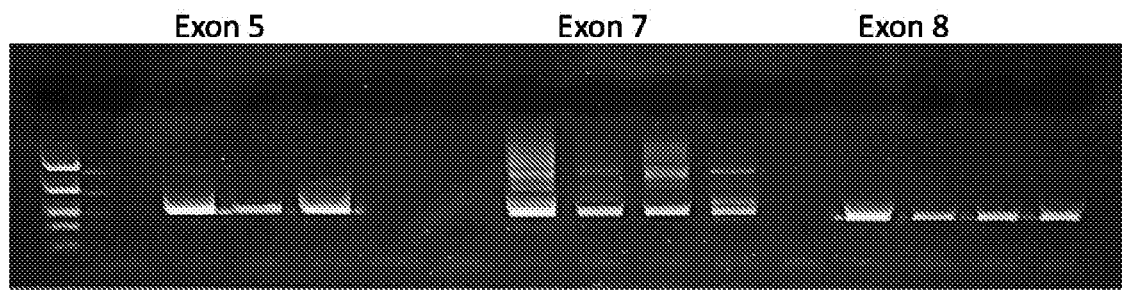
FIG. 10A illustrates the PCR amplification of exon 5, exon 7, and exon 8.
Figure 10B:
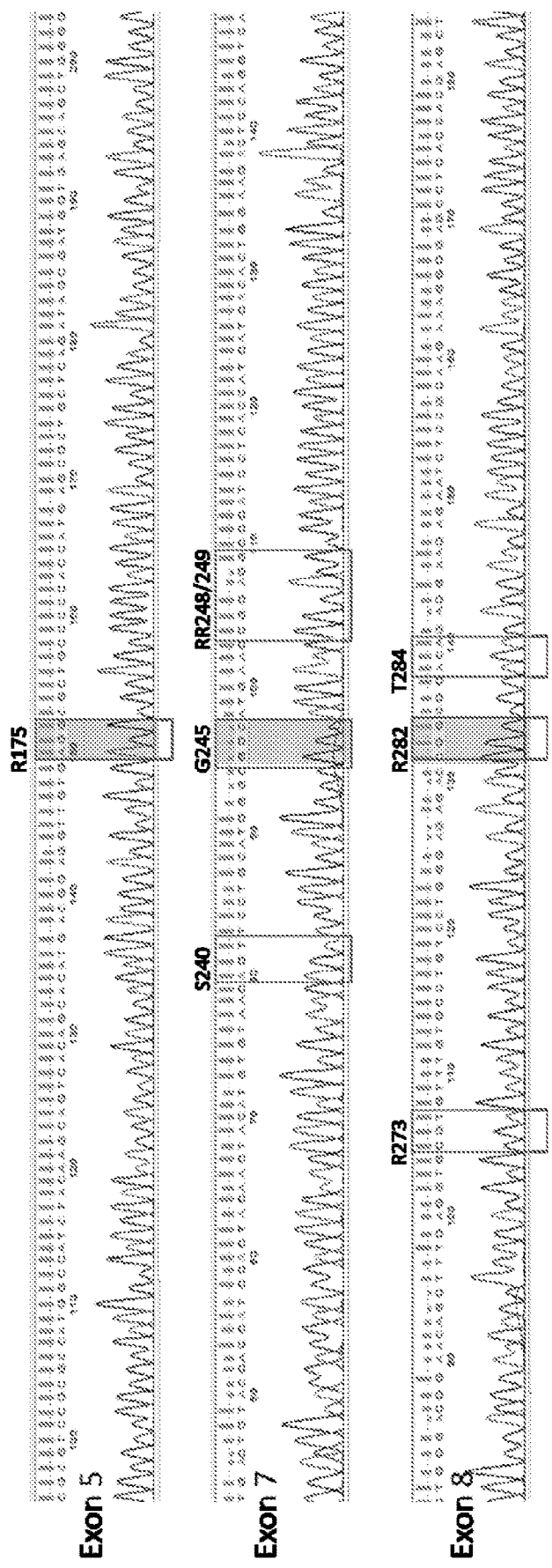
FIG. 10B shows the mutation location within each exon sequence.

FIG. 10A illustrates the PCR amplification of exon 5, exon 7, and exon 8. FIG. 10B shows the mutation location within each exon sequence. The PCR reaction was prepared based on the reaction setup illustrated in Table 7.

|  | Vol (µl) |
|---|---|
| H2O | 5.50 |
| AccuStart II GelTrack PCR SuperMix (2x) | 12.50 |
| TP53 Ex 5, 7, 8 F (5 uM) | 1.00 |
| TP53 Ex 5, 7, 8 R (5 uM) | 1.00 |
| gDNA, 100 pg/ul | 5.00 |
| Total | 25.00 |

Example 6

Co-Isolation of RNA and DNA Using Silica-Coated Magnetic Beads

Skin samples were collected with adhesive patches from forehead of adult volunteers, each patch was cut by half, and each half was used side-by-side for either cell lysis and nucleic acid extraction with in-house procedure or for cell lysis and nucleic acid extraction with a commercial test kit. The 2 halves were randomly split and used in each comparison test.

The percentage of RNA and DNA recovery was tested utilizing a mixture of silica-coated magnetic beads (Accu-Bead from Bioneer) (referenced as DT MB in the figure) and magnetic beads from Zymo Research (referenced as Zymo MB in the figure). After incubation, the magnetic beads in these tubes were washed either in a wash buffer prepared in-house or in a wash buffer from Zymo Research, and finally all samples were eluted in an in-house elution buffer. Total RNA and gDNA from all eluents were shown in FIG.

Figure 11:
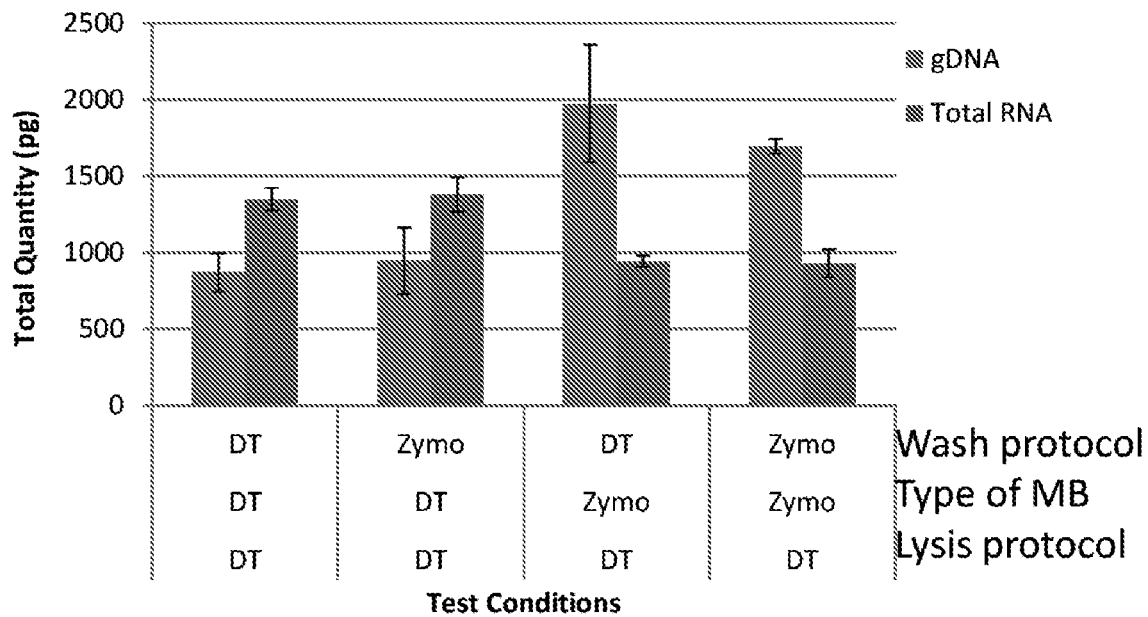
FIG. 11 illustrates total RNA and gDNA obtained from the tested eluents.

11. As illustrated in FIG. 11, the DT MB provided higher recovery of total RNA while the Zymo MB provided higher recovery of gDNA.

Figure 12:
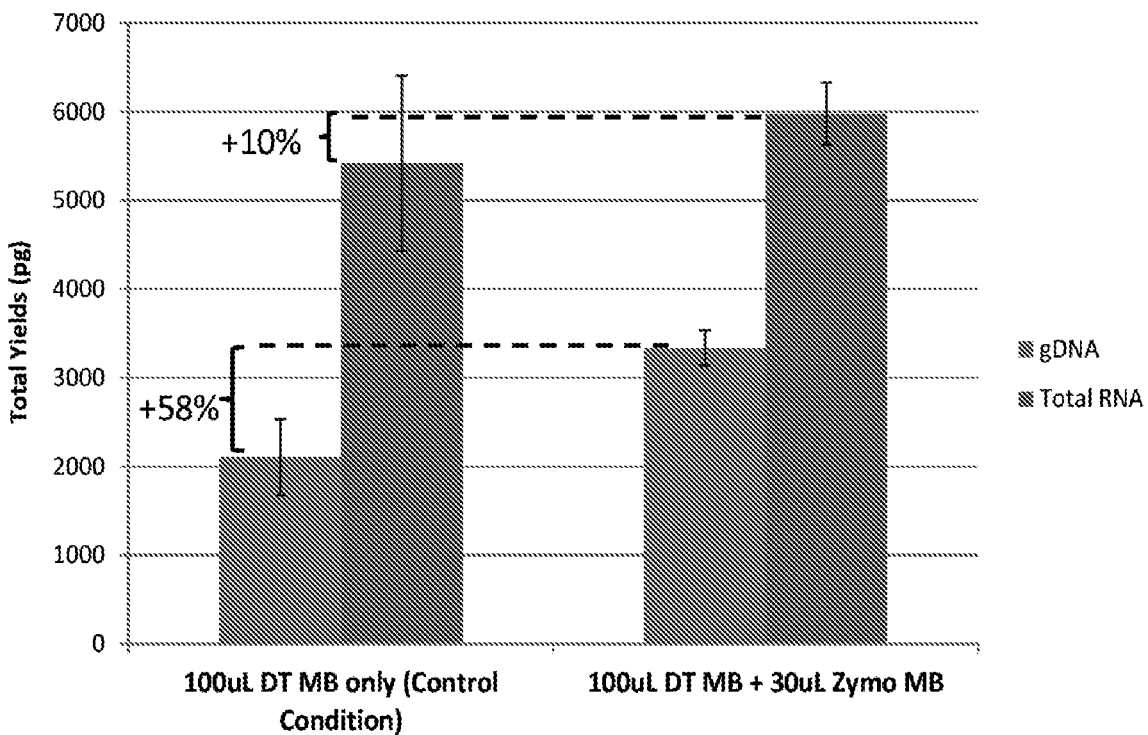
FIG. 12 illustrates gDNA and total RNA extraction utilizing a 100 µL DT MB:30 µL Zymo MB ratio compared to the control, which contains 100 µL of DT MB.

Based on the results from FIG. 11, different volume ratios of the DT MB and Zymo MB were tested. FIG. 12 illustrates gDNA and total RNA extraction utilizing a 100 μL DT MB:30 μL Zymo MB ratio compared to the control, which contains 100 μL of DT MB.

Figure 13A:
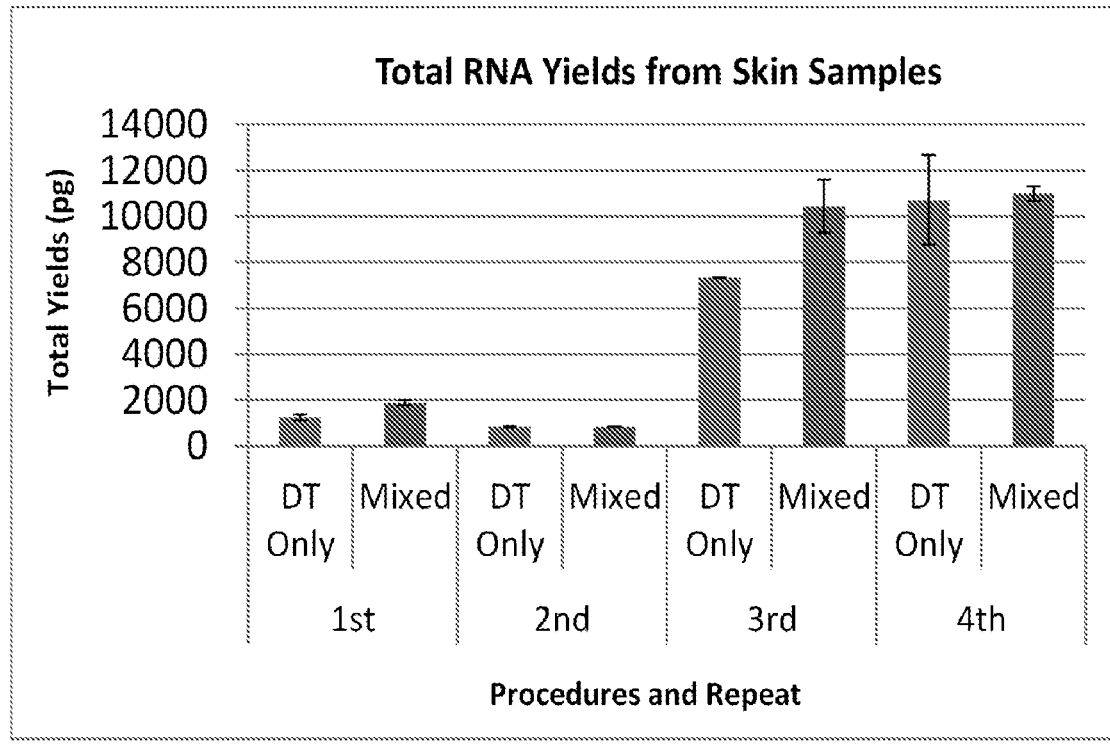
FIG. 13A-FIG. 13B show 4 exemplary follow-up studies comparing the recovery of RNA (FIG. 13A) and gDNA (FIG. 13B) between DT MB, Zymo MB, and a mixture of DT MB and Zymo MB.
Figure 13B:
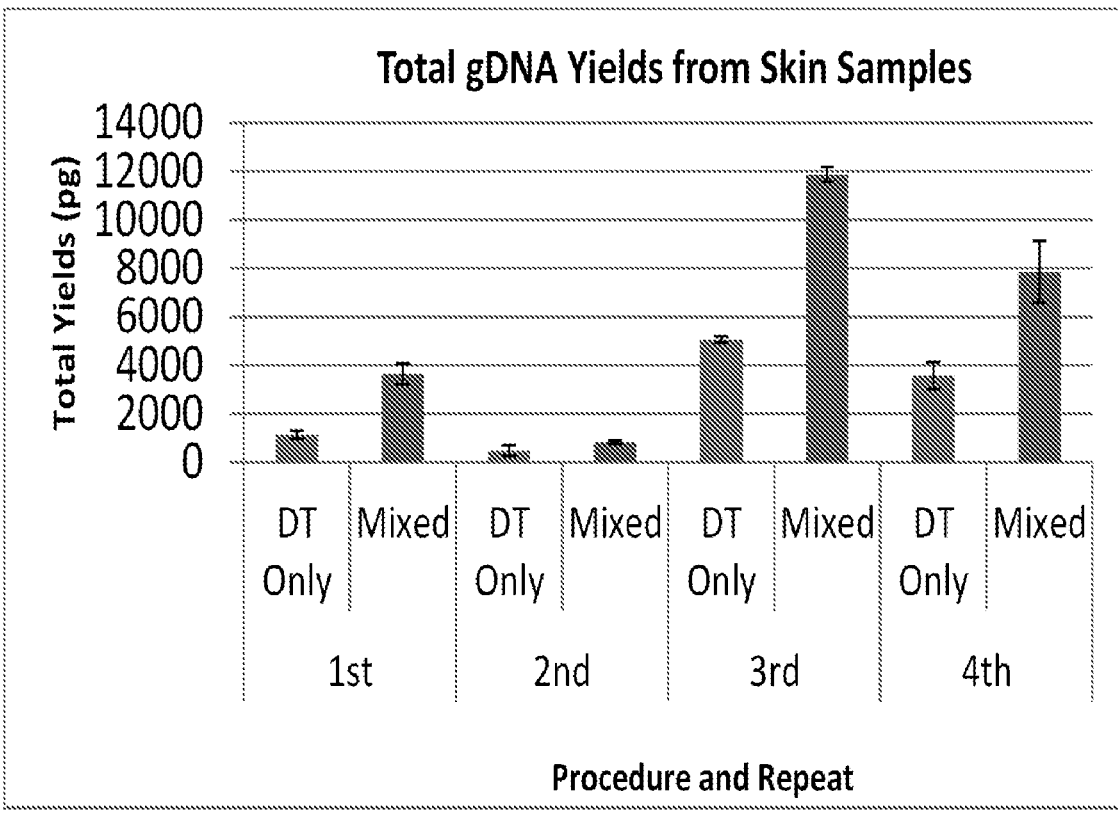

Four repeat skin sample extraction runs were made to compare side-by-side the procedure utilizing the mixed beads to the procedure utilizing single source beads. Forehead skin samples were collected with adhesive patches from adult volunteers, lysed in bulk volume with lysis buffer and then split to tubes to incubate with either the 2 types of beads ('Mixed') or the single type of bead ('DT Only'). The rest steps (bead washing and nucleic acid elution) followed. In each run, the DT Only and the Mix use the same sources of skin samples but the 4 runs were done on different days on skin samples collected from different adult volunteers. FIG. 13A-FIG. 13B show 4 exemplary follow-up studies comparing the recovery of RNA and gDNA between DT MB, Zymo MB, and a mixture of DT MB and Zymo MB.

Figure 14A:
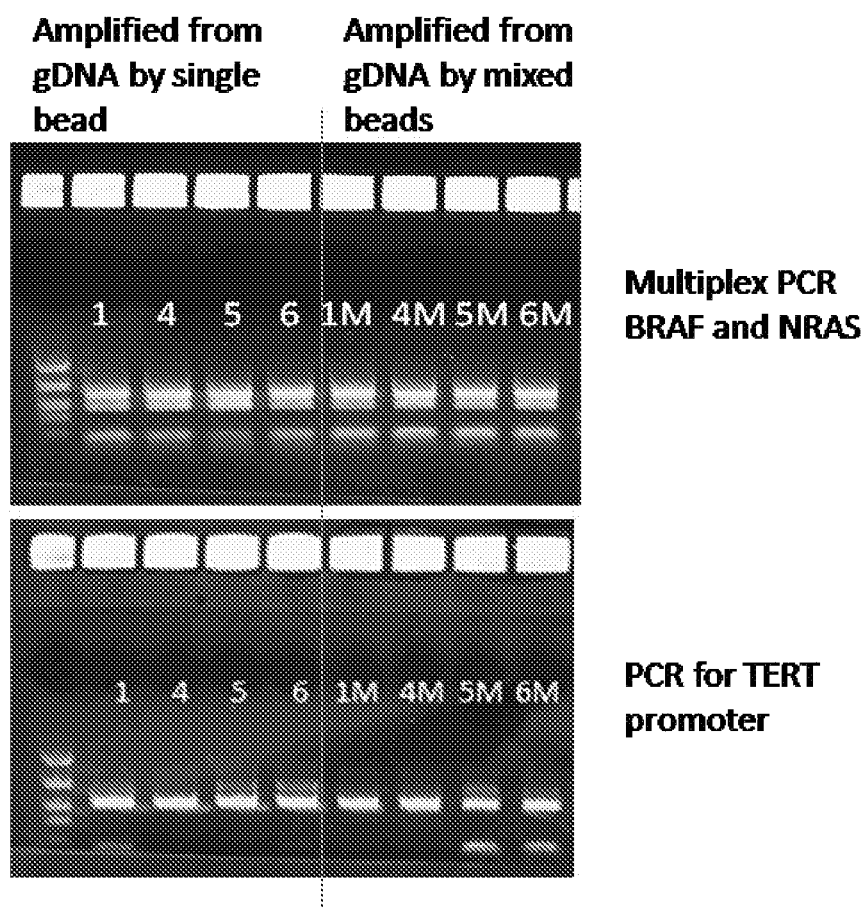
FIG. 14A shows PCR amplification of multiplex BRAF and NRAS amplicons (top) and TERT amplicon (bottom) from gDNA in isolated nucleic acid (NA) samples.

Gene expressions of 12 RNA samples isolated from forehead skins collected on adhesive patches from 6 adult volunteers were analyzed. Skin samples from the subjects were lysed and split for nucleic acid extraction. Beta-actin (control) and genes from the 9-target gene panel described in Example 2 were detected. Melanoma marker genes such as LINC and PRAME were not detected.

gDNA in the isolated NA from the same samples used for gene expression analysis were also tested for mutation. FIG. 14A shows PCR amplification of multiplex BRAF and NRAS amplicons (top) and TERT amplicon (bottom) from gDNA in these isolated NA samples. Samples 1, 4, 5 and 6 were from gDNA isolated by the old procedure (with DT only bead) and samples 1M, 4M, 5M and 6M were from gDNA isolated by the new procedure (with mixed beads). All samples were amplified well in PCR.

Figure 14B:
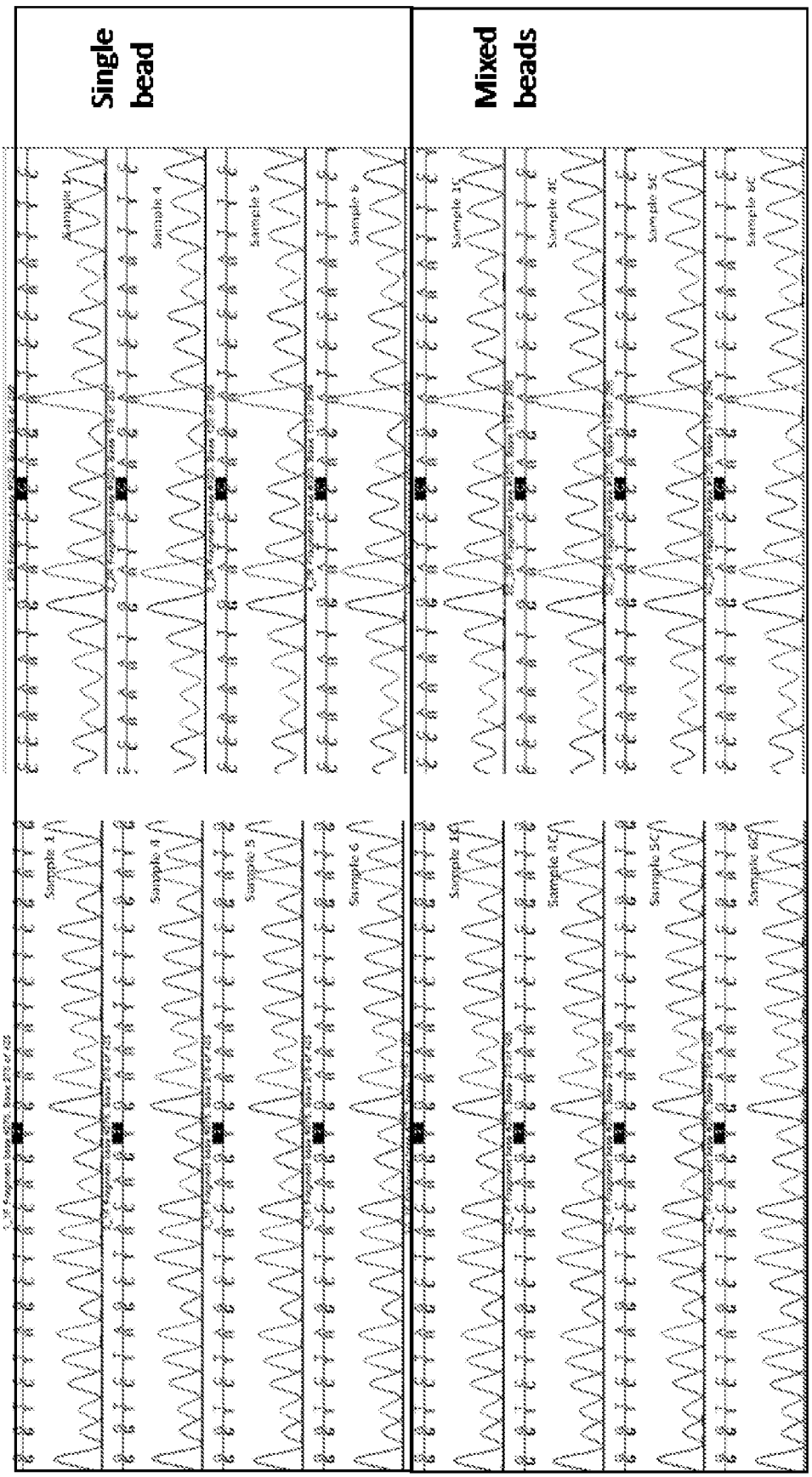
FIG. 14B shows chromatograms of BRAF V600 and 469 amplicons from the 8 samples, 4 isolated using DT only bead and 4 isolated using mixed beads.
Figure 14C:
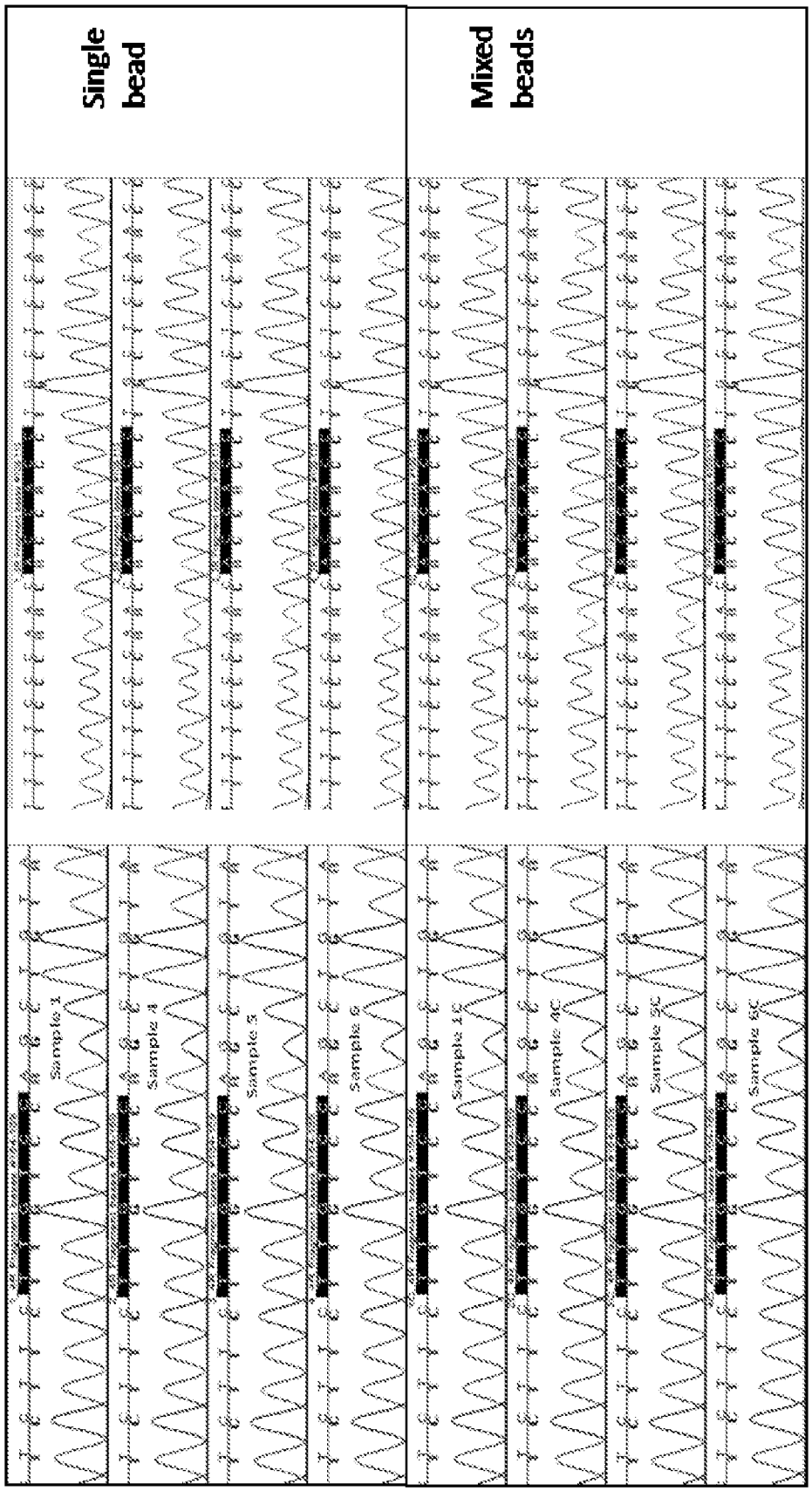
FIG. 14C shows chromatograms of NRAS 12_13 and 61 amplicons from the 8 samples, 4 isolated using DT only bead and 4 isolated using mixed beads.
Figure 14D:
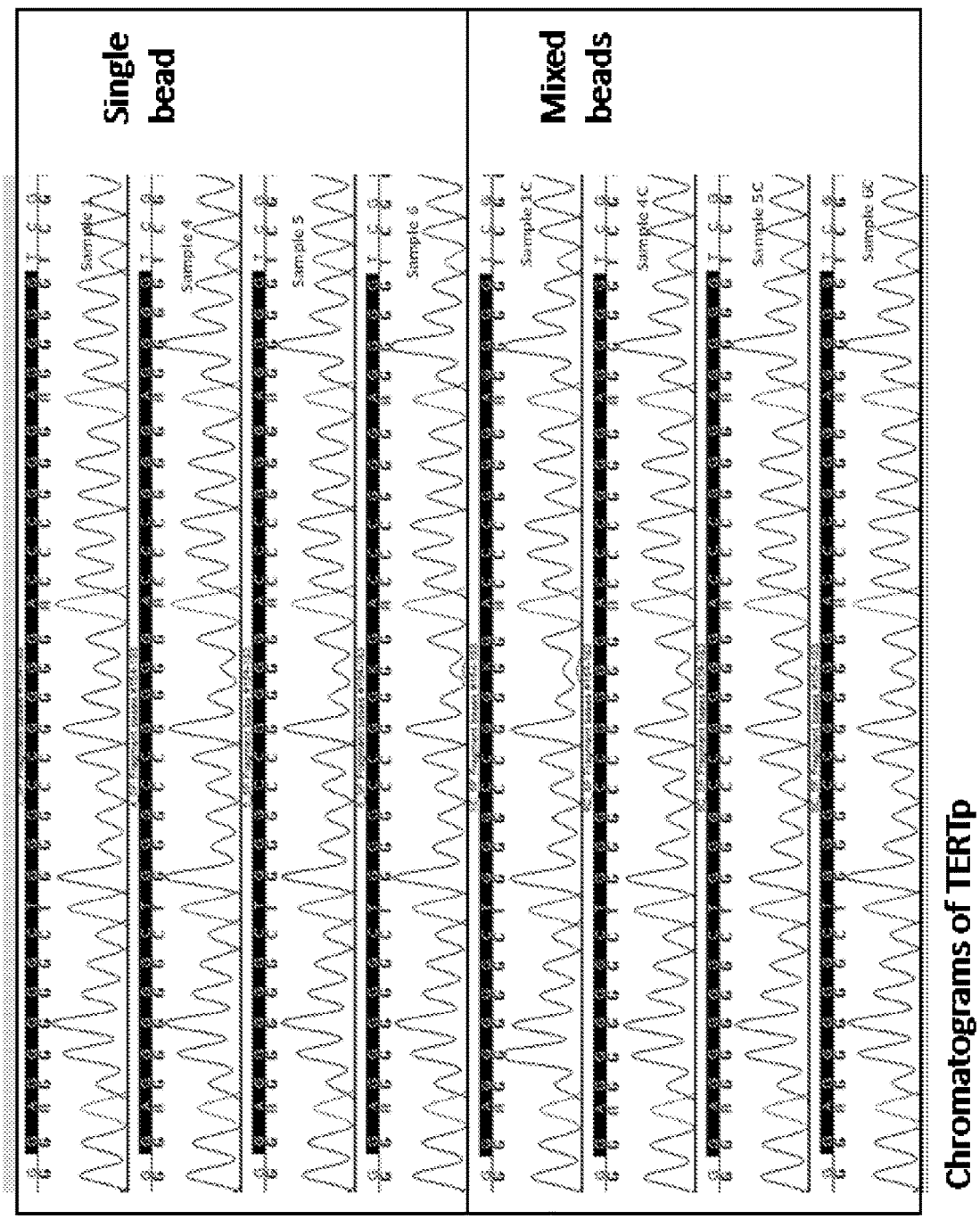
FIG. 14D shows chromatograms of TERT amplicons from the 8 samples, 4 isolated using DT only bead and 4 isolated using mixed beads.

FIG. 14B-FIG. 14C show chromatograms of Sanger sequencing on amplicons for BRAF V600, and G469, and NRAS G12,13 and NRAS Q61 from PCR. FIG. 14D shows chromatogram of Sanger sequencing on TERT amplicon from PCR reaction.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method for non-invasively identifying a non-melanoma skin cancer (NMSC), the NMSC being basal cell carcinoma (BCC) or squamous cell carcinoma (SCC), the method comprising:
   (a) isolating nucleic acids from a skin sample adhered to an adhesive patch, the skin sample having been obtained from a subject suspected of having the NMSC;
   (b) contacting the isolated nucleic acids with a set of probes that recognize one or more genes of interest selected from COL5A2, 11,24, AADACL2, PRKACA, and SPP1;
   (c) detecting or measuring an amount of binding between the one or more genes of interest and the set of probes;
   (d) identifying the subject as having NMSC based on the presence of or amount of binding between the one or more genes of interest and the set of probes; and
   (e) performing surgery on the subject identified as having NMSC to remove or partially remove the NMSC from the subject.

2. The method of claim 1, further comprising repeating steps (a)-(c) for a plurality of skin samples.

3. The method of claim 2, further comprising differentiating skin samples having been obtained from the subject suspected of having the NMSC from one or more non-cancer skin samples.

4. The method of claim 3, wherein differentiating comprises generating a plurality of pair-wise interactions between at least two genes of interest in the skin sample.

5. The method of claim 4, further comprising analyzing the plurality of pair-wise interactions to determine an area under a curve (AUC) value for each of the plurality of pair-wise interactions.

6. The method of claim 5, further comprising differentiating the skin sample in the subject suspected of having NMSC from the one or more non-cancer samples when an AUC value is greater than about 0.9.

7. The method of claim 1, wherein the method differentiates primary cutaneous basal cell carcinoma (BCC) and/or squamous cell carcinoma (SCC) samples from benign and precursor lesions for actinic keratosis (AK) and/or seborrheic keratosis (SK).

8. The method of claim 7, wherein differentiation has a sensitivity of at least about 90% and a specificity of at least about 70%.

9. The method of claim 1, wherein the method further comprises providing information regarding one or more of: identification of a disease state, determining likelihood of treatment success for a given disease state, identification of progression of a disease state, or identification of a disease stage.

10. The method of claim 1, wherein the skin sample is from the stratum corneum layer of the subject's skin.

11. The method of claim 1, wherein the skin sample comprises keratinocytes, melanocytes, basal cells, T-cells, or dendritic cells.

12. The method of claim 1, further comprising comparing an amount of binding between the one or more genes of interest and the set of probes to a control or threshold amount of binding.

13. The method of claim 12, comprising identifying the subject as having BCC or SCC, based on the amount of binding between the genes of interest and the set of probes relative to the control or threshold of binding.

14. The method of claim 13, further comprising administering an effective amount of a therapeutic agent to the subject identified as having BCC or SCC.

15. The method of claim 1, wherein the one or more genes of interest comprise five or more of IGFL1, MMP1, COL5A2, IL24, AADACL2, PTCH1, CD68, PRKACA, SPP1, S100A7, CMPK2, IRF7, CXCL1, UPP1, DEFB4A, FOS, OAS3, SCD5, RTP4, and VEGFA.

16. The method of claim 1, further comprising analyzing expression level and mutational changes of a second set of one or more genes of interest.

17. The method of claim 16, wherein the second set of one or more genes of interest comprises TERT.

18. A method for non-invasively identifying a non-melanoma skin cancer (NMSC) comprising basal cell carcinoma (BCC) or squamous cell carcinoma (SCC), comprising:
   (a) identifying a subject suspected of having the NMSC;
   (b) applying an adhesive patch to the subject's skin in a manner sufficient to adhere a skin sample to the adhesive patch;
   (c) removing the adhesive patch from the subject's skin in a manner sufficient to retain the skin sample adhered to the adhesive patch;
   (d) obtaining expression levels of one or more genes of interest selected from COL5A2, IL24, AADACL2, PRKACA, and SPP1, or determining an amount of binding between the one or more genes of interest and a set of probes that recognize the one or more genes of interest;
   (e) determining that the subject has NMSC comprising BCC or SCC based on the expression level of the one or more genes of interest; and
   (f) performing surgery on the subject identified as having NMSC to remove or partially remove the NMSC from the subject.

19. A method of treating a subject with basal cell carcinoma (BCC) or squamous cell skin cancer (SCC), comprising:
   (a) identifying a subject suspected of having BCC or SCC;
   (b) obtaining a skin sample from the subject by applying an adhesive patch to the subject's skin in a manner sufficient to adhere the skin sample to the adhesive patch;
   (c) removing the adhesive patch from the subject's skin in a manner sufficient to retain the skin sample adhered to the adhesive patch;
   (d) isolating nucleic acids from the skin sample;
   (e) contacting the isolated nucleic acids with a set of probes that recognize one or more genes of interest selected from COL5A2, IL24, AADACL2, PRKACA, and SPP1 ;
   (f) detecting or measuring the amount of binding between the one or more genes of interest and the set of probes;
   (g) identifying the subject as having BCC or SCC, based on the amount of binding between the one or more genes of interest and the set of probes; and
   (h) performing surgery on the subject identified as having BCC or SCC to remove or partially remove the BCC or SCC from the subject.

\* \* \* \* \*

UNITED STATES PATENT AND TRADEMARK OFFICE
CERTIFICATE OF CORRECTION

PATENT NO. : 11,976,332 B2
APPLICATION NO. : 16/969526
DATED : May 7, 2024
INVENTOR(S) : John Daniel Dobak, III et al.

It is certified that error appears in the above-identified patent and that said Letters Patent is hereby corrected as shown below:

In the Claims

In Claim 1, Column 56, Line 3:
"selected from COL5A2, 11,24, AADACL2, PRKACA,"
Should read:
--selected from COL5A2, IL24, AADACL2, PRKACA,--

In Claim 19, Column 58, Line 17:
"and SPP1 ;"
Should read:
--and SPP1;--

Signed and Sealed this
First Day of October, 2024

Katherine Kelly Vidal
*Director of the United States Patent and Trademark Office*